（12） United States Patent
Wikswo et al.

(10) Patent No.: US 7,790,443 B2
(45) Date of Patent: Sep. 7, 2010

(54) BIOREACTORS WITH SUBSTANCE INJECTION CAPACITY

(75) Inventors: John P. Wikswo, Brentwood, TN (US); Franz J. Baudenbacher, Franklin, TN (US); Frederick R. Haselton, Nashville, TN (US); William H. Hofmeister, Nashville, TN (US); Charles P. Lin, Brentwood, TN (US); Lisa J. McCawley, Nashville, TN (US); Mark A. Stremler, Franklin, TN (US); Alissa Weaver, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 1301 days.

(21) Appl. No.: 10/525,648

(22) PCT Filed: Aug. 27, 2003

(86) PCT No.: PCT/US03/26800

§ 371 (c)(1), (2), (4) Date: Dec. 14, 2005

(87) PCT Pub. No.: WO2004/020341

PCT Pub. Date: Mar. 11, 2004

(65) Prior Publication Data

US 2006/0154361 A1 Jul. 13, 2006

Related U.S. Application Data

(60) Provisional application No. 60/406,278, filed on Aug. 27, 2002.

(51) Int. Cl.
*C12M 1/00* (2006.01)
*C12M 3/00* (2006.01)

(52) U.S. Cl. ............... 435/289.1; 435/293.1; 435/297.2

(58) Field of Classification Search ... 435/287.1–287.3, 435/288.5–288.7, 289.1–303.3
See application file for complete search history.

(56) References Cited

U.S. PATENT DOCUMENTS 4,391,151 A 7/1983 Nelson et al.

(Continued)

OTHER PUBLICATIONS

Harvath, L. et al, "Rapid quantitation of neutrophil chemotaxis; use of a polyvinylpyrrolidone-free polycarbonate membrane in multiwell assembly," *J. Immunol Method*, vol.37, No. 1, 1980, pp. 39-45.

(Continued)

*Primary Examiner*—Walter D Griffin
*Assistant Examiner*—Shanta G Doe
(74) *Attorney, Agent, or Firm*—Morris, Manning & Martin LLP; Tim Tingkang Xia

(57) ABSTRACT

A bioreactor with substance injection capability. In one embodiment, the bioreactor includes a first substrate having a first surface, an opposite second surface and edges. The bioreactor further includes a second substrate having a first surface and an opposite second surface, defining a cavity with a bottom surface, where the bottom surface is located therebetween the first surface and the second surface. The first surface of the first substrate is received by the second surface of the second substrate to cover the cavity so as to form a chamber for receiving cells and a liquid medium. A port is formed in the second substrate between the bottom surface and the first surface of the second substrate. As formed, the port is in fluid communication with the chamber to allow a stream of substance to be introduced into the chamber. The stream of substance is controlled so as to provide a gradient, or a concentration gradient of the substance, to the chamber. The stream of substance includes a substance affecting the growth of cells such as chemokine.

154 Claims, 40 Drawing Sheets

U.S. PATENT DOCUMENTS

| | | | |
|---|---|---|---|
| 4,988,623 A | | 1/1991 | Schwarz et al. |
| 5,068,195 A * | | 11/1991 | Howell et al. ............ 435/297.2 |
| 5,139,946 A * | | 8/1992 | Howell et al. ............... 435/401 |
| 5,376,548 A | | 12/1994 | Matsuo et al. |
| 5,443,985 A | | 8/1995 | Lu et al. |
| 5,489,515 A | | 2/1996 | Hatschek et al. |
| 5,635,358 A | | 6/1997 | Wilding et al. |
| 5,955,029 A | | 9/1999 | Wilding et al. |
| 6,124,138 A | | 9/2000 | Woudenberg et al. |
| 6,168,948 B1 | | 1/2001 | Anderson et al. |
| 6,171,239 B1 | | 1/2001 | Humphrey |
| 6,267,858 B1 | | 7/2001 | Parce et al. |
| 6,440,645 B1 | | 8/2002 | Yon-Hin et al. |
| 6,660,517 B1 * | | 12/2003 | Wilding et al. ............ 435/289.1 |
| 6,673,594 B1 * | | 1/2004 | Owen et al. ............... 435/284.1 |
| 7,238,323 B2 * | | 7/2007 | Knapp et al. ............... 422/68.1 |
| 2002/0058329 A1 | | 5/2002 | Singh et al. |
| 2002/0106786 A1 | | 8/2002 | Carcalho et al. |
| 2003/0107946 A1 * | | 6/2003 | Cosby et al. ................. 366/127 |
| 2004/0045891 A1 * | | 3/2004 | Gilbert et al. .......... 210/321.65 |

OTHER PUBLICATIONS

Allen et al, "*Improving the Next Generation of Bioartificial Liver Devices*," Seminars in Cell & Developmental Biology, 13, 447-454, 2002.

Augenstein et al., "*Effect of Shear on Death of Two Strains of Mammalian Tissue Cells*," Biotechnol. Bioeng. , 13, 409-418, 1971.

Beeton et al., "*A Novel Membrane Bioreactor for Microbial-Growth*," Appl. Microbiol. Biotechnol. , 40, 812-817, 1994.

Bhujwalla et al., "*Combined Vascular and Extracellular PH Imaging of Solid Tumors*," NMR Biomed., 15,114-119, 2002.

Black et al., "*Diblock Copolymers: Self-Assembly for Applications in Microelectronics*," Encyclopedia of Materials : Science and Technology, Buschow, KHJ, ed. Elsevier, New York, 1-6, 2002.

Black et al., "*Tuominen, M. T. , Integration of Self-Assembled Diblock Copolymers for Semiconductor Capacitor Fabrication*," Appl. Phys. Lett., 79, 409-411, 2001.

Borenstein et al., "*Microfabrication Technology for Vascularized Tissue Engineering, Biomedical Microdevices*," 4, 167-175, 2002.

Boyden, S., "*The Chemotactic Effect of Mixtures of Antibody and Antigen on Polymorphonuclear Leucocytes*," J. Exp. Med., 115, 453-466, 1962.

Brown et al., "*Improvements to Parallel Plate Flow Chambers to Reduce Reagent and Cellular Requirements*," BMC Immunology, 2, 9-16, 2001.

Cinamon et al., "*A Real Time in Vitro Assay for Studying Leukocyte Transendothelial Migration Under Physiological Flow Conditions*," J. Immunol. Methods, 273, 53-62, 2003.

De Bartolo et al., "*A Novel Full-Scale Flat Membrane Bioreactor Utilizing Porcine Hepatocytes: Cell Viability and Tissue-Specific Functions*," Biotechnol. Prog. , 16,102-108, 2000.

Ding et al., "*Chemokines Stimulate Human T Lymphocyte Transendothelial Migration to Utilize VLA-4 in Addition to LFA-1*," J. Leukoc. Biol., 69, 458-466, 2001.

Drioli et al., "*Biocatalytic Membrane Reactors, Applications in Biotechnology and the Pharmaceutical Industry*," Taylor & Francis, London, Philadelphia, 1999.

Dupin et al., "Impact of Colony Morphologies and Disinfection on Biological Clogging in Porous Media," *Environ. Sci. Technol.*, 34, 1513-1520, 2000.

Dupin et al., "Mesoscale and Microscale Observations of Biological Growth in a Silicon Pore Imaging Element," *Environ. Sci. Technol.*, 33, 1230-1236, 1999.

Falk et al., "*A 48-Well Micro Chemotaxis Assembly for Rapid and Accurate Measurement of Leukocyte Migration*," J. Immunol. Methods, 33, 239-247, 1980.

Fink et al., "*Chronic Stretch of Engineered Heart Tissue Induces Hypertrophy and Functional Improvement*," FASEB J., 14, 669-679, 2000.

Folkman et al., "*Tumor Angiogenesis-Therapeutic Implications,*" N. Engl. J. Med., 285, 1182-1186, 1971.

Gillies et al., "*MRI of the Tumor Microenvironment*," J. Magn. Reson. Imaging, 16, 430-450, 2002.

Godbey et al., "*In Vitro Systems for Tissue Engineering*", Ann. N. Y. , Acad. Sci. , 961,10-26, 2002.

Griffith et al., "*Tissue Engineering-Current Challenges and Expanding Opportunities*," Science, 295, 1009-1014, 2002.

Griffith, L. G., "*Emerging Design Principles in Biomaterials and Scaffolds for Tissue Engineering*," Reparative Medicine: Growing Tissues and Organs, 961, 83-95, 2002.

Guarini et al., "*Nanoscale Patterning Using Self-Assembled Polymers for Semiconductor Applications*," J. Vac. Sci. & Tech. B, 19,2784-2788, 2001.

Guarini et al., "*Optimization of Diblock Copolymer Thin Film Self Assembly*," Advanced Materials, 14,1290-1294, 2002.

Guarini et al., "*Process Integration of Self-Assembled Polymer Templates into Silicon Nanofabrication*," Journal of Vacuum Science & Technology B, 20, 2788-2792, 2002.

Hammer et al., "*Measuring Receptor-Mediated Cell Adhesion Under Flow: Cell-Free Systems*," Tissue engineering methods and protocols, Morgan, J. R. and Yarmush, M. L. , eds. Humana Press, Totowa, N. J., 543-552, 1999.

Heidemann et al., "*Angiogenic Effects of Interleukin 8 (CXCL8) in Human Intestinal Microvascular Endothelial Cells Are Mediated by CXCR2*," J. Biol. Chem., 278, 8508-8515, 2003.

Helmlinger, "*Acid Production in Glycolysis-Impaired Tumors Provides New Insights into Tumor Metabolism*," Clin. Cancer Res., 8, 1284-1291, 2002.

Higgs et al., "*Regulation of Actin Filament Network Formation Through Arp2/3 Complex: Activation by a Diverse Array of Proteins*," Annu. Rev. Biochem., 70, 649-676, 2001.

Hu et al., "*Large-Scale Mammalian Cell Culture*," Curr. Opin. Biotechnol., 8, 148-153, 1997.

Jackman et al., "*Electrochemistry and Soft Lithography: A Route to 3-D*," Chemtech, 29,18-30, 1999.

Jain et al., "*Dissecting Tumour Pathophysiology Using Intravital Microscopy*," Nature Reviews Cancer, 2, 266-276, 2002.

Jones et al., "*P-Selectin Mediates Neutrophil Rolling on Histamine-Stimulated Endothelial Cells*," Biophys. J., 65, 1560-1569, 1993.

Kaihara et al., "*Silicon Micromachining to Tissue Engineer Branched Vascular Channels for Liver Fabrication*," Tissue Eng., 6, 105-117, 2000.

Klemke et al., "*CAS/Crk Coupling Serves As a "Molecular Switch" for Induction of Cell Migration*," Journal of Cell Biology, 140, 961-972, 1998.

Labecki et al., "*Protein Transport in Ultrafiltration Hollow-Fiber Bioreactors for Mammalian Cell Culture*," Membrane Separations in Biotechnology, Wang, W. K. , ed., M. Dekker, New York, 1-62, 2001.

Ley, K., "*The Selectins As Rolling Receptors*," The selectins: initiators of leukocyte endothelial adhesion, Vestweber, D, ed. Harwood Academic Publishers, Australia, 63-104, 1997.

Li et al., "*Cortactin Potentiates Bone Metastasis of Breast Cancer Cells*," Cancer Res, 61, 6906-11, 2001.

Li et al., "*Hexagonal Pore Arrays With a 50-420 Nm Interpore Distance Formed by Self-Organization in Anodic Alumina*," J. Appl. Phys., 84, 6023-6026, 1998.

Li et al., "*Initial Stages of Tumor Cell-Induced Angiogenesis: Evaluation Via Skin Window Chambers in Rodent Models*," J Natl Cancer Inst, 92, 143-7, 2000.

Li et al., "*On the Growth of Highly Ordered Pores in Anodized Aluminum Oxide*," Chem. Mater. , 10, 2470-2480, 1998.

Lin et al., "*Antiangiogenic Gene Therapy Targeting the Endothelium-Specific Receptor Tyrosine Kinase Tie2*," Proc. Natl Acad Sci U S A, 95, 8829-34, 1998.

Lin et al., "*Inhibition of Tumor Angiogenesis Using a Soluble Receptor Establishes a Role for Tie2*," in Pathologic Vascular Growth, J Clin Invest, 100, 2072-8, 1997.

Lin et al., "*Inhibition of Tumor Growth by Targeting Tumor Endothelium Using a Soluble Vascular Endothelial Growth Factor Receptor*," Cell Growth Differ, 9, 49-58, 1998.

MacNeill et al., "*Toward a New Blood Vessel*,"Vasc. Med., 7, 41-246, 2002.

Mansky et al., "Controlling Polymer-Surface Interactions With Random Copolymer Brushes," Science, 275,1458-1460, 1997.

Martinez et al., "Acidic PH Enhances the Invasive Behavior of Human Melanoma Cells, Clinical & Experimental Metastasis," 14, 176-186, 1996.

McDonald et al., "Poly (Dimethylsiloxane) As a Material for Fabricating Microfluidic Devices," Accounts of Chemical Research, 35,491-499, 2002.

McDuffie N. G. , Cell Culture Bioreactors. In : Bioreactor Design Fundamentals, Butterworth-Heinemann, Boston, 93-119,1991.

Millward et al., "The Vortex Wave Membrane Bioreactor: Hydrodynamics and Mass Transfer," Chemical Engineering Journal and the Biochemical Engineering Journal, 62, 175-181, 1996.

Mooney et al., "Stabilized Polyglycolic Acid Fibre Based Tubes for Tissue Engineering," Biomaterials, 17, 115-124, 1996.

Munn et al., "Analysis of Cell Flux in the Parallel-Plate Flow Chamber-Implications for Cell Capture Studies," Biophys. J., 67, 889-895, 1994.

Nollert et al., "Hydrodynamic Shear-Stress and Mass-Transport Modulation of Endothelial-Cell Metabolism," Biotechnol. Bioeng., 38, 588-602, 1991.

Papadaki et al., "Quantitative Measurement of Shear-Stress Effects on Endothelial Cells," Tissue engineering methods and protocols, Morgan, J. R. and Yarmush, M. L., eds. Humana Press, Totowa, N. J., 577-593, 1999.

Park et al., "Integration of Cell Culture and Microfabrication Technology," Biotechnol. Prog. , 19, 243-253, 2003.

Passeraub et al., "Design, Microfabrication and Analysis of a Microfluidic Chamber for the Perfusion of Brain Tissue Slices," Biomedical Microdevices, 5, 147-155, 2003.

Powers et al., "A Microfabricated Array Bioreactor for Perfused 3D Liver Culture," Biotechnol. Bioeng. , 78, 257-269, 2002.

Ramos et al., "Quantitative Measurement of Cell-Cell Adhesion Under Flow Conditions," Tissue engineering methods and protocols, Morgan, J. R. and Yarmush, M. L. , eds. Humana Press, Totowa, N. J., 507-519, 1999.

Renard et al., "Induced Changes of Leukocyte Slow Rolling in an in Flow Pharmacological Model of Adhesion to Endothelial Cells," Biorheology, 40,173-178, 2003.

Roth et al., "Characterization of Transendothelial Chemotaxis of T Lymphocytes," J. Immunol. Methods, 188, 97-116, 1995.

Schultz, "Roles of Solute and Heat-Flow in the Development of Polymer Microstructure," Polymer, 32,3268-3283, 1991.

Snyder et al., "Fabrication of Multiple Microscale Features on Polymer Surfaces for Applications in Tissue Engineering," Biomedical Microdevices, 3, 293-300, 2001.

Solan et al., "Engineered Vessels: Importance of the Extracellular Matrix," Transplant. Proc., 33, 66-68, 2001.

Tobert et al., "Perfusion Culture Systems for Production of Mammalian Cell Biomolecules," Large-Scale Mammalian cell culture, Feder, J. and Tolbert, W. R., eds., Academic Press, Orlando, 97-123, 1985.

Voisard et al., "Potential of Cell Retention Techniques for Large-Scale High-Density Perfusion Culture of Suspended Mammalian Cells," Biotechnol. Bioeng. , 82,751-765, 2003.

Walheim et al., "Structure Formation Via Polymer Demixing in Spin-Cast Films," Macromolecules, 30, 4995-5003,1997.

Weidner et al., "Tumor Angiogenesis and Metastasis-Correlation in Invasive Breast-Carcinoma," N. Engl. J. Med., 324, 1-8, 1991.

Whitesides et al. , Ingber, D. E., "Soft Lithography in Biology and Biochemistry," Annual Review of Biomedical Engineering, 3,335-373, 2001.

Wu et al. "Fabrication of Complex Three-Dimensional Microchannel Systems in PDMS," J. Am. Chem. Soc., 125, 554-559, 2003.

Xia et al., "Soft Lithography," Annual Review of Materials Science, 28,153-184, 1998.

Yao et al., "Chemotaxis by A Cns Macrophage," the Microglia, J. Neurosci. Res., 27, 36-42, 1990.

Jain et al., "In Vitro and in Vivo Quantificatiaon of Adhesion Between Leukocytes and Vascular Endothelium," Tissue engineering methods and protocols, Morgan, J.R. and Yarmush, M. L.,, eds. Humana Press, Totowa, N. J., 553-575, 1999.

Jain, R. K., "Angiogenesis and Lymphangiogensis in Tumors: Insights from Intravital Microscopy," Cold Spring Harb. Symp. Quant. Biol., 67, 239-248, 2002.

Murdin et al., "Immobilisation and Growth of Hybridomas in Packed Beds," Bioreactors and Biotransformations, Moody, G. W. and Baker, P. B., eds. Elsevier Applied Science Publishers, London, New York, 99-110, 1987.

\* cited by examiner

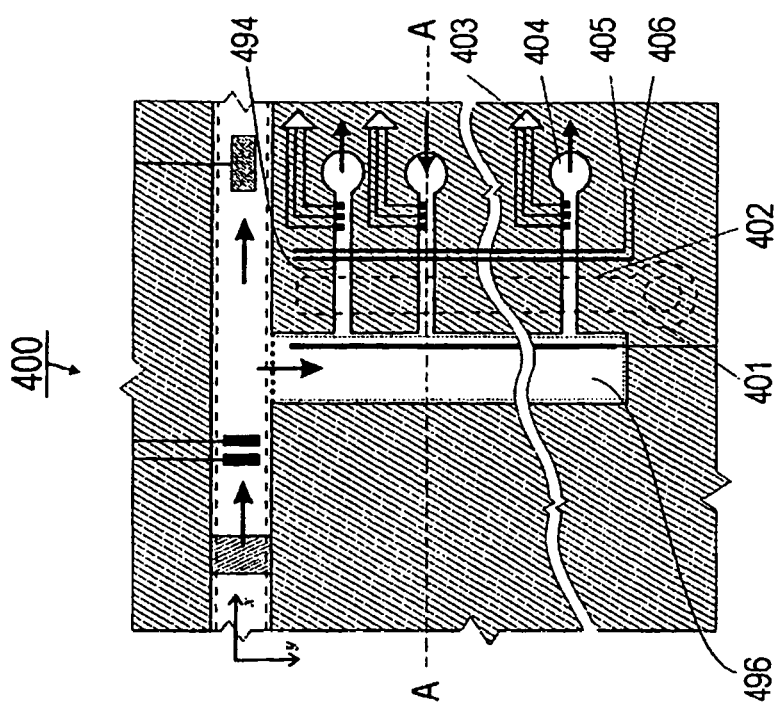
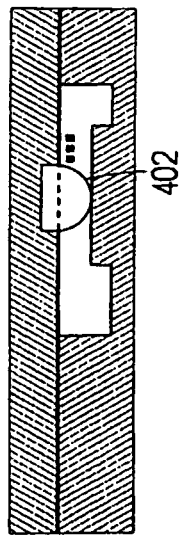
Fig. 4A
Fig. 4B

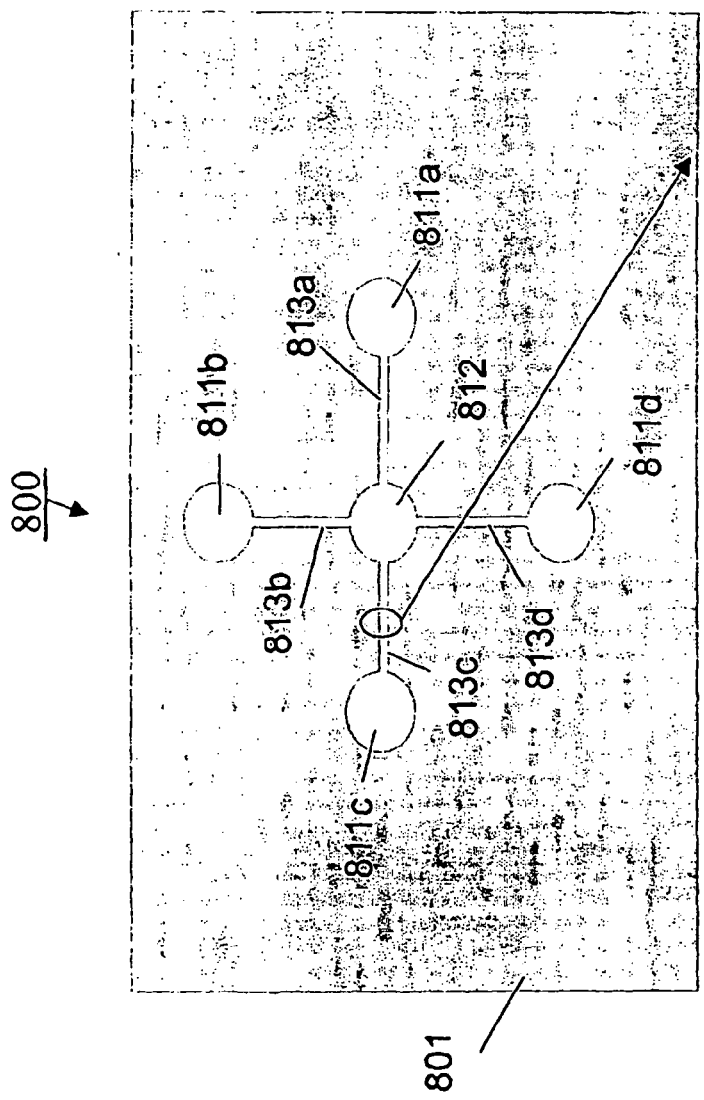
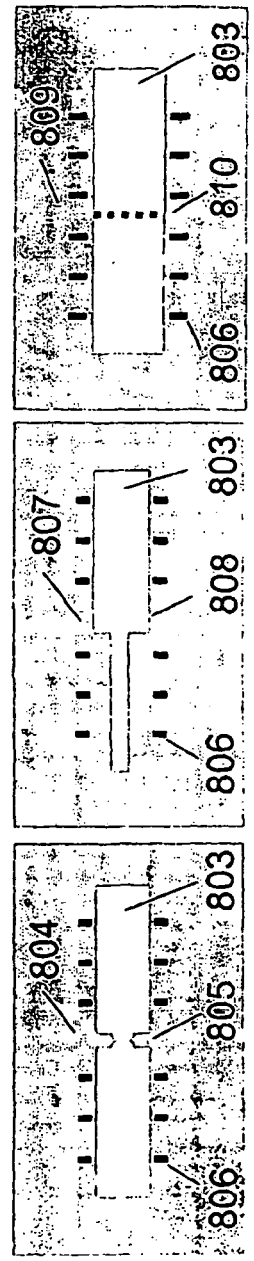
Fig. 8A
Fig. 8B
Fig. 8C
Fig. 8D

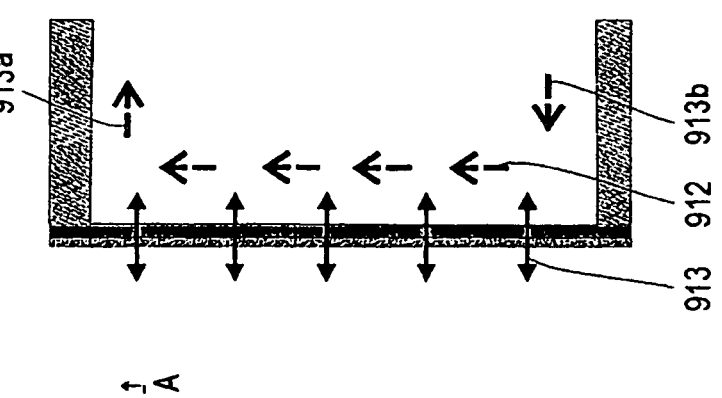
Fig. 9D2
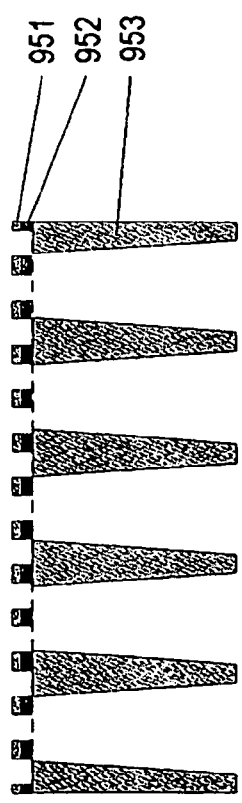
Fig. 9D3
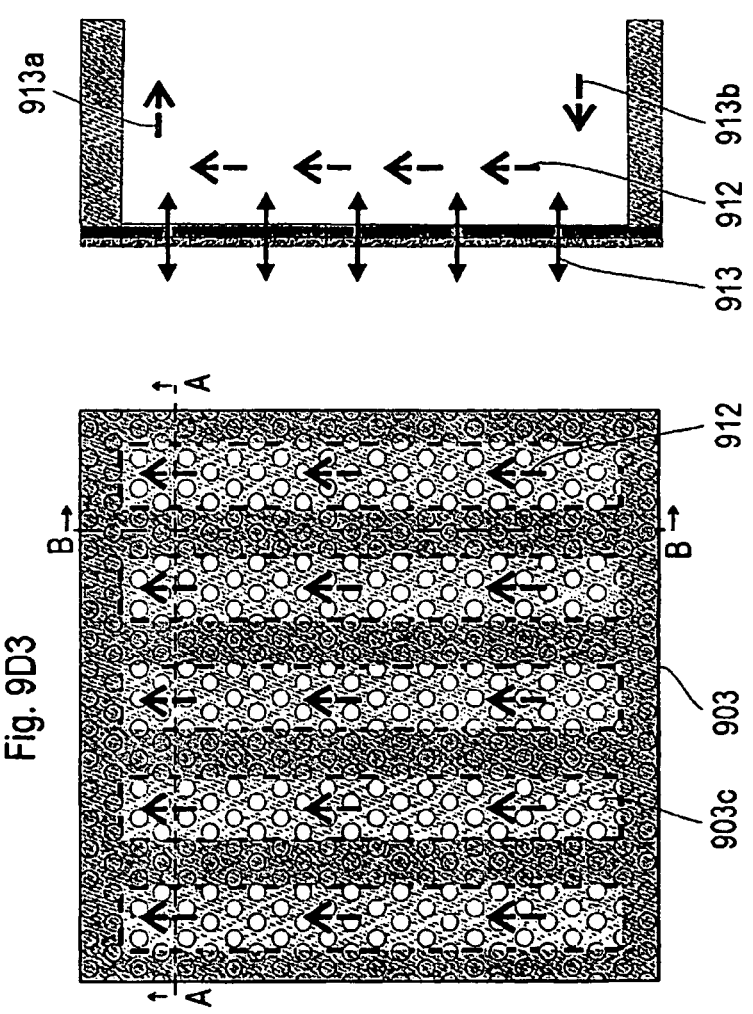
Fig. 9D1

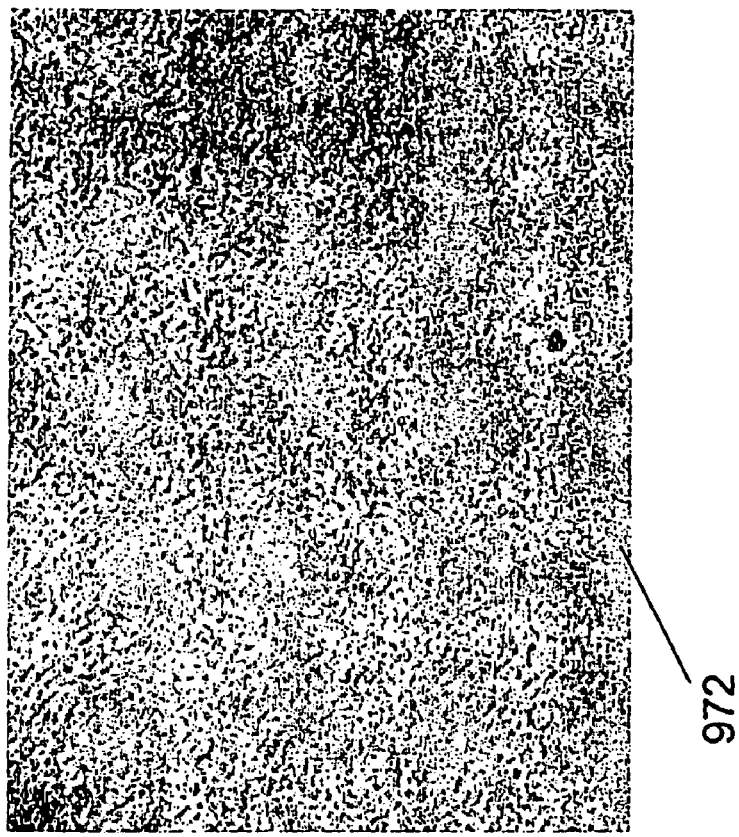
Fig. 9E2
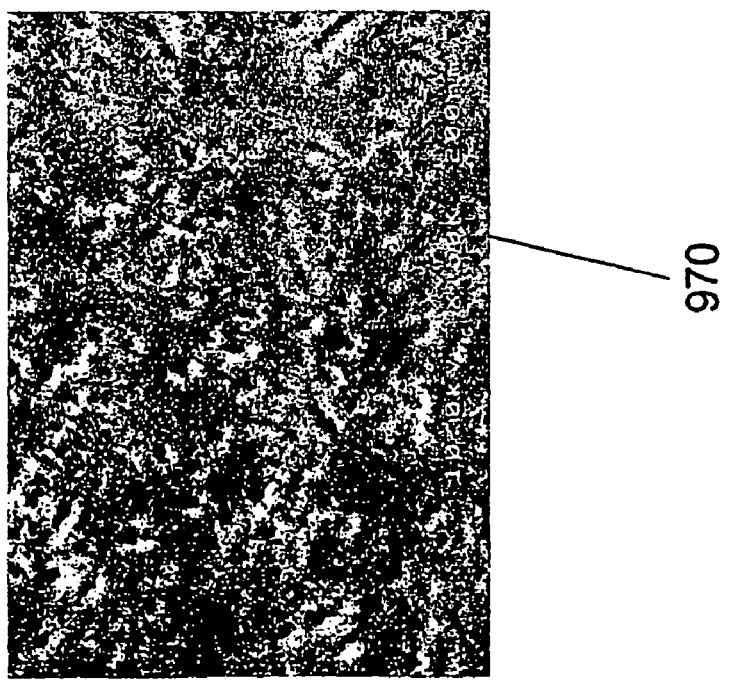
Fig. 9E1

Fig. 9G2
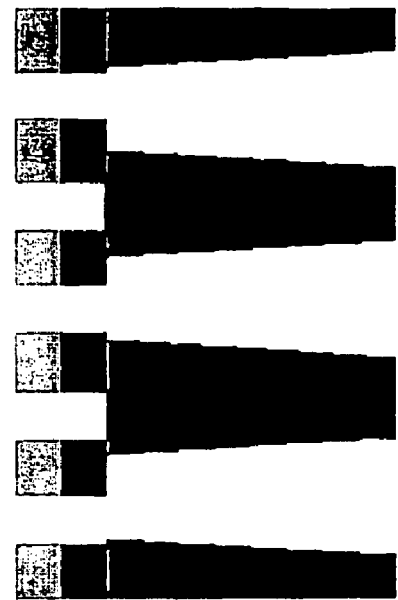
Fig. 9G4
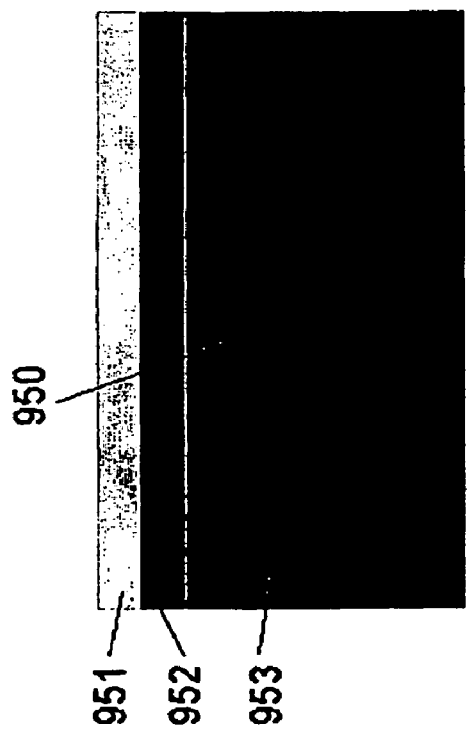
Fig. 9G1
950
951
952
953
Fig. 9G3

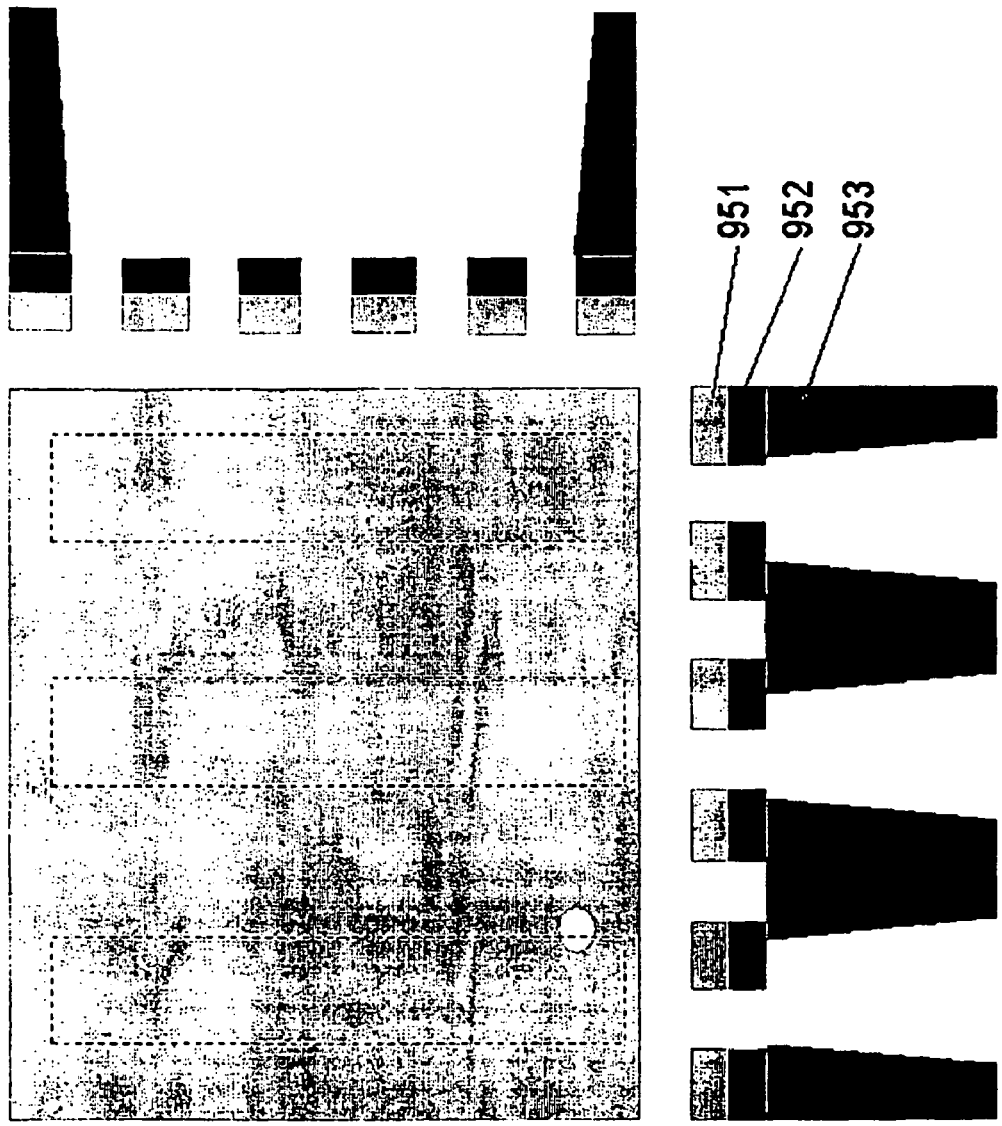
Fig. 9G5

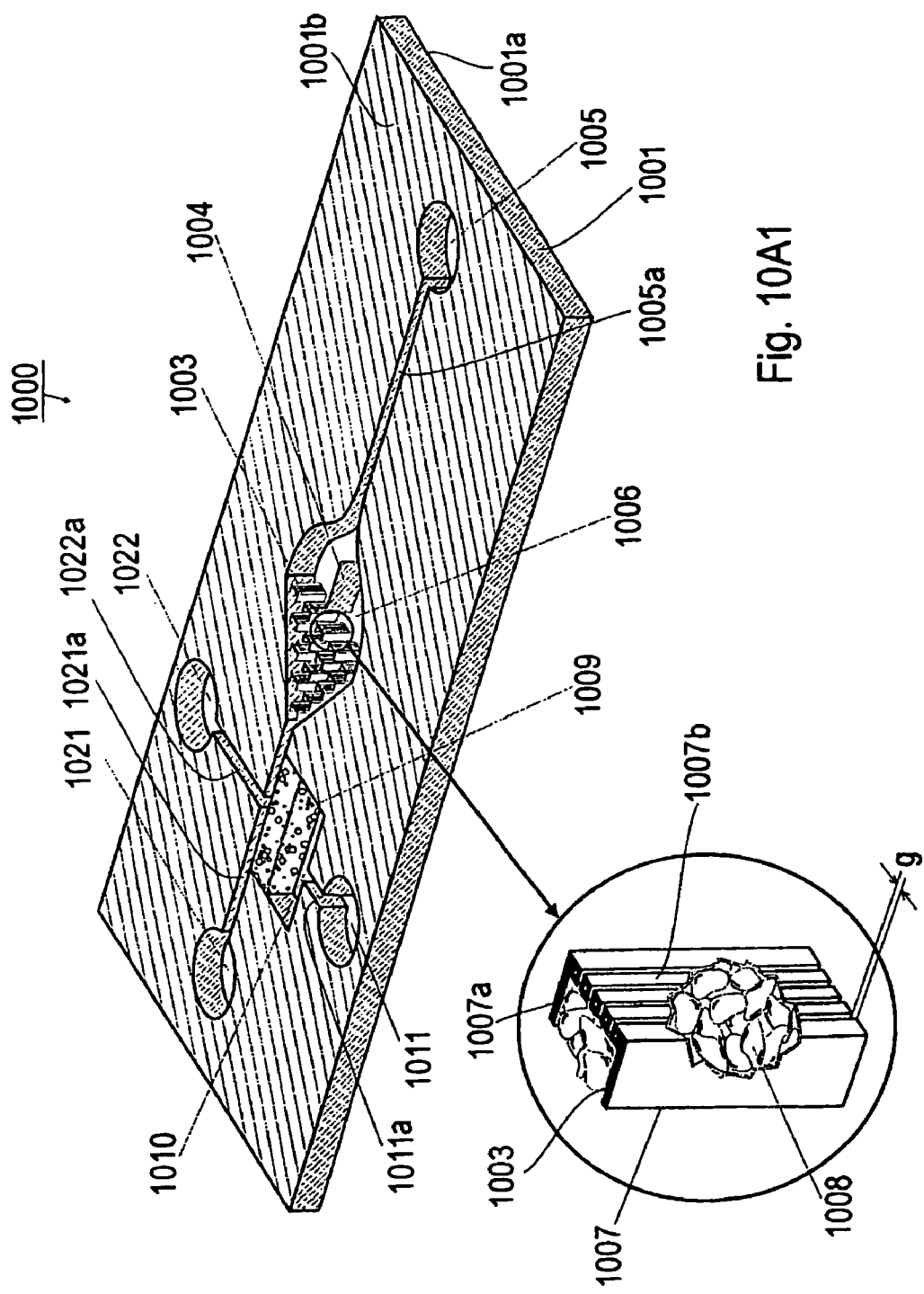
Fig. 10A1
Fig. 10A2

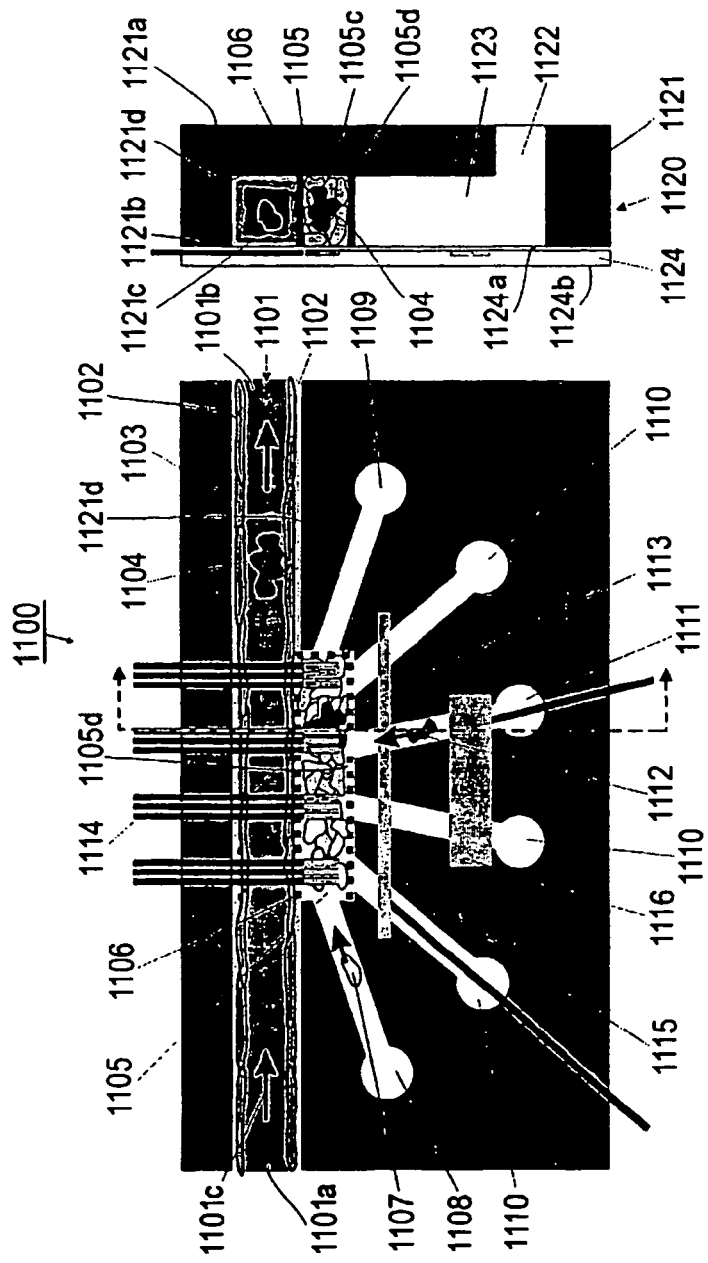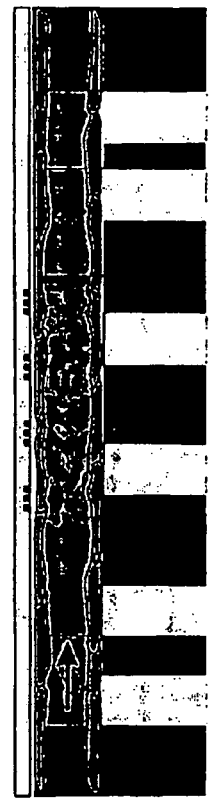
Fig. 11A1
Fig. 11A2
Fig. 11A3

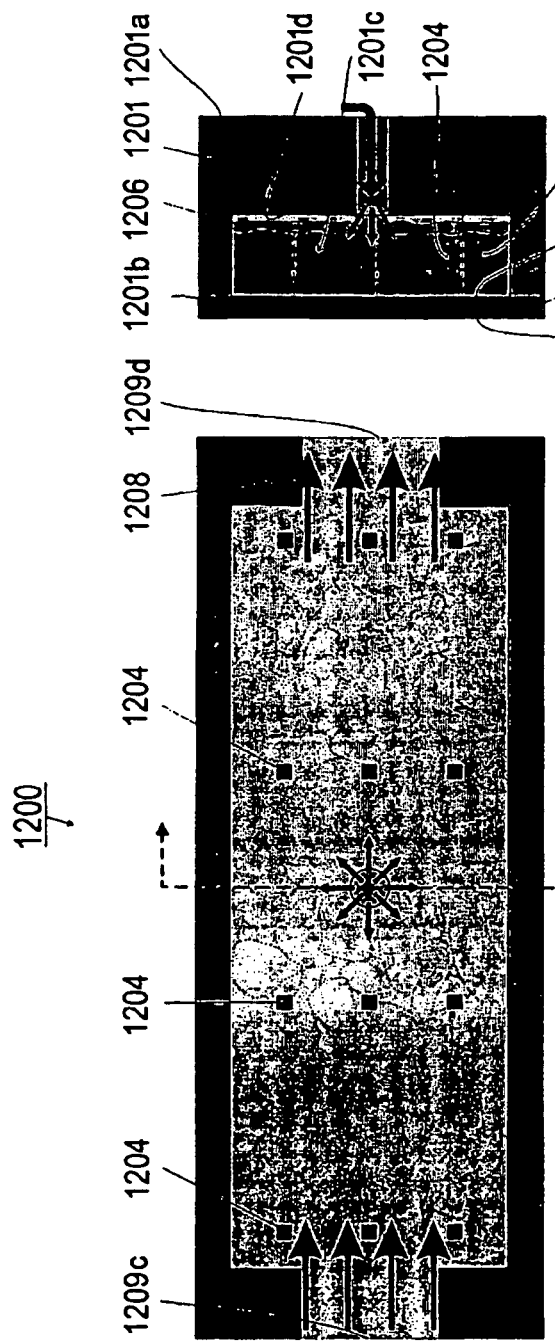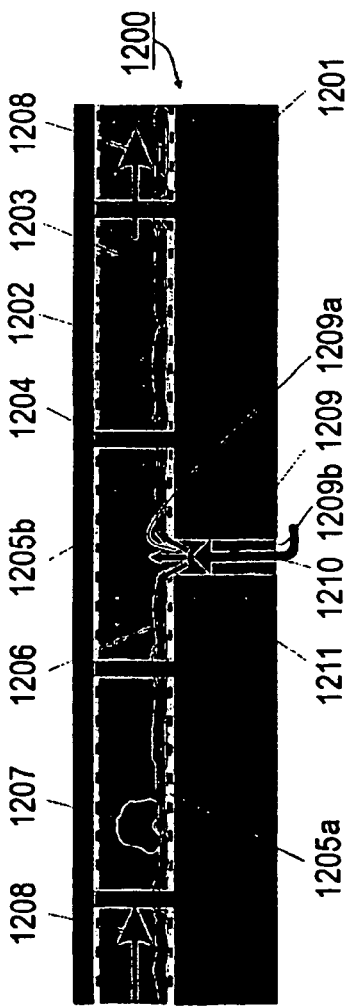
Fig. 12A1
Fig. 12A2
Fig. 12A3

BIOREACTORS WITH SUBSTANCE INJECTION CAPACITY

The present invention was made with Government support under Grant No. N66001-01-C-8064 awarded by the Defense Advanced Research Projects Administration and the Office of Naval Research. The United States Government may have certain rights to this invention pursuant to these grants.

This application is being filed as a PCT International Patent application in the name of Vanderbilt University, a U.S. national corporation, applicant for the designation of all countries except the US, and John P. Wikswo and Franz J. Baudenbacher, both U.S. nationals and residents, applicants for the designation of the US only, on 27 Aug. 2003.

Some references, which may include patents, patent applications and various publications, are cited in a reference list and discussed in the description of this invention. The citation and/or discussion of such references is provided merely to clarify the description of the present invention and is not an admission that any such reference is "prior art" to the invention described herein. In terms of notation, hereinafter, "[n]" represents the nth reference cited in the reference list. For example, [11] represents the 11th reference cited in the reference list, namely, Hu, W. S. and Aunins, J. G., Large-Scale Mammalian Cell Culture, Curr. Opin. Biotechnol., 8, 148-153, 1997.

FIELD OF THE INVENTION

The present invention generally relates to an apparatus and methods for growing and maintaining a living system. More particularly, the present invention relates to an apparatus and methods that have a channel configuration allowing perfusate flow with diffusional exchange to tissue cells but no cell migration. Additionally, the present invention relates to an apparatus and methods that have capacity for growing and maintaining a living microorganism such as protozoa.

The present invention also relates to an apparatus and methods for dynamic analysis of a collection of cells such as a biofilm. More particularly, the present invention relates to an apparatus and methods for measuring response of a biofilm to one or more dynamic streams of substance such as chemical stressors at various depths of the biofilm.

Certain embodiments of the present invention comprise apparatus and methods for growing and maintaining a living system such as a cell or a collection of cells and monitoring the status of such a living system that is metabolically active and responsive to environmental change, wherein each metabolic activity of the cell may be characterized by a characteristic time. More particularly, the apparatus and methods comprise bioreactors with multiple chambers and methods of using the same.

Certain other embodiments of the present invention comprise apparatus and methods for growing and maintaining a living system such as a cell or a collection of cells and monitoring the status of such a living system that is metabolically active and responsive to environmental change, wherein each metabolic activity of the cell may be characterized by a characteristic time. More particularly, the apparatus and methods comprise bioreactors with an array of chambers with a common feed line and methods of using the same.

Certain additional embodiments of the present invention comprise apparatus and methods for growing and maintaining a living system such as a cell or a collection of cells and monitoring the status of such a living system that is metabolically active and responsive to environmental change, wherein each metabolic activity of the cell may be characterized by a characteristic time. More particularly, the apparatus and methods comprise capillary perfused bioreactors and methods of using the same.

Certain further embodiments of the present invention comprise apparatus and methods for growing and maintaining a living system such as a cell or a collection of cells and monitoring the status of such a living system that is metabolically active and responsive to environmental change, wherein each metabolic activity of the cell may be characterized by a characteristic time. More particularly, the apparatus and methods comprise bioreactors with substance injection capability and methods of using the same.

BACKGROUND OF THE INVENTION

Bioreactor is a device that can be used for culturing living cells. More particularly, bioreactors are vessels that provide a proper physical and chemical environment as well as fast transport of substrates and products to allow cellular biological reactions to occur, ideally rapidly and efficiently. The simplest bioreactor is a culture dish: In conventional cell culture using well-plates, culture-dishes, and flasks, the volume of the culture medium is typically 200 to 1000 times the volume of the cells. This ratio, when used in combination with buffering of the culture media, allows the cells to grow for at least 24 hours without media change. However, another consequence of this ratio is a corresponding dilution of whatever extracellular factors are produced by the cells and might otherwise provide paracrine cell-to-cell communication, which is possible in tissue because the extracellular volume might be only 10% of intracellular volume.

Much of the development of bioreactors was directed towards either the functional tissues, or the generation of biochemicals and pharmaceuticals. For example, over the last 20 years studies on the generation of skin, pancreas, cartilage, liver, cornea and bladder have taken particular importance[1]. In the United States alone, there are more than 80,000 individuals waiting for an organ transplant, and hence the need to develop improved bioreactor technology is self-evident. There is also a growing recognition that progress in understanding cell motility and chemotactic signaling, as well as other complex cellular processes, is often constrained by the laboratory techniques available for observing and intervening at various points in the processes. Many of these processes can be examined best in a properly instrumented bioreactor.

There is a wide variety in bioreactors, including stirred vessels, bubble column, packed beds[2], air-lift reactors, and membrane reactors[3] that include plates, rotating plates, spiral-wound and hollow fibres. Hollow-fiber reactors are of special importance since (depending of their structure) they may allow as much as 30,000 $m^2$ of membrane area per $m^3$ module volume[4-6]. However, given that mammalian cells are very sensitive to shear forces[7-9] (which originate mainly from agitation and aeration), it is important to reduce the forces as much as possible in the reactor where the cells will be grown[9,10]. Membranes have been used in bioreactors to increase survival of cells. For instance, it has been known that liquid-gas interface created in some models of reactors is particularly damaging for mammalian cells. That potentially lethal interface can be eliminated by the use of a hydrophobic membrane[9].

Bioreactors may be also classified by means of their mode of operation: batch, fed-batch and continuous cultivation (also called perfused cultivation). In the first or batch mode, no substrate is added, nor medium removed; in the case of the fed-batch mode there is a continuous feeding, but nothing is removed until the reactions are terminated and the reactor emptied. While these systems imply a low effort for process control, the productivity is low compared to that in perfused systems, the third mode, where a permanent inflow of substrate and outflow of medium takes place. Besides the high productivity, there is a better cell physiology control in this kind of reactors[11] and in the case of mammalian cell culture, it has been shown to provide significant advantage over static methods[12,13].

One of the limitations when developing large three-dimensional tissues is the lack of a proper vascular supply for nutrient and metabolite transport. A number of studies have analyzed the artificial vascular networks[14-18], and there have been a number of attempts to construct functional microfabricated scaffolds[5,16,19-21]. The techniques by which these networks have been produced include plasma etching, photolithography, soft lithography, microcontact printing, microfluidic patterning using microchannels, laminar flow patterning and stencil patterning[22-25]. In the case of plasma etching technologies we can consider the high aspect ratio micromachining (HARMS) as a very powerful tool since it allows to etch channels of virtually unlimited depth without increasing the width already achieved by lithography[22]. It is also possible to construct three dimensional microchannel systems in PDMS with complex topologies and geometries[15].

Additionally, one needs to realize that the growth of clinically-implantable tissue may require the ultimate biodegradation and the mechanical properties of the tissue scaffold[16]. These properties are directly related to the crystallinity, molecular weight, glass transition temperature and monomer hydrophobicity of the materials chosen to fabricate the tissue[19]. Naturally derived materials such as collagen have been employed[26], as well as synthetic and semi synthetic ones. Polyglycolic acid (PGA) possesses high porosity and it makes easy the fabrication of devices, therefore, PGA fibre meshes have been considered to transplant cells. However, they cannot resist significant compressional forces. An alternative to solve this problem is to use polymers of lactic and glycolic acid whose ratios can be adjusted to control the crystallinity of the material and hence the degradation rate and mechanical properties. Fibre-based tubes have been fabricated from these polymers[27].

It is important to compare the vascular nature of living tissue with the capabilities provided by existing microfabricated cell-perfusion bioreactor systems. In tissue, arteries divide into progressively smaller vessels, eventually reaching arterioles and then capillaries. The arterioles are important because they contain the precapillary sphincters, which allow control of the perfusion of individual capillary beds, but also provide the majority of the peripheral resistance and hence the pressure drop associated with the arterial supply. As a result, the pressure difference across the capillary endothelium membrane is kept sufficiently low to allow diffusional transport of nutrients and metabolites across the membrane, as well as the trafficking of immune cells required for tissue maintenance and infection control. Were the pressures in the capillaries as high as those in the arterioles, the capillary wall thickness would be too great to allow these critical transport phenomena. The venous return system is in many ways a mirror of the arterial system, albeit at lower pressures. Another feature of the living vascular system is that the branching process described above allows all cells to be within 50 to 200 microns of a capillary, depending upon the specific tissue. As a result, the arterial supply and venous return systems are intercalated in such a manner that every capillary that perfuses a large group of cells is connected to the larger supply and return systems with a self-similarity that ensures uniform perfusion and transcapillary pressures. It is this intercalation process that is so difficult to replicate with microfabrication. For example, Borenstein et al.,[22] describe a process to build a two-dimensional vascular system that could create a multi-scale perfusion system for supporting endothelial cells, but there is no provision to selectively limit diffusive transport across the smallest capillaries to perfuse cells lying outside of the perfusion network. More importantly, the networks they show have a large region of the device that is covered with the larger vessels, and the region of the bioreactor that is limited to capillary vessels is in fact quite small.

Thus, there is a need for microfabricated migration bioreactors that mimic in vitro the microenvironments of normal tissue was well as that of tumors, infected tissue, and wounded tissue, while providing independent control of chemokine and growth factor gradients, shear forces, cellular perfusion, and the permeability of physical barriers to cellular migration, thereby allowing detailed optical and electrochemical observation of normal, immune, and cancerous cells during cell migration, intravasation, extravasation, and angiogenesis. Angiogenesis, tumor metastasis, and leukocyte infiltration into tissue are complex processes that are regulated not only by cellular responses to a single chemokine, but also by external factors, such as multiple competing chemokine and growth factor signals, autocrine feedback loops, cell-cell interactions, and mechanical forces such as vessel shear stress. Current approaches for assessing migration across cellular barriers include Boyden and transwell chambers that provide an integrated fluorescence assay of migration across filters to allow quantitation of migration[28-34], parallel plate flow chambers[35-38], in which adhesion and rolling on endothelial cells in shear stress can be assessed[35,39-44], and in vivo intravital microscopy in which migration of cells in living animals is visualized[45-48]. Each of these approaches has limitations, including the inability to have sustained and controlled chemotactic gradients (all systems), the inability to visualize migration in real time or with physiologic shear stress (Boyden and transwell chambers), the inability to observe extravasation or angiogenesis into an underlying, deep cellular matrix (parallel plate flow chambers) and the inability to control all aspects of the experiments, e.g., having defined cell populations and controlled microfluidics for independent control of shear and tissue perfusion (all systems, especially intravital microscopy). The development of a motility/metastasis model system with independent control of endothelial shear stress, chemokine gradients, tissue perfusion, and the ability to add different cell types through different ports, combined with state-of the art imaging techniques and sensor capabilities would represent a huge advance over currently available systems.

Indeed, the need for such capabilities is quite urgent. Angiogenesis is a dynamic process, influenced by the cellular microenvironment and intricately linked to metastasis[49,50]. It has been demonstrated that both VEGF and angiopoietin/ tyrosine kinase (Ang/Tie2) function are required for tumor angiogenesis[51-53]. However, how signals from those two receptor systems are integrated to mediate angiogenesis has not been determined, in part due to the lack of good model systems. The next step would be to study the coordination and integration of VEGF and Ang signaling in endothelial cell migration, vascular sprouting and maturation, and tumor transendothelium migration. As with angiogenesis, multiple environmental inputs affect tumor metastasis and leukocyte infiltration. Activation of one chemokine receptor in tumor cells affects the induction of other ligands and receptors in tumor cells as well as endothelial cells and leukocytes, but the mechanism is poorly understood[54]. There is a need for an understanding of how alteration of chemokine receptor internalization and/or changes in receptor association with adaptor molecules such as AP-2 or beta-arresting affect chemokine receptor activity as tumor cells move through a complex matrix. How external factors such as cell-cell adhesion, cell-matrix interactions, and vessel shear stress affect cytoskeletal reorganization during migration through tissues is also poorly understood. Cortactin overexpression increases the metastasis of breast cancer cells to bone[55], however the mechanism remains unclear. Likewise, lack of WASp protein in humans leads to an X-linked immune disorder that may result from signaling, proliferation or chemotaxis defects[56]. There is a need to study the role of cortactin and WASp proteins in chemotaxis of breast cancer and HL60 cells in a complex multicell environment involving controllable shear, cell-cell interactions, and chemokine gradients. As a final example, matrix metalloproteinases (MMPs) are extracellularly expressed enzymes found in many types of cancer and are thought to be important in tumor development, growth, invasion and metastasis. It has recently been discovered that skin tumors that develop in mice deficient for MMP-3 (MMP-3 null mice) progress and grow much faster than skin tumors from normal, wild-type mice. This difference is associated with a reduced number of immune cells in the tumor and surrounding tissue in the MMP-3 null mice. The logical progression of this research is to determine how loss of an MMP affects the ability of immune cells, namely monocytes and neutrophils, to infiltrate from the peripheral blood circulation to the tumor site. The ability to control the experimental environment, including multiple defined cell populations, is critical to elucidate the relative importance of tumor-host interactions in MMP-3 induced cellular chemotaxis.

Despite the progress made over the years, however, currently available bioreactors cannot provide a more physiologic environment that would include a three-dimensional in vitro region with multiple cell types, stimuli, and measurement capabilities and allows study of molecular aspects of the chemotactic response. Thus, bioreactors that mimic in vitro the microenvironments of tumors and tissue while providing independent control of chemokine and growth factor gradients, shear forces, cellular perfusion, and the permeability of physical barriers to cellular migration, thereby allowing detailed optical and electrochemical observation of normal and cancerous cells during cell migration, intravasation, extravasation, and angiogenesis need to be developed.

Therefore, a heretofore unaddressed need exists in the art to address the aforementioned deficiencies and inadequacies.

SUMMARY OF THE INVENTION

In one aspect, the present invention relates to a bioreactor with substance injection capability. In one embodiment, the bioreactor includes a first substrate having a first surface, an opposite second surface and edges. The bioreactor further includes a second substrate having a first surface and an opposite second surface, defining a cavity with a bottom surface, where the bottom surface is located therebetween the first surface and the second surface. The first surface of the first substrate is received by the second surface of the second substrate to cover the cavity so as to form a chamber for receiving cells and a liquid medium. The second substrate can be fabricated from glass, Mylar, PDMS, silicon, a polymer, a semiconductor, or any combination of them.

A port is formed in the second substrate between the bottom surface and the first surface of the second substrate with a first opening and an opposite, second opening. As formed, the port is in fluid communication with the chamber through the first opening to allow a stream of substance to be introduced into the chamber through the port substantially along a first direction. The stream of substance is controlled so as to provide a gradient, or a concentration gradient of the substance, to the chamber at least around the first opening. The stream of substance includes a substance affecting the growth of cells such as chemokine.

The second substrate further defines a third opening and an opposite fourth opening adapted for allowing a flow of liquid to be introduced into the chamber through the third opening and away from the chamber through the fourth opening substantially along a second direction. The second direction is substantially perpendicular to the first direction.

The bioreactor further includes a biocompatible coating layer applied to the bottom surface of the second substrate. The biocompatible coating layer includes a material that may inhibit cell adhesion to the biocompatible coating layer, enhance cell adhesion to the biocompatible coating layer, or function as a fluorescent marker or indicator of the state of cells.

In forming the bioreactor, the first surface of the first substrate and the second surface of the second substrate is spaced such that when a layer of cells grows on the biocompatible coating layer, a flow of liquid can flow in the chamber between the first surface of the first substrate and the layer of cells along the second direction. The flow of liquid is controlled so as to provide a known shear force to the layer of cells. The flow of liquid may be further controlled so as to provide perfusion and maintenance to the layer of cells. In other words, this flow can perfuse all cells in the chamber, and can be intermittent only as allowed by cell maintenance. The cells can be any type of living cells, including, but not limited to, bacteria, protozoa, or both, normal cells, tumor cells, or any combination of them. Cells can be introduced into a chamber individually, in a collection of cells, or in the form of biofilm.

Moreover, the first surface of the first substrate and the second surface of the second substrate are spaced to further allow at least one cell to migrate above the layer of cells. The at least one cell to migrate can be a cell having a type that is the same or different from the type of the layer of cells.

In an alternative embodiment of the present invention, the bioreactor further includes a layer of porous material that is positioned on the bottom surface of the second substrate. A biocompatible coating layer can be applied to the layer of porous material such that the layer of porous material is between the biocompatible coating layer and the bottom surface of the second substrate. The biocompatible coating layer includes a material that may inhibit cell adhesion to the biocompatible coating layer, enhance cell adhesion to the biocompatible coating layer, or function as a fluorescent marker or indicator of the state of cells.

In this embodiment, the first surface of the first substrate and the second surface of the second substrate are spaced such that when a layer of cells grows on the biocompatible coating layer, a flow of liquid can flow in the chamber between the first surface of the first substrate and the layer of cells. The flow of liquid can also be controlled so as to provide a known shear force to the layer of cells. As such formed, the chamber is divided by the biocompatible coating layer into two regions: an upper region for flow, and a lower region for cell extravasation and/or other cell activities.

The layer of porous material can include collagen, an extracellular matrix, at least one cell culture scaffold supportive to the layer of cells, or any combination of them. The layer of porous material may allow at least one cell to extravasate below the layer of cells.

The first substrate is at least partially optically transparent. A biocompatible coating layer may be applied to the first surface of the first substrate, where the biocompatible coating layer includes a material that may inhibit cell adhesion to the biocompatible coating layer, enhance cell adhesion to the biocompatible coating layer, or function as a fluorescent marker or indicator of the state of cells.

The first substrate and the second substrate are substantially parallel to each other and a plurality of posts are positioned between the first surface of the first substrate and the second surface of the second substrate to substantially maintain a predetermined separation between the first surface of the first substrate and the second surface of the second substrate to allow optical detecting of dynamic activities of cells in the chamber. The dynamic activities of cells in the chamber are detectable through optical detecting means such as high-resolution optical microscope or a fluorescence-imaging device or both.

The predetermined separation between the first surface of the first substrate and the second surface of the second substrate should be maintained with sufficient accuracy for accurate optical measurements. To this end, the plurality of posts are positioned in at least two rows, and wherein each row of posts has at least two posts spaced from each other to form a stable support structure.

In an alternative embodiment, a bioreactor with a chamber is provided with perfusion means in fluid communication with the chamber to allow diffusional exchange of nutrients and metabolic byproducts with the chamber.

The perfusion means includes a nanofilter with a plurality of pores in fluid communication with the chamber, wherein the pores are sized to allow diffusional exchange of nutrients and metabolic byproducts with the chamber and not to allow cells to migrate across the nanofilter. The pores may be further sized to allow cells to perfuse through only by bi-directional diffusion through the nanofilter in a manner such that substantially no shear is generated by the perfusion of cells. In one embodiment, the pores of the nanofilter are sized to have a dimension smaller than 400 nanometers cross-sectionally.

The perfusion means further includes a perfusion supply network in fluid communication with the nanofilter through the pores. In one embodiment, the perfusion supply network includes a plurality of perfusion channels, each being in fluid communication with the nanofilter to allow bidirectional, diffusional exchange of nutrients and metabolic byproducts with the nanofilter and being dimensioned to minimize pressure drops along each perfusion channel and to allow passive diffusional exchange of nutrients and metabolic byproducts along each perfusion channel.

The perfusion supply network further includes a plurality of intermediate supply channels, each being in fluid communication with a plurality of corresponding perfusion channels so as to provide perfusate to the plurality of corresponding perfusion channels. Moreover, the perfusion supply network has a plurality of intermediate return channels, each being in fluid communication with a plurality of corresponding perfusion channels so as to collect perfusate from the plurality of corresponding perfusion channels.

Additionally, the perfusion supply network further includes a plurality of main supply channels, each being in fluid communication with a plurality of corresponding intermediate supply channels so as to provide perfusate to the plurality of corresponding intermediate supply channels, and a plurality of main return channels, each being in fluid communication with a plurality of corresponding intermediate return channels so as to collect perfusate from the plurality of corresponding intermediate return channels.

In another aspect, the present invention relates to yet another bioreactor for cultivating living cells in a liquid medium. In one embodiment, the bioreactor includes a first substrate having a first surface, an opposite second surface and edges. The bioreactor further includes a second substrate having a first surface and an opposite second surface, defining a cavity with a bottom surface, where the bottom surface is located therebetween the first surface and the second surface. The first surface of the first substrate is received by the second surface of the second substrate to cover the cavity so as to form a chamber for receiving cells and a liquid medium. The second substrate can be fabricated from glass, Mylar, PDMS, silicon, a polymer, a semiconductor, or any combination of them.

The bioreactor further includes a filter dividing the chamber into a first subchamber and a second subchamber, wherein the filter has a porosity to allow the first subchamber and the second subchamber in fluid communication. Additionally, a port is formed in the second substrate between the bottom surface and the first surface of the second substrate with a first opening and an opposite, second opening. As formed, the port is in fluid communication with the second subchamber through the first opening to allow a stream of substance to be introduced into the chamber through the port substantially along a first direction. The stream of substance is controlled so as to provide a gradient, or a concentration gradient of the substance, to the chamber at least around the first opening. The stream of substance includes a substance affecting the growth of cells such as chemokine.

The second substrate further defines a third opening and an opposite fourth opening adapted for allowing a flow of liquid to be introduced into at least one of the first subchamber and the second subchamber through the third opening and away from at least one of the first subchamber and the second subchamber through the fourth opening substantially along a second direction. The second direction is substantially perpendicular to the first direction. Same or different flows of liquid can be introduced to one or both of the first subchamber and the second subchamber, jointly or independently.

The filter has a first surface that partially defines the first subchamber with the first surface of the first substrate, and an opposite second surface that partially defines the second subchamber with the second surface of the second substrate. The filter includes a perfusion membrane with a plurality of pores to allow the filter to be in fluid communication with one or both of the first subchamber and the second subchamber. The pores of the filter are sized to allow diffusional exchange of nutrients and metabolic byproducts with one or both of the first subchamber and the second subchamber but not to allow cells to migrate across the filter. The pores are further sized to allow cells to perfuse through the filter only by bi-directional diffusion in a manner such that substantially no shear is generated by the perfusion of cells. In one embodiment, the pores of the filter are sized to have a dimension smaller than 400 nanometers cross-sectionally. In a more preferred embodiment, the pores of the filter are sized to have a dimension about 10 to 100 nanometers cross-sectionally.

The bioreactor further includes a plurality of posts that are strategically positioned between the first surface of the first substrate and the first surface of the filter to substantially maintain a predetermined separation between the first surface of the first substrate and the first surface of the filter to allow optical detecting of dynamic activities of cells in the first subchamber. Additionally, the bioreactor includes a plurality of posts that are strategically positioned between the second surface of the second substrate and the second surface of the filter to substantially maintain a predetermined separation between the second surface of the second substrate and the second surface of the filter to allow optical detecting of dynamic activities of cells in the second subchamber.

The predetermined separation between the first surface of the first substrate and the first surface of the filter and the predetermined separation between the second surface of the second substrate and the second surface of the filter should be maintained with sufficient accuracy for accurate optical measurements, respectively. To this end, the plurality of posts and are positioned in at least two rows, respectively, and where each row of posts has at least two posts spaced from each other to form a stable support structure. Posts may be positioned away from each other.

As such formed, when a first flow of liquid is introduced into the first subchamber, the first flow of liquid can be controlled so as to provide a known shear force to a first layer of cells growing in the first subchamber on the first surface side of the filter and an environment that simulates a vascular space in the first subchamber. Jointly or independently, a second flow of liquid can also be introduced into the second subchamber, and the second flow of liquid can be controlled so as to provide an environment that simulates a tissue space in the second subchamber. The fact that first flow of liquid and the second flow of liquid can be controlled independently from each other means, among other things, they can have different contents, different flow velocities, and/or different timing of flow.

Moreover, as such formed, the bioreactor allows growing and culture of multiple layers (or populations) of cells therein. In addition to the first layer of cells growing in the first subchamber, a second layer of cells is capable of growing in the second subchamber on the second surface side of the filter. The first layer of cells growing in the first subchamber and the second layer of cells growing in the second subchamber can be the same or different.

In yet another embodiment, an extension port member defining a channel therein is provided. As formed, the extension port member is positioned complimentarily to the port such that the channel of the extension port member is in fluid communication with the port and the first subchamber to allow the stream of substance to be directly introduced to the first subchamber.

In another embodiment, a bioreactor is provided with a first subchamber and a second subchamber, which are divided by a first filter, an extension port member and perfusion means in fluid communication with at least one of the first subchamber and the second subchamber to allow diffusional exchange of nutrients and metabolic byproducts with one or both the first subchamber and the second subchamber.

The perfusion means includes a second filter (or nanofilter), with a plurality of pores in fluid communication with the second subchamber, wherein the pores are sized to allow diffusional exchange of nutrients and metabolic byproducts with the second subchamber and not to allow cells to migrate across the second filter. The pores of the second filter, for example, can be sized to have a dimension smaller than 400 nanometers cross-sectionally. The first filter and the second filter can be the same or different.

The perfusion means further includes a perfusion supply network in fluid communication with the second filter through the pores. In one embodiment, the perfusion supply network includes a plurality of perfusion channels, each being in fluid communication with the second filter to allow bidirectional, diffusional exchange of nutrients and metabolic byproducts with the second filter and being dimensioned to minimize pressure drops along each perfusion channel and to allow passive diffusional exchange of nutrients and metabolic byproducts along each perfusion channel.

The perfusion supply network additionally includes a plurality of intermediate supply channels, each being in fluid communication with a plurality of corresponding perfusion channels so as to provide perfusate to the plurality of corresponding perfusion channels. Moreover, perfusion supply network includes a plurality of intermediate return channels, each being in fluid communication with a plurality of corresponding perfusion channels so as to collect perfusate from the plurality of corresponding perfusion channels.

Furthermore, the perfusion supply network includes a plurality of main supply channels, each being in fluid communication with a plurality of corresponding intermediate supply channels so as to provide perfusate to the plurality of corresponding intermediate supply channels, and a plurality of main return channels, each being in fluid communication with a plurality of corresponding intermediate return channels so as to collect perfusate from the plurality of corresponding intermediate return channels.

This type of bioreactor with a microfabricated transwell chamber with chemokine injection capability can be utilized to supported a coculture with filter perfusion to allow independent control of perfusion and shear in the chamber. The perfusion means maintains the viability of cells in the lower chamber independent of the flow in the upper chamber. Stream of substances affecting growth of cells such as chemotactic agents can be injected through dedicated ports in the perfusion means.

Optionally, at least one insertion member defining a cavity therein is provided. The insertion member has a length L and is positioned through the second substrate and into the tissue space such that the cavity of the insertion member is in fluid communication with the first subchamber or the vascular space.

Correspondingly, a plug having a first surface and an opposite second surface is provided. The plug is complimentary to a corresponding insertion member such that when the plug is received into the cavity of the corresponding insertion member, the plug engages with the body of the corresponding insertion member to seal the cavity and a volume is formed between the first surface and the first filter to allow a collection of cells to be received therein. For example, a collection of tumor cells can be contained in the volume. Optionally, a cage adapted for separating the tumor cells from the first subchamber can be utilized.

Additionally, the plug further defines a port in fluid communication with the volume for injecting or withdrawing a stream of substance affecting the growth of the tumor cells such as chemokine. Moreover, a plurality of electrodes adapted for electrochemical measurements of the tumor cells can be utilized together with the plug to form a metabolic sensing head.

In yet another alternative embodiment, a bioreactor is provided with an extension port member defining a channel therein. The extension port member is positioned such that the channel of the extension port member is in fluid communication with the first subchamber to allow a stream of substance to be introduced to the first subchamber or the vascular space. For example, a gradient of chemokine can be introduced into the first subchamber or the vascular space. A similar structure can be utilized to provide a stream of substance such as a gradient of chemokine to the tissue space.

These and other aspects of the present invention will become apparent from the following description of the preferred embodiment taken in conjunction with the following drawings, although variations and modifications therein may

BRIEF DESCRIPTION OF THE DRAWINGS

FIGS. 4A-B shows a bioreactor with a common feed line according to yet another embodiment of the present invention: 4A, a cross-sectional partial view, 4B, a cross-sectional side view along line A-A in FIG. 4A.

FIGS. 8A-D schematically show a top cross-sectional view of a bioreactor with a multi-chamber according to one embodiment of the present invention.

FIG. 9D1-3 show a layered perfusion system as shown in FIG. 9A: 9D1, a top cross-sectional view, 9D2, a side cross-sectional view along line B-B, 9D3, a side cross-sectional view along line A-A.

FIG. 9E1-2 shows an electron micrograph of a PS-b-PMMA film deposited on silicon: 9E1, at one magnification rate, 9E2, at another magnification rate.

FIGS. 9G1-G5 schematically show a fabrication process of the layered perfusion system as shown in FIG. 9A: 9G1, a side cross-sectional partial view of a silicon substrate, 9G2, step 1, etching channels 904c into the silicon wafer 953, 9G3, step 2, patterning the layer 951, 9G4, step 3, etching pores through the layer 952, 9G5, three views of the completed silicon substrate 950.

FIGS. 10A1-2 schematically show a bioreactor with multiple traps according to one embodiment of the present invention: 10A1, a perspective view; and 10A2, a perspective sectional view.

FIGS. 11A1-3 schematically show a bioreactor according to one embodiment of the present invention: 11A1, a top cross-sectional view; 11A2, a transverse cross-sectional view; and 11A3, a lateral cross-sectional view.

FIGS. 12A1-3 show a bioreactor with chemokine injection according to one embodiment of the present invention: 12A1, a top cross-sectional view, 12A2, a side cross-sectional view, 12A3, another side cross-sectional view.

DETAILED DESCRIPTION OF THE INVENTION

Figure 1A:
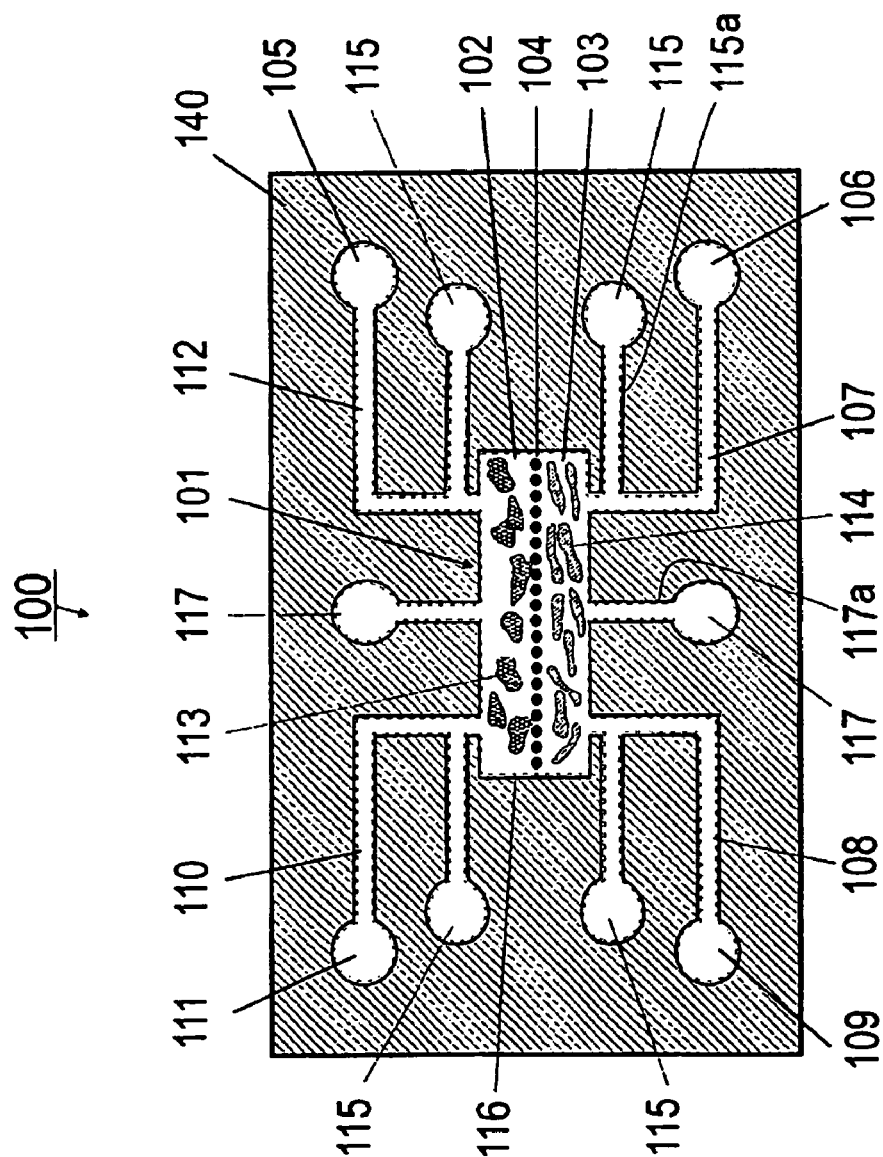
FIG. 1A schematically shows a top view of a bioreactor with a barrier according to one embodiment of the present invention.

Various embodiments of the invention are now described in detail. Referring to the drawings, like numbers indicate like parts throughout the views unless the context clearly dictates otherwise. As used in the description herein and throughout the claims that follow, the meaning of "a," "an," and "the" includes plural reference unless the context clearly dictates otherwise. Also, as used in the description herein and throughout the claims that follow, the meaning of "in" includes "in" and "on" unless the context clearly dictates otherwise. Additionally, some terms used in this specification are more specifically defined below.

DEFINITIONS

The terms used in this specification generally have their ordinary meanings in the art, within the context of the invention, and in the specific context where each term is used. For example, conventional techniques of molecular biology, microbiology and recombinant DNA techniques may be employed in accordance with the present invention. Such techniques and the meanings of terms associated therewith are explained fully in the literature. See, for example, Sambrook, Fitsch & Maniatis. Molecular Cloning: A Laboratory Manual, Second Edition (1989) Cold Spring Harbor Laboratory Press, Cold Spring Harbor, N.Y. (referred to herein as "Sambrook et al., 1989"); DNA Cloning: A Practical Approach, Volumes I and II (D. N. Glover ed. 1985); Oligonucleotide Synthesis (M. J. Gait ed. 1984); Nucleic Acid Hybridization (B. D. Hames & S. J. Higgins, eds. 1984); Animal Cell Culture (R. I. Freshney, ed. 1986); Immobilized Cells and Enzymes (IRL Press, 1986); B. E. Perbal, A Practical Guide to Molecular Cloning (1984); F. M. Ausubel et al. (eds.), Current Protocols in Molecular Biology, John Wiley & Sons, Inc. (1994). See also, PCR Protocols: A Guide to Methods and Applications, Innis et al., eds., Academic Press, Inc., New York (1990); Saiki et al., Science 1988, 239:487; and PCR Technology: Principles and Applications for DNA Amplification, H. Erlich, Ed., Stockton Press.

Certain terms that are used to describe the invention are discussed below, or elsewhere in the specification, to provide additional guidance to the practitioner in describing the devices and methods of the invention and how to make and use them. For convenience, certain terms are highlighted, for example using italics and/or quotation marks. The use of highlighting has no influence on the scope and meaning of a term; the scope and meaning of a term is the same, in the same context, whether or not it is highlighted. It will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification, including examples of any terms discussed herein, is illustrative only, and in no way limits the scope and meaning of the invention or of any exemplified term. Likewise, the invention is not limited to various embodiments given in this specification.

As used herein, "about" or "approximately" shall generally mean within 20 percent, preferably within 10 percent, and more preferably within 5 percent of a given value or range. Numerical quantities given herein are approximate, meaning that the term "about" or "approximately" can be inferred if not expressly stated.

The term "molecule" means any distinct or distinguishable structural unit of matter comprising one or more atoms, and includes for example polypeptides and polynucleotides.

As used herein, "cell" means any cell or cells, as well as viruses or any other particles having a microscopic size, e.g. a size that is similar to that of a biological cell, and includes any prokaryotic or eukaryotic cell, e.g., bacteria, fungi, plant and animal cells. Cells are typically spherical, but can also be elongated, flattened, deformable and asymmetrical, i.e., non-spherical. The size or diameter of a cell typically ranges from about 0.1 to 120 microns, and typically is from about 1 to 50 microns. A cell may be living or dead. As used herein, a cell is generally living unless otherwise indicated. As used herein, a cell may be charged or uncharged. For example, charged beads may be used to facilitate flow or detection, or as a reporter. Biological cells, living or dead, may be charged for example by using a surfactant, such as SDS (sodium dodecyl sulfate). Cell or a plurality of cells can also comprise cell lines. Example of cell lines include liver cell, macrophage cell, neuroblastoma cell, endothelial cell, intestine cell, hybridoma, CHO, fibroblast cell lines, red blood cells, electrically excitable cells, e.g. Cardiac cell, myocytes (AT1 cells), cells grown in co-culture, NG108-15 cells (a widely used neuroblastoma X glioma hybrid cell line, ATCC #HB-12317), primary neurons, a primary cardiac myocyte isolated from either the ventricles or atria of an animal neonate, an AT-1 atrial tumor cardiac cell, Liver cells are also known as Hepatocytes, Secretory cell (depolarize and it secretes things) pancreatic beta cells secrete insulin, HELA cells (Helen Lane), HEK293 Human Epithelial Kidney c, Erythrocytes (primary red blood cells), Lymphocytes and the like. Each cell line may include one or more cells, same or different. For examples, the liver cell comprises at least one of Human hepatocellular carcinoma ("HEPG2") cell, CCL-13 cell, and H4 IIE cell, the macrophage cells comprises at least one of peripheral blood mononuclear cells ("PBMC"), and skin fibroblast cells, the neuroblastoma cell comprises a U937 cell, the endothelial cell comprises a human umbilical vein-endothelial cell ("Huv-ec-c"), and the intestine cell comprises a CCL-6 cell.

"Culture" means a growth of living cells in a controlled artificial environment. It may be a culture of microorganisms, such as a bacterial culture, or one of animal or plant cells, such as a tissue culture. The bioreactors according to the invention can do both and more. Cultures require appropriate sources of food and energy, provided by the culture medium, and a suitable physical environment. Tissue cultures can themselves become a culture medium for viruses, which grow only with live cells. Cultures of only one kind of cells are known as pure cultures, as distinguished from mixed or contaminated cultures.

"Tissue" means an aggregation of cells more or less similar morphologically and functionally. The animal body is composed of four primary tissues, namely, epithelium, connective tissue (including bone, cartilage, and blood), muscle, and nervous tissue. The process of differentiation and maturation of tissues is called histogenesis.

A "sensor" is broadly defined as any device that can measure a measurable quantity. For examples, a sensor can be a thermal detector, an electrical detector, a chemical detector, an optical detector, an ion detector, a biological detector, a radioisotope detector, an electrochemical detector, a radiation detector, an acoustic detector, a magnetic detector, a capacitive detector, a pressure detector, an ultrasonic detector, an infrared detector, a microwave motion detector, a radar detector, an electric eye, an image sensor, any combination of them and the like. A variety of sensors can be chosen to practice the present invention.

The term "analyte" means a material that can be consumed or produced by a cell. Examples of analyte of interest include pH, K, oxygen, lactate, glucose, ascorbate, serotonin, dopamine, ammonia, glutamate, purine, calcium, sodium, potassium, NADH, protons, insulin, NO (nitric oxide) and the like.

The term "flow" means any movement of fluid such as a liquid or solid through a device or in a method of the invention, and encompasses without limitation any fluid stream, and any material moving with, within or against the stream, whether or not the material is carried by the stream. For example, the movement of molecules or cells through a device or in a method of the invention, e.g. through channels of a substrate on microfluidic chip of the invention, comprises a flow. This is so, according to the invention, whether or not the molecules or cells are carried by a stream of fluid also comprising a flow, or whether the molecules or cells are caused to move by some other direct or indirect force or motivation, and whether or not the nature of any motivating force is known or understood. The application of any force may be used to provide a flow, including without limitation, pressure, capillary action, electroosmosis, electrophoresis, dielectrophoresis, optical tweezers, and combinations thereof, without regard for any particular theory or mechanism of action, so long as molecules or cells are directed for detection, measurement or sorting according to the invention.

A "liquid or medium" is a fluid that may contain one or more substances that affecting growth of cells, one or more analytes, or any combination of them. A medium can be provided with one or more analytes to be consumed by one or more cells. A medium can have one or more analytes generated by one or more cells. A medium can also have at the same time one or more analytes to be consumed by one or more cells and one or more analytes generated by one or more cells. A medium may consist of natural materials, such as enzymatic digests, extracts of yeast or beef, milk, potato slices, or chick embryos. Artificial media are prepared by mixing various ingredients according to particular formulas. A complex medium contains at least one crude ingredient derived from a natural material, hence of unknown chemical composition. A chemically defined or synthetic medium is one in which the chemical structure and amount of each component are known.

An "inlet region" is an area of a bioreactor that receives molecules or cells or liquid. The inlet region may contain an inlet port and channel, a well or reservoir, an opening, and other features which facilitate the entry of molecules or cells into the device. A bioreactor may contain more than one inlet region if desired. The inlet region is in fluid communication with the channel and is upstream therefrom.

An "outlet region" is an area of a bioreactor that collects or dispenses molecules or cells or liquid. An outlet region is downstream from a discrimination region, and may contain outlet channels or ports. A bioreactor may contain more than one outlet region if desired.

An "analysis unit" is a microfabricated substrate, e.g., a microfabricated chip, having at least one inlet region, at least one channel and chamber, at least one detection region and at least one outlet region. A device of the invention may comprise a plurality of analysis units.

A "channel" is a pathway of a bioreactor of the invention that permits the flow of molecules or cells to pass a detection region for detection (identification), or measurement. The detection and discrimination regions can be placed or fabricated into the channel. The channel is typically in fluid communication with an inlet port or inlet region, which permits the flow of molecules or cells or liquids into the channel. The channel is also typically in fluid communication with an outlet region or outlet port, which permits the flow of molecules or cells or liquid out of the channel. The channel can also be used as a chamber to grown cells, and vice versa.

A "detection region" or "sensing volume" or "chamber" is a location within the bioreactor, typically in or coincident with the channel (or a portion thereof) and/or in or coincident with a detection loop, where molecules or cells to be grown, identified, characterized, hybridized, measured, analyzed or maintained (etc.), are examined on the basis of a predetermined characteristic. In one embodiment, molecules or cells are examined one at a time. In other embodiments, molecules, cells or samples are examined together, for example in groups, in arrays, in rapid, simultaneous or contemporaneous serial or parallel arrangements, or by affinity chromatography.

"Reaction time" is the time that a system of interest requires to respond to a change. For example, the reaction time of a cell is the time required for at least one of the physiological processes of a cell to adapt or respond to a change in its environment. Each type of cell has its own characteristic reaction time with respect to a particular change in its environment. The reaction time of a sensor is the time required for the sensor to respond to a change in the quantity that it is sensing. For example, the reaction time of an electrochemical sensor is set by the size of the sensor and the thickness and nature of protective coatings on the activated surfaces of the sensor. The reaction time of a microfluidic system is determined by, among other things, the reaction time of the cell to changes in the environment, the time required for chemical species to diffuse throughout the sensing volume, the reaction time of the sensor(s) and the diffusion time of the analyte being controlled by the actuators.

"Bacteria" are extremely small—usually 0.3-2.0 micrometers in diameter—and relatively simple microorganisms possessing the prokaryotic type of cell construction. Each bacterial cell arises either by division of a preexisting cell with similar characteristics, or through combination of elements from two such cells in a sexual process.

"Protozoa" means a group of eukaryotic microorganisms traditionally classified in the animal kingdom. Although the name signifies primitive animals, some Protozoa (phytoflagellates and slime molds) show enough plantlike characteristics to justify claims that they are plants. Protozoa range in size from 1 to $10^6$ micrometers. Colonies are known in flagellates, ciliates, and Sarcodina. Although marked differentiation of the reproductive and somatic zooids characterizes certain colonies, such as Volvox, Protozoa have not developed tissues and organs.

Several embodiments are now described with reference to the FIGS. 1-2, in which like numbers indicate like parts throughout the FIGS. 1-2.

OVERVIEW OF THE INVENTION

The inventors of the present invention overcome the disadvantages of the prior art and develop new bioreactors that have, among other new and inventive features, the capability of providing controlled chemokine gradients independent of the perfusion flow and allow extravasation of a cellular matrix. Recent advances in the fabrication of nanofilters[57-61] are used to create perfused-membrane bioreactors according to the present invention that allow the growth of mixed cultures of cells at near-to-tissue densities in 1 mm×1 mm×100 micron volumes, in the presence of controlled, stable chemokine or growth-factor gradients within the device, to mimic the in vivo tumor microenvironment.

One advantage of the present invention is that custom devices can be constructed such that the isolated perfusion and cell-delivery systems allow independent control of shear stress and chemokine gradients during the course of an experiment. Moreover, the optical and electrochemical metabolic microsensors can be installed within these bioreactors to allow simultaneous quantification of the local metabolic and chemical environment (lactate, pH, $O_2$, etc.) in selected regions within the reactor, while cell migration or cell signaling events are imaged by fluorescence microscopy. Hence, the bioreactors according to the present invention can be considered as the next generation of migration bioreactors that may move beyond a simple MicroTransWell (MTW) system to one that more closely replicates in vitro the microenvironment living tissue.

Moreover, the application of microfabrication techniques, microfluidics, and microbiosensors with the bioreactors according to the present invention offers an opportunity for study of the molecular mechanism of tumor angiogenesis as well as leukocyte and cancer cell extravasation. For example, the systematic examination of the role of Tie2 and VEGF in vascular formation and remodeling and may identify more specific molecular targets for anti-angiogenic therapy. A similar microdevice model could be used to examine leukocyte and cancer cell extravasation. These devices will provide an appropriate cellular environment to host mouse tumor explants, thereby potentially providing a metastasis assay for tumor biopsy material. Metabolic sensing in these bioreactors will help provide a clearer understanding of the tumor microenvironment and confirm the validity of our in vitro systems[62-65].

Additionally, the limitation of the planar Borenstein design that there is too little surface area of capillaries available to support the growth of a substantial volume of cells is overcome by the present invention, which remedies this problem by creating a multi-layer intercalated supply and return bioreactor that allows the full surface of a planar bioreactor to be covered with capillaries, and hence capillary-perfused cells.

More specifically, in one aspect, the present invention relates to bioreactors. These bioreactors are biomicroelectromechanical systems (BioMEMS) that serve as migration microenvironments to study molecular mechanisms of tumor angiogenesis, tumor metastasis and leukocyte migration, but can also function as more general tissue bioreactors and perfusion systems. Among other things, one unique aspect of these microfluidic devices is their integration of suitable cell culture and microfabrication techniques, which permit cell growth in small, confined, well-perfused volumes at tissue densities, provide independent control of multiple chemokines and growth factor gradients, shear forces, tissue perfusion, and permeability of physical barriers to cellular migration, and allow detailed optical and electrochemical observation of normal and cancerous cells during cell migration, intravasation, extravasation, angiogenesis, and other cellular processes.

Recent advances in the fabrication of nanofilters[57-61] can be used to practice the present invention to provide perfused-membrane bioreactors that can allow the growth of mixed cultures of cells at near-to-tissue densities in 1 mm×1 mm×100 micron volumes, in the presence of controlled, stable chemokine or growth-factor gradients within the device, to mimic the in vivo tumor microenvironment. One advantage of the present invention is that custom devices can be constructed such that the isolated perfusion and cell-delivery systems allow independent control of shear stress and chemokine gradients during the course of an experiment. Moreover, the optical and electrochemical metabolic microsensors can be installed within these bioreactors to allow simultaneous quantification of the local metabolic and chemical environment (lactate, pH, $O_2$, etc.) in selected regions within the reactor, while cell migration or cell signaling events are imaged by fluorescence microscopy. Hence the next generation of migration bioreactors will eventually move beyond a simple MicroTransWell (MTW) system to one that more closely replicates in vitro the microenvironment living tissue.

The application of microfabrication techniques, microfluidics, and microbiosensors offers an opportunity for study of the molecular mechanism of tumor angiogenesis as well as leukocyte and cancer cell extravasation. For example, the systematic examination of the role of Tie2 and VEGF in vascular formation and remodeling and may identify more specific molecular targets for anti-angiogenic therapy. A similar microdevice model could be used to examine leukocyte and cancer cell extravasation. These bioreactors will provide an appropriate cellular environment to host mouse tumor explants, thereby potentially providing a metastasis assay for tumor biopsy material. Metabolic sensing in these bioreactors will help provide a clearer understanding of the tumor microenvironment and confirm the validity of our in vitro systems[62-65].

Without intent to limit the scope of the invention, exemplary devices, application of them and related observations according to the embodiments of the present invention are given below. Note that titles or subtitles may be used in the examples for convenience of a reader, which in no way should limit the scope of the invention. Moreover, certain theories may have been proposed and disclosed herein; however, in no way they, whether they are right or wrong, should limit the scope of the invention so long as the devices and applications of them are practiced according to the invention without regard for any particular theory or scheme of action.

EXAMPLES

Bioreactor with One Barrier

Figure 1B:
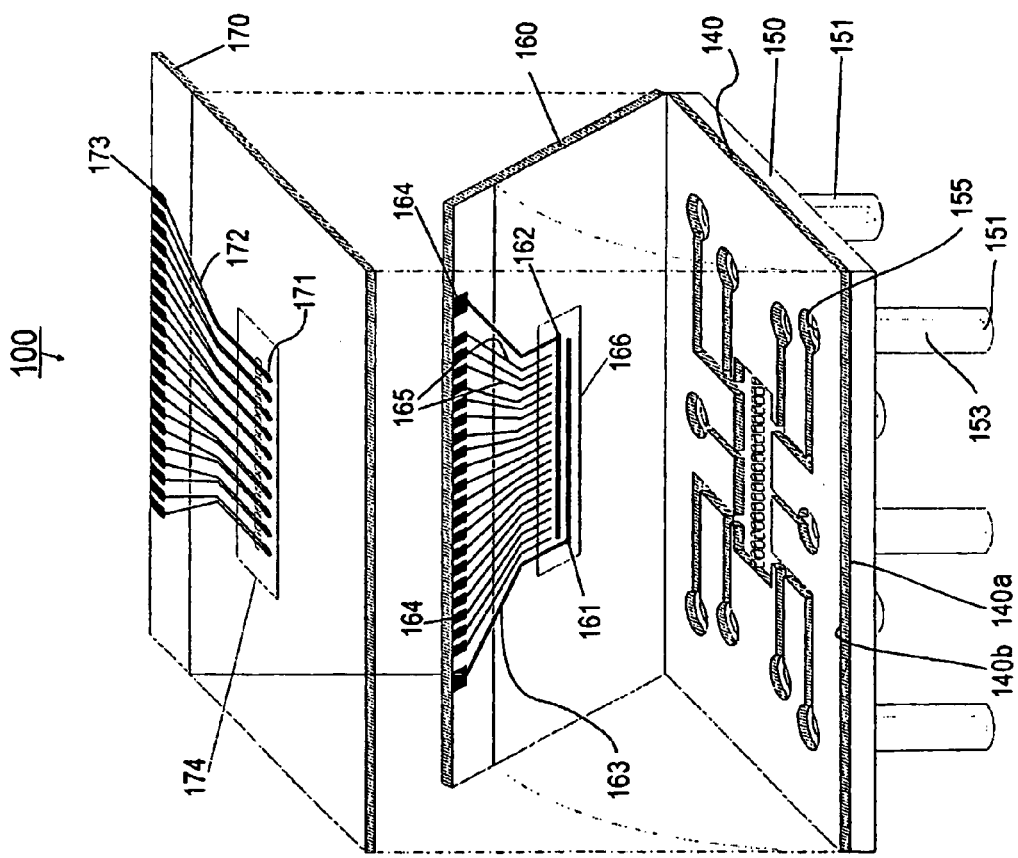
FIG. 1B shows a perspective view of a bioreactor with a barrier according to another embodiment of the present invention.

Referring now to FIGS. 1A and 1B, the present invention can be practiced in association with an inventive bioreactor 100 as shown in FIGS. 1A and 1B. In one embodiment, the bioreactor 100 includes a first substrate 140 having a first surface 140a and an opposite second surface 104b, defining a chamber 101 therebetween for receiving cells and a liquid medium. The bioreactor 100 has a barrier 104 dividing the chamber 101 into a first subchamber 102 and a second subchamber 103, wherein the barrier 104 has a porosity to allow the first subchamber 102 and the second subchamber 103 in fluid communication and allow at least one predetermined type of cells to permeate between the first subchamber 102 and the second subchamber 103. The porosity of the barrier 104 can also be chosen not to let any cells to permeate.

As formed, the first subchamber 102 is adapted for receiving a first type of material such as cells 113 and the second subchamber 103 is adapted for receiving a second type of material such as cells 114, wherein each of the first type of material and the second type of material contains at least one selected from the group of cells, chemicals, and fluids. The cells can be any type of living cells, including, but not limited to, bacteria, protozoa, or both, normal cells, tumor cells, or any combination of them.

A biocompatible coating layer 116 can be applied to the chamber walls of the bioreactor 100, wherein the biocompatible coating layer 116 includes a material that may inhibit cell adhesion to the biocompatible coating layer, enhance cell adhesion to the biocompatible coating layer, or function as a fluorescent marker or indicator of the state of cells.

The bioreactor 100 further includes at least one or more inlet ports 105, 106 and one or more corresponding input transfer channel 112, 107. As formed, the input transfer channel 112 is in fluid communication with the corresponding inlet port 105 and the first subchamber 102, and the input transfer channel 107 is in fluid communication with the corresponding inlet port 106 and the second subchamber 103 for allowing delivery of the cells, fluids or chemicals to the corresponding subchamber 102 or 103, respectively. For example, a fluid can be introduced from an external device (not shown) into the first subchamber 102 through the inlet port 105 and the corresponding input transfer channel 112. Inlet ports 105, 106 each can be in fluid communication with an external device or port (not shown).

The bioreactor 100 additionally includes at least one or more outlet ports 111, 109 and one or more corresponding outlet transfer channel 110, 108. As formed, the outlet transfer channel 110 is in fluid communication with the corresponding outlet port 111 and the first subchamber 102, and the outlet transfer channel 108 is in fluid communication with the corresponding outlet port 109 and second subchamber 103 for allowing removal of the cells, fluids or chemicals from the corresponding subchamber 102 or 103, respectively. For example, a fluid can be introduced away from the first subchamber 102 through the outlet transfer channel 110 and the corresponding outlet port 111. Outlet ports 111, 109 each can be in fluid communication with an external device or port (not shown).

The bioreactor 100 further includes at least one or more auxiliary ports 115 and one or more auxiliary channels 115a. As formed, each auxiliary channel 115a is in fluid communication with a corresponding auxiliary port 115 and a corresponding one of the input transfer channels 112, 107 and the outlet transfer channels 110, 108 for flushing the corresponding transfer channel. Auxiliary ports 115 each can be in fluid communication with an external device or port (not shown). Auxiliary ports 115 and auxiliary channels 115a can be utilized to prevent clogging by cells or cellular debris in the bioreactor 100. They can also be utilized to selectively apply coatings to the channels to which they are in fluid communication.

The bioreactor 100 additionally includes one or more access ports 117 and one or more access channels 117a. As formed, each access channel 117a is in fluid communication with a corresponding access port 117 and a corresponding one of the first subchamber 102 and the second subchamber 103 for allowing delivery or removal of the cells, fluids, chemicals, coating material or sensing material to the corresponding subchamber. The access ports 117 and corresponding access channels 117a are strategically positioned so as to provide direct access to the first subchamber 102 and the second subchamber 103. For example, a fluid can be introduced into the first subchamber 102 through an access channels 117a and the corresponding access port 117 fast because the distance between the access port 117 and the first subchamber 102 is the shortest for this embodiment. Each access port 117 can be in fluid communication with an external device or port (not shown).

Moreover, the bioreactor 100 has a second substrate 150, wherein the second substrate 150 is positioned adjacent to the first surface 140a of the first substrate 140 and defines a plurality of connection channels 155. Each of the connection channels 155 is formed so as to be in fluid communication with a corresponding one of the inlet ports 105, 106, the outlet ports 111, 109, the auxiliary ports 115, and the access ports 117 as set forth above.

The bioreactor 100 further includes a plurality of connection ports 151 corresponding to the plurality of connection channels 155. Each of the connection ports 151 is formed with a channel 153 and is strategically positioned to the second substrate 150 such that each channel 153 of the connection ports 151 is in fluid communication with a corresponding one of the connection channels 155 formed in the second substrate 150 as shown in FIG. 1B.

The first substrate 140 can be fabricated from glass, Mylar, PDMS, silicon, a polymer, a semiconductor, or any combination of them. The barrier 104 is formed with a porous material. The barrier 104 can be microfabricated so as to form a structure allowing the fluid communication between the first subchamber 102 and the second subchamber 103, which may allow permeation of the barrier 104 by certain predetermined types of cells but not by other types of cells. For example, in the embodiment shown in FIGS. 1A and 1B, the barrier 104 is formed with a plurality of posts spaced from each other so as to allow bacteria to cross over but not protozoa.

The bioreactor 100 further has a third substrate 160, which is positioned adjacent to the first surface of the first substrate 140, and means strategically positioned in the third substrate 160 and adapted for electrochemical measurements of the cells responsive to the liquid medium in one or both of the first subchamber 102 and the second subchamber 103. The third substrate 160 can be formed with a semiconductor material such as silicon.

In one embodiment as shown in FIG. 1B, the means for electrochemical measurements includes a reference electrode 161, a counter electrode 162, a plurality of edge connector pads 164, and a plurality of electrically conductive leads 163. A first electrically conductive lead 163 electrically couples the reference electrode 161 to a corresponding edge connector pad 164, and a second electrically conductive lead 163 electrically couples the counter electrode 162 to a corresponding edge connector pad 164. The means for electrochemical measurements further includes a plurality of individually addressable working electrodes 165. Each of the plurality of individually addressable working electrodes 165 is electrically coupled to a corresponding edge connector pad 164 through a corresponding electrically conductive lead 163. The sensing heads of the plurality of individually addressable working electrodes 165 are strategically positioned in a region shown by outline 166 in FIG. 1B.

In operation, the liquid medium being introduced into one or both of the first subchamber 102 and the second subchamber 103 may include one or more analytes, and the plurality of individually addressable working electrodes are adapted for sensing the concentration of a single analyte of the liquid medium at multiple locations in the chamber 101 or the concentrations of a plurality of analytes of the liquid medium at multiple locations in the chamber 101 at a time period shorter than a characteristic reaction time related to at least one of cellular physiological activities of the cells. The plurality of individually addressable working electrodes can be further adapted to be capable of measuring the metabolic variables related to the cells responsive to the liquid medium at multiple locations in the chamber 101 at a time period shorter than a characteristic reaction time related to at least one of cellular physiological activities of the cells. The sensing heads of the plurality of individually addressable working electrodes 165 are strategically positioned in a region shown by outline 166 corresponding to that of the chamber 101 to perform such tasks.

The bioreactor 100 further includes a fourth substrate 170, wherein the fourth substrate 170 is positioned above the second surface 140b of the first substrate 140, and means strategically positioned in the fourth substrate 170 and adapted for optical measurements of the cells responsive to the liquid medium in at least one of the first subchamber 102 and the second subchamber 103. The fourth substrate 170 is at least partially transparent. For examples, it can be formed with a semiconductor material or a glass or both.

In one embodiment as shown in FIG. 1B, the means for optical measurements includes a plurality of optical sensors 171, a plurality of edge connector pads 173, and a plurality of leads 172, each coupling an optical sensor 171 to a corresponding edge connector pad 173. The plurality of optical sensors 171 may include at least one device selected from the group of an LED and photodiode pair, a fiber optic coupler, and an optical detecting head.

In operation, the liquid medium being introduced into one or both of the first subchamber 102 and the second subchamber 103 may include one or more analytes, and the plurality of optical sensors 171 are adapted to be capable of sensing the concentration of a single analyte of the liquid medium at multiple locations in the chamber 101 or the concentrations of a plurality of analytes of the liquid medium at multiple locations in the chamber 101 at a time period shorter than a characteristic reaction time related to at least one of cellular physiological activities of the cells. The plurality of optical sensors 171 can be further adapted for measuring the metabolic variables related to the cells responsive to the liquid medium at multiple locations in the chamber 101 at a time period shorter than the characteristic reaction time related to at least one of cellular physiological activities of the cells. The sensing heads of the plurality of optical sensors 171 are strategically positioned in a region shown by outline 174 corresponding to that of the chamber 101 to perform such tasks.

Bioreactor with Multiple Barriers

Referring now to FIG. 2, the present invention can also be practiced in association with an inventive bioreactor 700 as shown in FIG. 2. In one embodiment, the bioreactor 700 includes a substrate 730 having a first surface and an opposite second surface, defining a chamber 732 therebetween for receiving cells and a liquid medium, wherein the chamber 732 is formed with a center 734 and a boundary 736. The bioreactor 700 also has a first barrier 738, which encloses the center 734 and a portion of the chamber 732 to form a central chamber 706, and a second barrier 740, which is positioned between the first barrier 738 and the boundary 736 so as to form an intermediate chamber 705 and an outer chamber 704.

In one embodiment, the first barrier 738 has a first porosity to allow the central chamber 706 and the intermediate chamber 705 in fluid communication and allow at least a first predetermined type of cells to permeate between the central chamber 706 and the intermediate chamber 705, and the second barrier 740 has a second porosity to allow the outer chamber 704 and the intermediate chamber 705 in fluid communication and allow at least a second predetermined type of cells to permeate between the outer chamber 704 and the intermediate chamber 705.

Moreover, the central chamber 706 is adapted for receiving a first type of material such as tumor cells 714, the intermediate chamber 705 is adapted for receiving a second type of material such as normal tissue cells 713, and the outer chamber 704 is adapted for receiving a third type of material such as endothelial cells 712. Each of the first type of material, the second type of material and the third type of material contains at least one selected from the group of cells, chemicals, and fluids.

The first predetermined type of cells includes tumor cells 714, which normally is received in the central chamber 706 that is formed to simulate a tumor space. The second predetermined type of cells includes normal tissue cells 713, which normally is received in the intermediate chamber 705 that is formed to simulate a tissue space. Furthermore, the outer chamber 704 is formed to simulate a vascular space adapted for receiving endothelial cells, macrophage cells, neutrophil cells, any combination of them, or other immune cell type.

A biocompatible coating layer 742 can be applied to the chamber walls at the boundary 736, wherein the biocompatible coating layer 742 includes a material that may inhibit cell adhesion to the biocompatible coating layer, enhance cell adhesion to the biocompatible coating layer, or function as a fluorescent marker or indicator of the state of cells.

The bioreactor 700 further includes one or more inlet or outlet ports 701 and corresponding one or more input or output transfer channels 751, where each of the input or output transfer channel 751 is in fluid communication with a corresponding inlet or outlet port 701 and the outer chamber 704 for allowing delivery of cells, fluids or chemicals to the outer chamber 704.

The bioreactor 700 additionally may include one or more inlet or outlet ports 702 and corresponding one or more input or output transfer channels 752, where each of the input or output transfer channels 752 is in fluid communication with a corresponding inlet or outlet port 702 and the central chamber 706 for allowing delivery of the cells, fluids or chemicals to the central chamber 706.

The bioreactor 700 may further include one or more inlet or outlet ports 703 and corresponding one or more input or output transfer channels 753, where each of the input or output transfer channels 753 is in fluid communication with a corresponding inlet or outlet port 703 and the intermediate chamber 705 for allowing delivery of the cells, fluids or chemicals to the intermediate chamber 705.

The substrate 730 can be fabricated from glass, Mylar, PDMS, silicon, a polymer, a semiconductor, or any combination of them. The first barrier 738 is formed with a porous material. The first barrier 738 can be microfabricated so as to form a first structure allowing the fluid communication between the central chamber 706 and the intermediate chamber 705. The second barrier 740 is formed with a porous material. The second barrier 740 can be microfabricated so as to form a second structure allowing the fluid communication between the outer chamber 704 and the intermediate chamber 705. The first barrier 738 and the second barrier 740 can be formed with same or different porous materials. And the second structure can be same or different from the first structure. For example, in the embodiment shown in FIG. 2, the first barrier 738 is formed with a plurality of posts spaced from each other more condensed than the second barrier 740. The first barrier 738 and the second barrier 740 can also be formed into same or different shapes. For example, in the embodiment shown in FIG. 2, the first barrier 738 and the second barrier 740 are substantially circular. The boundary 736 can take various geometric shapes as well. For example, in the embodiment shown in FIG. 2, the boundary 736 is substantially circular.

The bioreactor 700 further includes means strategically positioned and adapted for electrochemical measurements of the cells responsive to the liquid medium in one or more of the outer chamber 704, the intermediate chamber 705 and the central chamber 706.

In one embodiment as shown in FIG. 2, the means for electrochemical measurements includes a reference electrode 707, a counter electrode 708, and a plurality of individually addressable working electrodes.

In operation, the liquid medium being introduced into one or more of the outer chamber 704, the intermediate chamber 705 and the central chamber 706 may include one or more analytes, and the plurality of individually addressable working electrodes include a first group of individually addressable working electrodes 709, a second group of individually addressable working electrodes 710 and a third group of individually addressable working electrodes 711, respectively.

For the embodiment shown in FIG. 2, the first group of individually addressable working electrodes 709 are adapted to be capable of sensing the concentration of a single analyte of the liquid medium at multiple locations in the outer chamber 704 or the concentrations of a plurality of analytes of the liquid medium at multiple locations in the outer chamber 704 at a time period shorter than a characteristic reaction time related to at least one of cellular physiological activities of the cells. The first group of individually addressable working electrodes 709 are further adapted to be capable of measuring the metabolic variables related to the cells responsive to the liquid medium at multiple locations in the outer chamber 704 at a time period shorter than a characteristic reaction time related to at least one of cellular physiological activities of the cells.

The second group of individually addressable working electrodes 710 adapted to be capable of sensing the concentration of a single analyte of the liquid medium at multiple locations in the central chamber 706 or the concentrations of a plurality of analytes of the liquid medium at multiple locations in the central chamber 706 at a time period shorter than a characteristic reaction time related to at least one of cellular physiological activities of the cells. The second group of individually addressable working electrodes 710 are further adapted to be capable of measuring the metabolic variables related to the cells responsive to the liquid medium at multiple locations in the central chamber 706 at a time period shorter than a characteristic reaction time related to at least one of cellular physiological activities of the cells.

Similarly, the third group of individually addressable working electrodes 711 are adapted to be capable of sensing the concentration of a single analyte of the liquid medium at multiple locations in the intermediate chamber 705 or the concentrations of a plurality of analytes of the liquid medium at multiple locations in the intermediate chamber 705 at a time period shorter than a characteristic reaction time related to at least one of cellular physiological activities of the cells. The third group of individually addressable working electrodes 711 are further adapted to be capable of measuring the metabolic variables related to the cells responsive to the liquid medium at multiple locations in the intermediate chamber 705 at a time period shorter than a characteristic reaction time related to at least one of cellular physiological activities of the cells.

As such formed, among other things, bioreactor 700 can be utilized to nurture, culture, observe, detect and explore cells, collection of cells, biofilm formed by cells and related cell activities. For examples, as shown in FIG. 2, bioreactor 700 allows a spectrum of cell activities to take place, including: a cell 715, which can be an immune type of cell such as a macrophage or neutrophil, undergoing extravasation across the second barrier 740 from the outer chamber 704 into the intermediate chamber 705, a cell 716, which can be a tumor cell metastasizing from the central chamber 706 through the surrounding tissue into the vascular space, undergoing intravasation across the second barrier 740 from the intermediate chamber 705 into the outer chamber 704, and a cell 717, for example, an endothelial cell, undergoing tube formation across the second barrier 740 that may eventually lead to vascularization of the tumor, respectively.

Bioreactors with an Array of Chambers and a Common Feed Line

Referring now to FIGS. 2-6, the present invention can be practiced in association with an inventive bioreactor 200 as shown in FIGS. 2-6. In one embodiment, referring first to FIGS. 2A and 2B, the bioreactor 200 includes a substrate 230 having a first surface and an opposite second surface. The bioreactor 200 has a plurality of array of chambers 204 formed on the substrate 230. Each array of chambers 204 is adapted for receiving cells in a liquid medium and includes a channel 202 and a plurality of chambers 206 formed in the substrate 230. Each of the plurality of chambers 206 is adapted for receiving cells in a liquid medium and formed with an open end 262, an opposite closed end 264 and sidewalls 266. The open end 262 and the closed end 264 of a particular chamber 206 define a depth, d, therebetween for the corresponding chamber 206, which is in fluid communication with the channel 202 through the open end 262. Additionally, the sidewalls 266 defines a width, w, therebetween for the corresponding chamber 206. As formed, at least two of the plurality of chambers 206, either from same array or different arrays, may have depths or widths same or different from each other. This design allows the bioreactor 200 to provide a variety of environments to cells tailored for different applications. The substrate 230 can be fabricated from glass, Mylar, PDMS, silicon, a polymer, a semiconductor, or any combination of them.

Each array of chambers 204 may further includes an inlet port 201 formed in fluid communication with the channel 202, and an outlet port 203 formed in fluid communication with the channel 202, wherein the inlet port 201 and the outlet port 203 are apart from each other along the channel 202. As such formed, a fluid or an intended amount of material such as a bolus of selected chemicals 206 can be introduced from an external device or port (not shown) into the channel 202 through the inlet port 201, and away from the channel 202 through the outlet port 203. Thus, to each array 204, channel 202 serves as a common feed line to the plurality of chambers 206.

Each of the plurality of chambers 206 is adapted to receive and culture at least one predetermined type of cells. The cells can be any type of living cells, including, but not limited to, bacteria, protozoa, or both, normal cells, tumor cells, or any combination of them. Cells can be introduced into a chamber individually, in a collection of cells, or in the form of biofilms. Different chambers can have same or different types of cells.

Figures 2A, 2B:
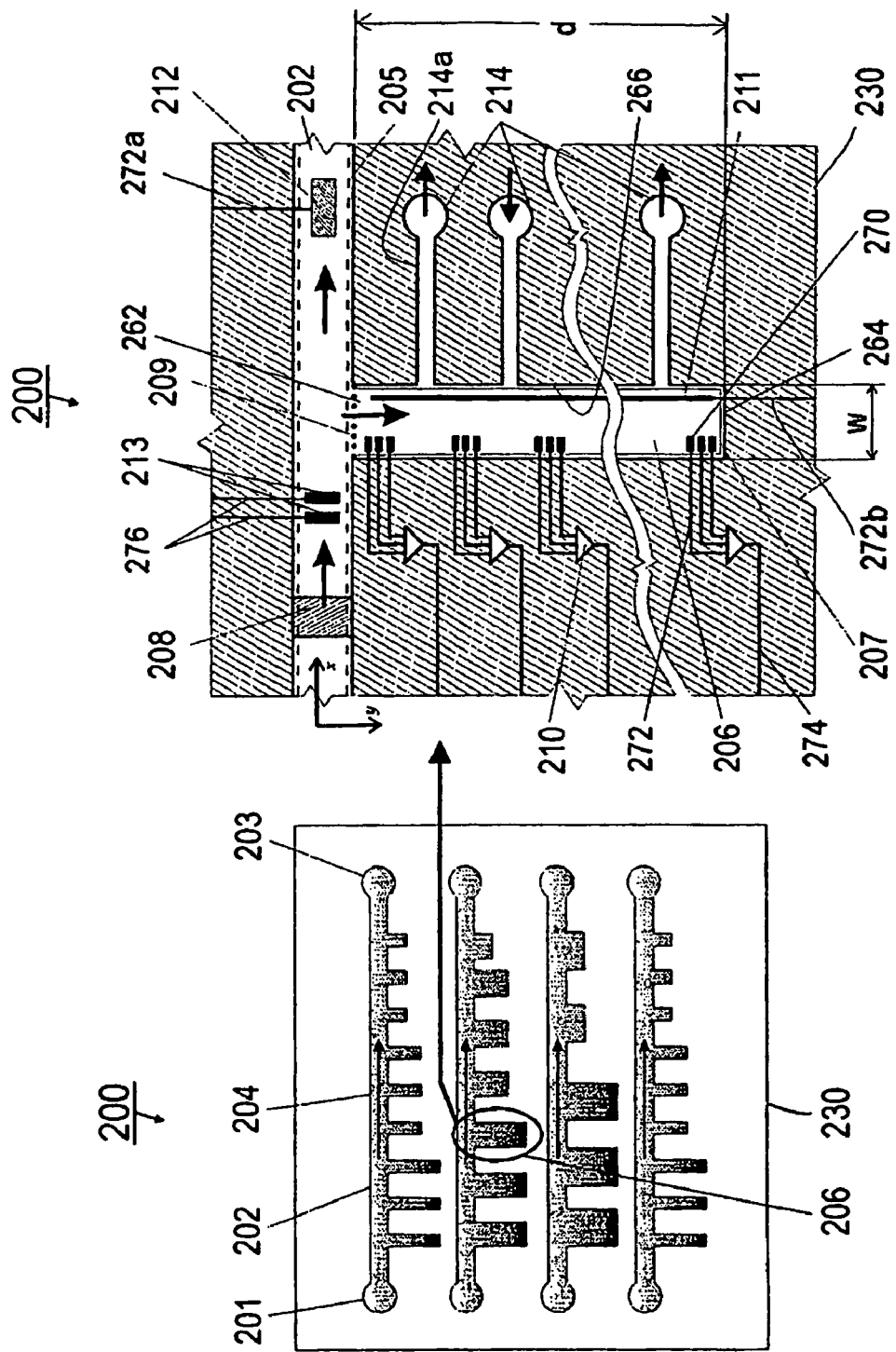
FIG. 2A schematically shows a bioreactor with a common feed line according to one embodiments of the present invention.
FIG. 2B shows a cross-sectional partial view of a bioreactor as shown in FIG. 1A.

The bioreactor 200 further includes a barrier 209 for at least one of the chambers 206, wherein the barrier 209 is positioned substantially at the open end 262 of a corresponding chamber 206 as shown in FIG. 2B. The barrier 209 has a porosity to allow the corresponding chamber 206 and the channel 202 in fluid communication to each other. The barrier 209 also allows at least one predetermined type of cells to permeate between the corresponding chamber 206 and the channel 202 and at least another predetermined type of cells not to permeate between the corresponding chamber 206 and the channel 202. The barrier 209 can also allows no cells to permeate at all. Thus, the barrier 209 has a selective porosity for the cells and functions as a filter as well.

The bioreactor 200 also includes a biocompatible coating layer 205 applied to the channel walls, wherein the biocompatible coating layer 205 comprises a material that may inhibit cell adhesion to the biocompatible coating layer to keep the fluid communication in the channel 202 open. Alternatively, in place of the biocompatible coating layer 205, other means such as a leaky light guide can be utilized.

The bioreactor 200 may further include a biocompatible coating layer 207 applied to the sidewalls 266 of a chamber 206. The biocompatible coating layer 207 comprises a material that may inhibit cell adhesion to the biocompatible coating layer 207, enhance cell adhesion to the biocompatible coating layer 207, or function as a fluorescent marker or indicator of the state of cells. Different chambers 206 may have same or different coating layers.

The bioreactor 200 further includes at least one or more auxiliary ports 214 and corresponding auxiliary channels 214a. As formed, an auxiliary channel 214a is in fluid communication with a corresponding auxiliary port 214 and a corresponding chamber 206 for allowing individual control of the environment of the corresponding chamber 206. The individual control of the environment of the corresponding chamber 206 includes any and all intended activities that may affect the environment of a chamber such as the delivery or removal of the cells, fluids or chemicals to the corresponding chamber 206 or flushing the corresponding chamber 206.

Figure 3:
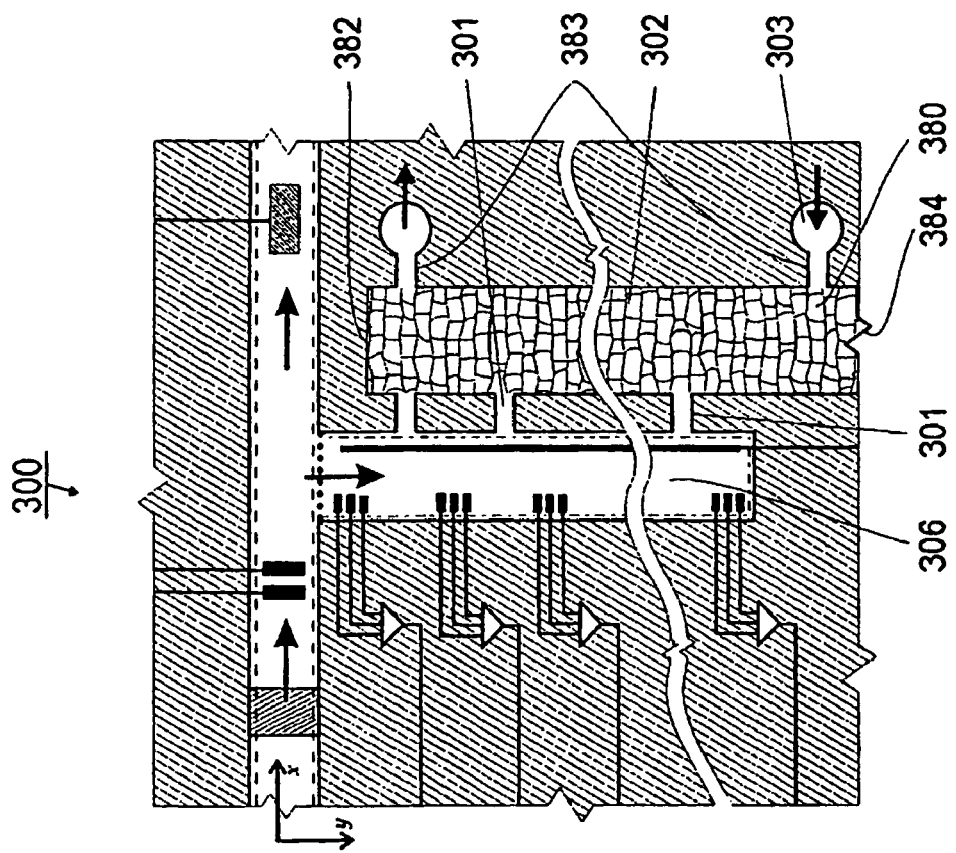
FIG. 3 shows a cross-sectional partial view of a bioreactor with a common feed line according to another embodiment of the present invention.

In an alternative embodiment as shown in FIG. 3, a bioreactor 300 includes at least one sample chamber 302 and a plurality of sample channels 301, wherein the plurality of sample channels 301 are in fluid communication with the sample chamber 302 and a corresponding chamber 306. As formed, the sample chamber 302 is in fluid communication with at least one corresponding auxiliary channel 383 that is in fluid communication with at least one corresponding auxiliary port 303, for allowing individual control of the environment of the corresponding sample chamber 302. The individual control of the environment of the corresponding sample chamber 302 includes any and all intended activities that may affect the environment of a sample chamber 302 such as the delivery or removal of the fluids, or materials, or substance such as chemicals to the corresponding sample chamber 302. The sample chamber 302 is further adapted for receiving a sample 380 of host material, such as soil, that provides exudates affecting the cells or biofilm in the corresponding chamber 306. The sample chamber 302 is also formed with a closed end 382 and an opposite open end 384 through which the host material can be received into or removed from the sample chamber 302. Additionally, a lid (not shown) adapted for slidably covering or opening the open end 384 of the sample chamber 302 can be utilized. This type of the bioreactor according to the embodiment of the present invention in FIG. 3 allows one to, among other things, observe, detect, adjust, control, and/or utilize the effects of exudates from a sample of host material on the cells growing in the chamber of the bioreactor.

Figure 5:
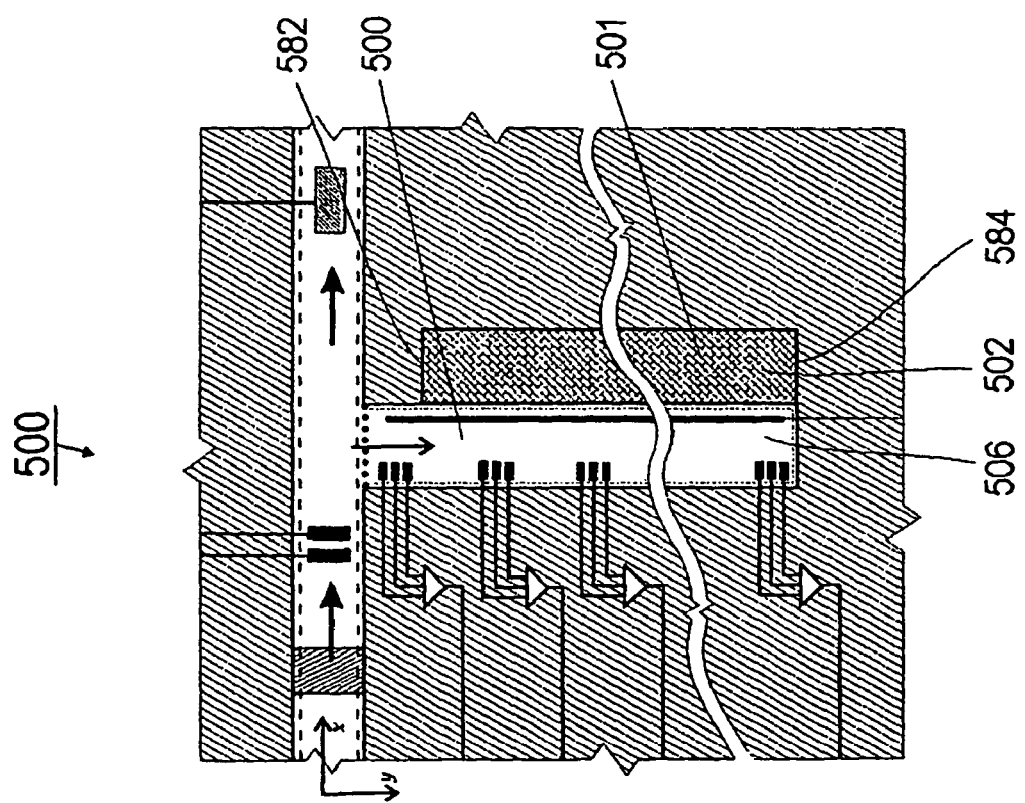
FIG. 5 shows a cross-sectional partial view of a bioreactor with a common feed line according to a further embodiment of the present invention.

In another alternative embodiment as shown in FIG. 5, a bioreactor 500 includes at least one sample chamber 502 that is formed in fluid communication with a corresponding chamber 506. The sample chamber 502 is adapted for receiving a sample of host material 501 that can directly affect the cells or biofilm in the corresponding chamber 506 because the sample chamber 502 is directly in fluid communication with a corresponding chamber 506. The sample chamber 502 is formed with a closed end 582 and an opposite open end 584 through which the sample of host material 501 can be received into or removed from the sample chamber 502. Additionally, a lid (not shown) adapted for slidably covering or opening the open end 584 of the sample chamber 502 can be utilized. This type of the bioreactor according to the embodiment of the present invention in FIG. 5 allows one to, among other things, observe, detect, adjust, control, and/or utilize the effects of a sample of host material on the cells growing in the chamber of the bioreactor.

The bioreactor 200 additionally includes, referring now to FIGS. 2A and 2B, means adapted for electrochemical measurements of the cells responsive to the liquid medium in at least one of the chambers 206. In one embodiment, the means for electrochemical measurements includes a counter electrode 211, a reference electrode 212, and a plurality of electrically conductive leads. Among the plurality of electrically conductive leads, a first electrically conductive lead 272a electrically couples the reference electrode 212 to a corresponding edge connector pad (not shown), and a second electrically conductive lead 272b electrically couples the counter electrode 211 to a corresponding edge connector pad (not shown). The means for electrochemical measurements can also be used to measure the electrochemical constituents outside the cells that reflect the status of the cells, the culture medium, or the cellular exudates.

The means for electrochemical measurements further includes a plurality of individually addressable working electrodes 270 and a plurality of corresponding amplifiers 210. Each individually addressable working electrode 270 is electrically coupled to a corresponding amplifier 210 through a corresponding electrically conductive lead 272. The bioreactor 200 further includes a plurality of electrically conductive output leads 274, each electrically coupling a corresponding amplifier 210 to an output device such as a multiplexed potentiostat (not shown).

In operation, the liquid medium being introduced into an array 204 through a corresponding channel 202 (and into one or more chambers 206) may include one or more analytes, and the plurality of individually addressable working electrodes 270 are adapted for capable of sensing the concentration of a single analyte of the liquid medium at multiple locations in a corresponding chamber 206 or the concentrations of a plurality of analytes of the liquid medium at multiple locations in the corresponding chamber 206 at a time period shorter than a characteristic reaction time related to at least one of cellular physiological activities of the cells. The plurality of individually addressable working electrodes 270 are further adapted for capable of measuring the metabolic variables related to the cells responsive to the liquid medium at multiple locations in the corresponding chamber 206 at a time period shorter than a characteristic reaction time related to at least one of cellular physiological activities of the cells.

Alternatively, as shown in FIG. 4, a bioreactor 400 has a plurality of controlling ports 404 and a plurality of connection channels 494, wherein each of the connection channels 494 is in fluid communication with a corresponding controlling port 404 and a chamber 496. The bioreactor 400 further includes a fluid control valve 402 adapted for controlling the fluid communication between the plurality of controlling ports 404 and the chamber 496, wherein the fluid control valve 402 includes a pneumatic or mechanical valve. A control port 401 adapted for controlling the fluid control valve 402 can also be provided.

In this embodiment, the counter electrode 405 and the reference electrode 406 are positioned between the fluid control valve 402 and the plurality of controlling ports 404, wherein the liquid medium includes at least one or more analytes, and wherein the plurality of individually addressable working electrodes are positioned between the fluid control valve 402 and the plurality of controlling ports 404 and adapted for capable of sensing the concentration of a single analyte of the liquid medium corresponding to multiple locations in a corresponding chamber 496 or the concentrations of a plurality of analytes of the liquid medium corresponding to multiple locations in the corresponding chamber 496 at a time period shorter than a characteristic reaction time related to at least one of cellular physiological activities of the cells. The plurality of individually addressable working electrodes are further adapted for capable of measuring the metabolic variables related to the cells responsive to the liquid medium at multiple locations corresponding to the corresponding chamber 496 at a time period shorter than a characteristic reaction time related to at least one of cellular physiological activities of the cells. This type of the bioreactor according to the embodiment of the present invention in FIG. 4 allows one to, among other things, minimize disturbances such as biofouling of the sensors to the cells in the chamber because the sensors are physically separated from the chamber of the bioreactor.

Figure 6:
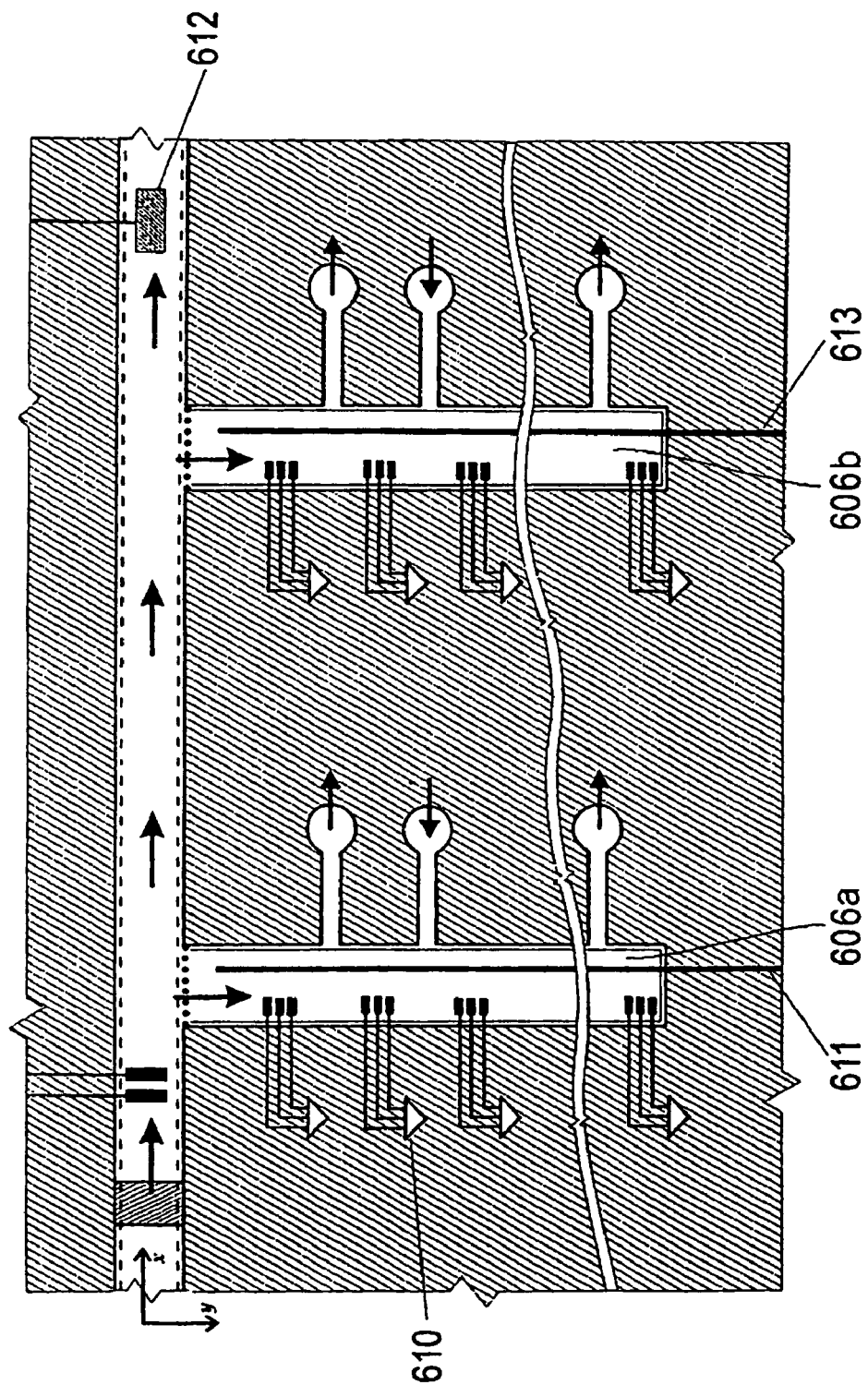
FIG. 6 shows a cross-sectional partial view of a bioreactor with a common feed line according to a yet another single-array embodiment of the present invention.
Figure 7:
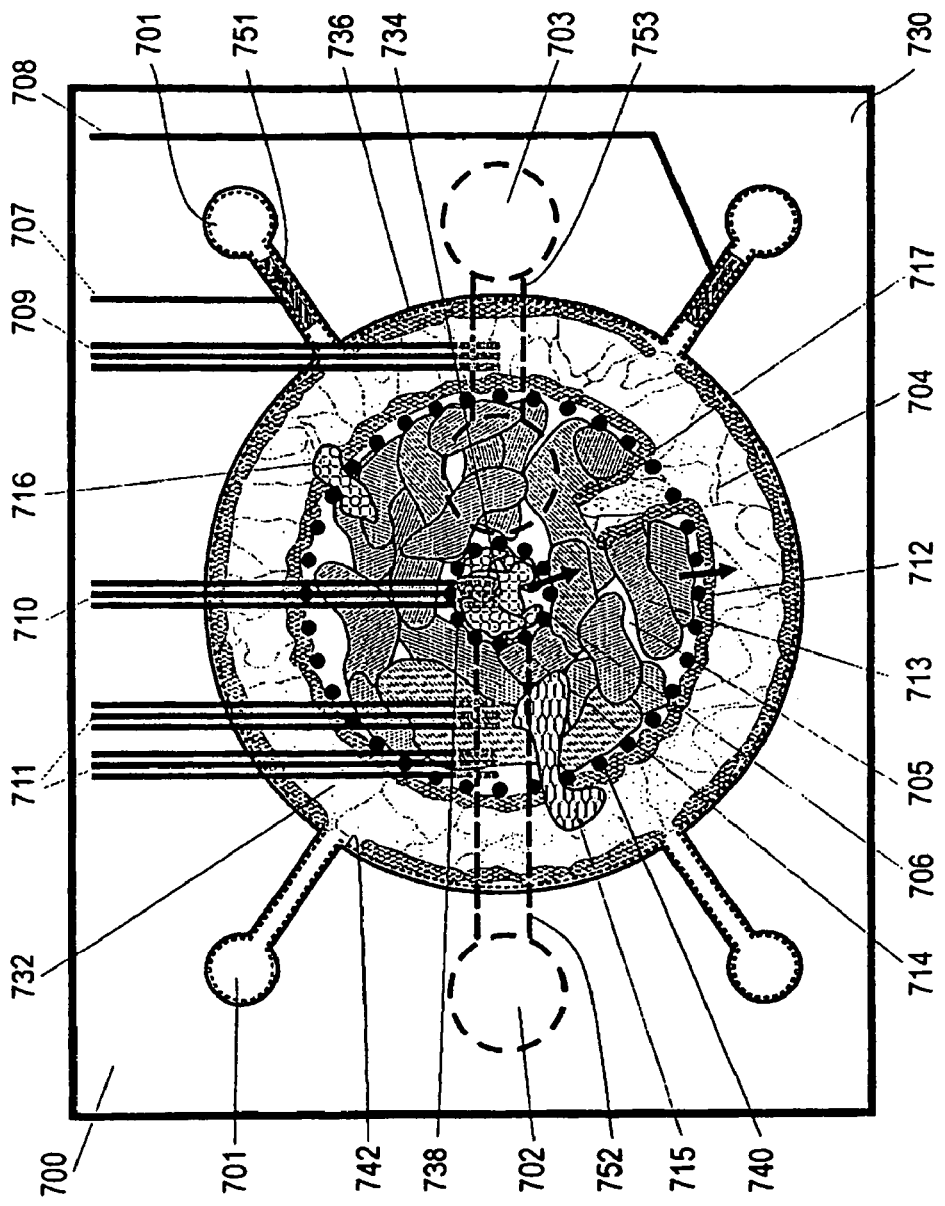
FIG. 7 schematically shows a top view of a bioreactor with two barriers according to one embodiment of the present invention.

In another embodiment as shown in FIG. 6, the reference electrode 612 can be strategically positioned as a common reference electrode and adapted for electrochemical measurements of the cells responsive to the liquid medium in the plurality of chambers. Correspondingly, in each of the plurality of chambers, a counter electrode is adapted for electrochemical measurements of the cells responsive to the liquid medium in a corresponding chamber to allow the plurality of chambers to be operated individually and the means for electrochemical measurements for the plurality of chambers to be activated for one or more chambers at a time sequentially. For examples, a counter electrode 611 is adapted for electrochemical measurements of the cells responsive to the liquid medium in a corresponding chamber 606a, and a counter electrode 613 is adapted for electrochemical measurements of the cells responsive to the liquid medium in a corresponding chamber 606a, respectively.

The bioreactor of this invention further includes means positioned in the channel and adapted for monitoring of the cells therein optically, electrically or both. In one embodiment as shown in FIGS. 2A and 2B, the means for monitoring of the cells can include at least one optical sensor 213 and at least one lead 276 in optical communication with a corresponding optical sensor 213. The optical sensor 213 includes at least one device selected from the group of an LED and photodiode pair, a fiber optic coupler, and an optical detecting head. Other optical devices can be utilized as well. Alternatively, the means for monitoring of the cells includes at least one electrical sensor 213 and at least one lead 276 in electrical communication with a corresponding electrical sensor 213. Such monitoring means can also be utilized to monitor other dynamic activities in the channel, for example, activities and responses of cells when a bolus 208 of selected chemicals moves along the channel 202, which is adapted for allowing such movement of material along the channel 202.

The bioreactors of this invention can find many applications. In addition to applications set forth elsewhere and among other things, they can be utilized for culturing, studying and observing a plurality of biofilms simultaneously, where each biofilm may contain a predetermined type of cells that are same or different from other biofilms. Each array can receive one or more collection of cells in one or more chambers to grow. A bolus of selected chemicals or other substances, same or different for different arrays, can be introduced to move along a corresponding channel for each array of chambers. And a spectrum of dynamic properties due to the interfacing between the cells and the bolus of selected chemicals or other substances can be observed, detected, collected, analyzed and utilized.

Capillary Bioreactor

Referring now to FIGS. 11(A-D), the present invention can be practiced in association with an inventive bioreactor 1100 and its variants as shown in FIGS. 11(A-D). In one embodiment, referring first to FIGS. 11A, 11A2 and 11A3, the bioreactor 1100 includes a first substrate 1124 having a first surface 1124a, an opposite second surface 1124b and edges. The bioreactor 1100 further includes a second substrate 1121 having a first surface 1121a and an opposite second surface 1121b, defining a cavity 1121c with a bottom surface 1121d, where the bottom surface 1121d is located therebetween the first surface 1121a and the second surface 1121b. The first surface 1124a of the first substrate 1124 is received by the second surface 1121b of the second substrate 1121 to cover the cavity 1121c so as to form a channel 1101 for receiving cells and a liquid medium. The second substrate 1121 can be fabricated from glass, Mylar, PDMS, silicon, a polymer, a semiconductor, or any combination of them. The first substrate 1124 is at least partially optically transparent such that the dynamic activities of cells in the channel 1101 are detectable through optical detecting means.

A recess 1105c is formed in the second substrate 1121 with a bottom surface 1105d and in fluid communication with the channel 1101. Additionally, a barrier 1106 is positioned for covering the recess 1105c so as to form an outer chamber 1105. The barrier 1006 has a porosity to allow the channel 1101 and the outer chamber 1105 to be in fluid communication and control the move of at least one predetermined type of cells between the channel 1101 and the outer chamber 1105. In one embodiment as best shown in FIG. 11A1, the barrier 1106 includes a plurality of posts spaced with a gap from each other. These posts may be coated in certain locations with substances to prevent entry of cells, particularly the endothelial cells. Gaps between the posts in certain locations allow for delivery of particular cell types to the outer chamber 1105 The second substrate 1121 further defines a first opening 1101a and an opposite, second opening 1101b adapted for allowing a flow of liquid to be introduced into the channel 1101 through the first opening 1101a and away from the channel 1101 through the second opening 1101b substantially along a first direction 1101c.

The bioreactor 1100 further includes a biocompatible coating layer 1102 applied to the interior surfaces of the second substrate 1121 around the channel 1101. The biocompatible coating layer 1102 includes a material that may inhibit cell adhesion to the biocompatible coating layer, enhance cell adhesion to the biocompatible coating layer, promote organization and growth of cells, or function as a fluorescent marker or indicator of the state of cells.

In forming the bioreactor 1100, the channel 1101 is sized to allow the growth of a layer of cells 1103 on the biocompatible coating layer 1102 and the flow of liquid in the channel 1101. The flow of liquid is controlled so as to provide a known shear force to the layer of cells 1103. The flow of liquid can be further controlled so as to provide an environment that simulates a vascular space in the channel 1101. For examples, the channel 1101 can be used for introduction of endothelial cells, and for their subsequent perfusion.

The cells can be any type of living cells, including, but not limited to, bacteria, protozoa, or both, normal cells, endothelial cells, tumor cells, or any combination of them. Cells can be introduced into the channel 1101 individually, in a collection of cells, or in the form of biofilm. In one embodiment, the layer of cells 1103 substantially forms an endothelial cells lined capillary in the channel 1101. The channel 1101 is sized such that when at least one cell 1104 that is not one of the endothelial cells, such as a tumor cell, is introduced into the channel 1101, it can undergo intravasation in the endothelial cells lined capillary.

Figure 11B:
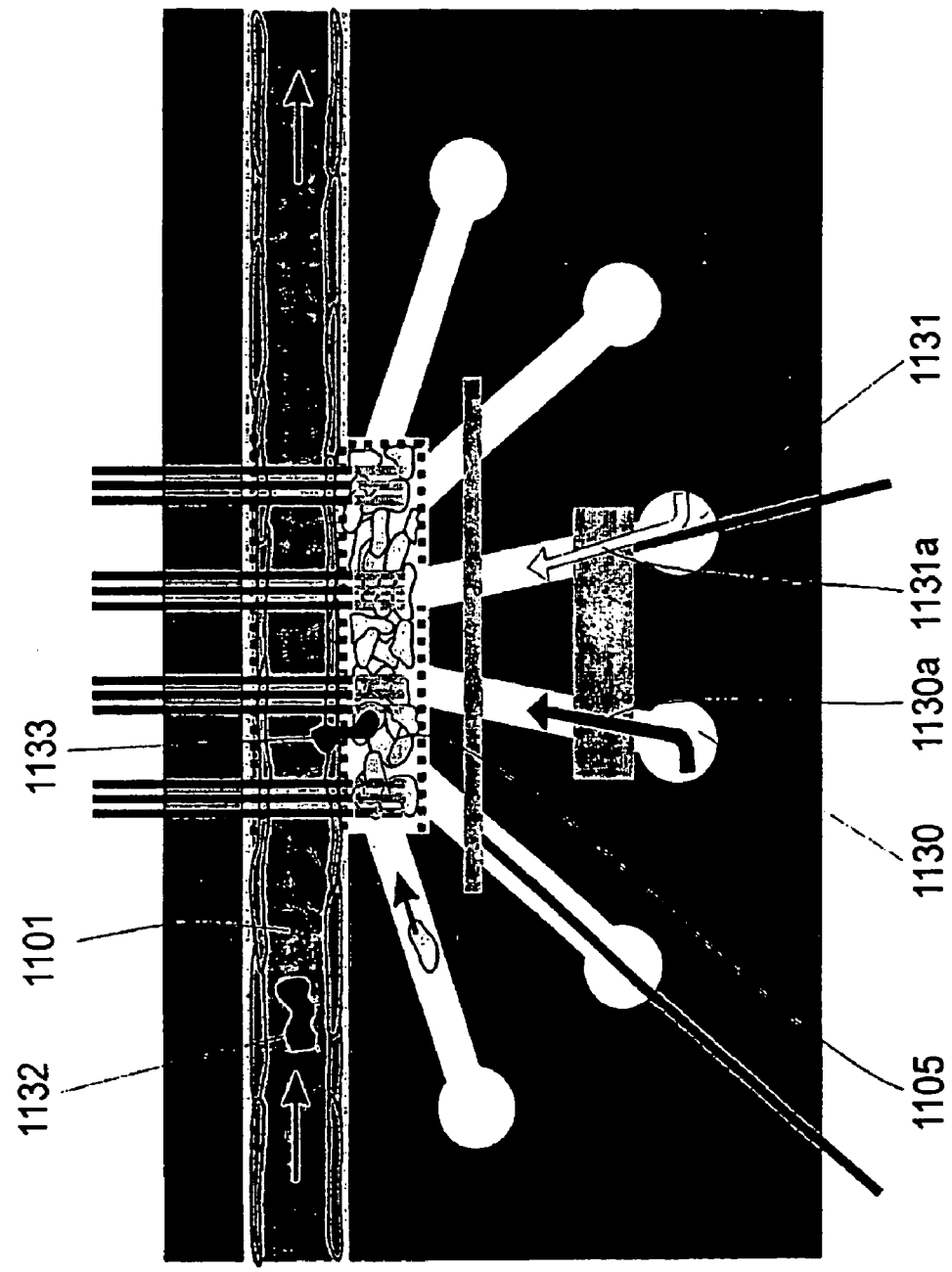
FIG. 11B schematically shows a top cross-sectional view of a bioreactor according to another embodiment of the present invention.
Figure 11C:
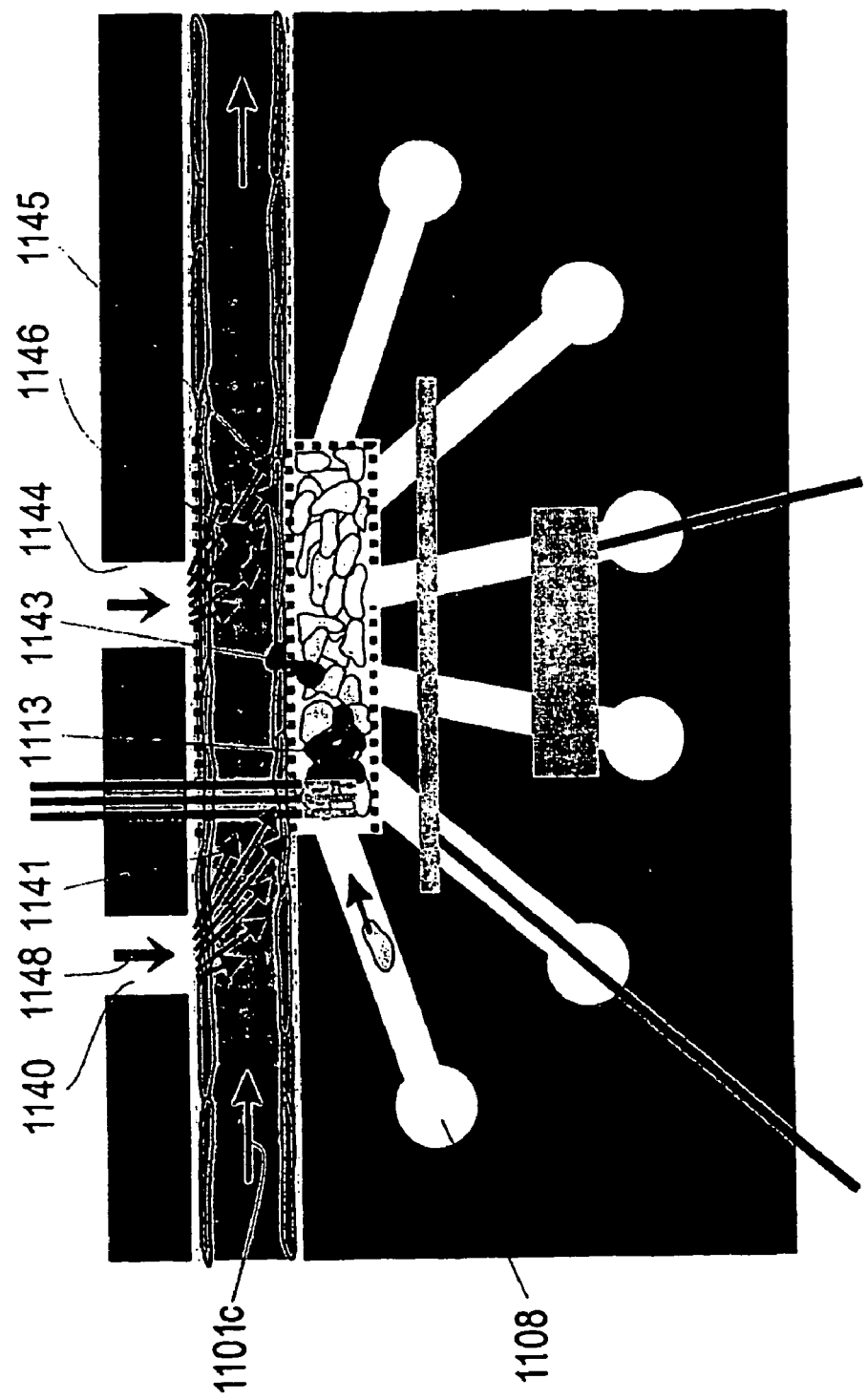
FIG. 11C schematically shows a top cross-sectional view of a bioreactor according to yet another embodiment of the present invention.

In an alternative embodiment as shown in FIG. 11C, the second substrate 1121 further defines one or more injection ports 1140, 1141 in fluid communication with the channel 1101 to allow a stream of substance to be introduced into the channel 1101 through the injection port 1140, 1141 substantially along a second direction 1148, respectively. As shown in FIG. 11C, the second direction 1148 is substantially perpendicular to the first direction 1101c. The stream of substance is controlled so as to provide a gradient to the channel 1101. The stream of substance includes a substance affecting the growth of cells such as chemokine.

Referring now to FIGS. 11A1, 11A2 and 11A3, the outer chamber 1105 is sized to allow the growth of a host of cells. The host of cells includes at least a first type of cells 1107 and a second type of cells 1113 that is different from the first type of cells 1107. In other words, the outer chamber 1105 is sized to allow the growth of two types of cells. In one embodiment, the first type of cells 1107 includes normal cells, and the second type of cells 1113 includes tumor cells. These host cells can either be grown in the outer chamber 1105, or so as to avoid undesired growth of endothelial cells into the host cell population, they may be grown on a suitable substrate outside of the bioreactor 1100 and then be introduced as a complete unit or smaller units into the outer chamber 1105 either through one of the microfluid ports or by temporary removal of the first substrate 1124 such as a glass lid of the outer chamber 1105. As best shown in FIG. 11A2, a port 1122 and a connection channel 1123 are formed in the second substrate 1121 such that the connection channel 1123 is in fluid communication with the outer chamber 1105 and the port 1122. The bioreactor 1100 further includes a plurality of electrodes 1114, 1115, 1116 adapted for electrochemical measurements of the host of cells. Moreover, the bioreactor 1100 further includes a plurality of controlling ports 1108, 1109, 1110 and a plurality of connection channels 1108a, 1109a, 1110a, wherein each of the connection channels 1108a, 1109a, 1110a is in fluid communication with a corresponding one of controlling ports 1108, 1109, 1110 and the outer chamber 1105, respectively.

Bioreactor 1100 and its variants as given above can find many applications. Such a readily fabricated device is suitable for events that are high-probability and in relatively short lengths of capillary, such as neutrophil binding to a tube of activated endothelial cells. Multiple channels/ports allow delivery of different cells, and establishment of chemokine, nutrient, and pH gradients. Electrodes measure metabolism. Hence it may best suited for experiments or applications involving activated or inflamed endothelial cells.

For example, as shown in FIG. 11B, bioreactor 1100 is used as a capillary perfused migration bioreactor for the study of cancer cell or neutrophil extravasation in the presence of two competing chemokine gradients. In particular, a first stream 1130a of chemokine is injected through a port 1130 and hence creates a first gradient of that chemokine both in the outer chamber 1105 and the channel 1101. Additionally, a second stream 1131a of chemokine is injected through a port 1131 and hence creates a second gradient of that chemokine both in the outer chamber 1105 and the channel 1101. A spectrum of dynamics of the cells may happen. For instances, a cancer cell or a neutrophil 1132 moves along the channel 1101 in response to either perfusion flow or the presence of the first and second chemokine gradients, and a cancer cell or neutrophil 1133 undergoes extravasation from the channel 1101 into the outer chamber 1105.

Figure 11D:
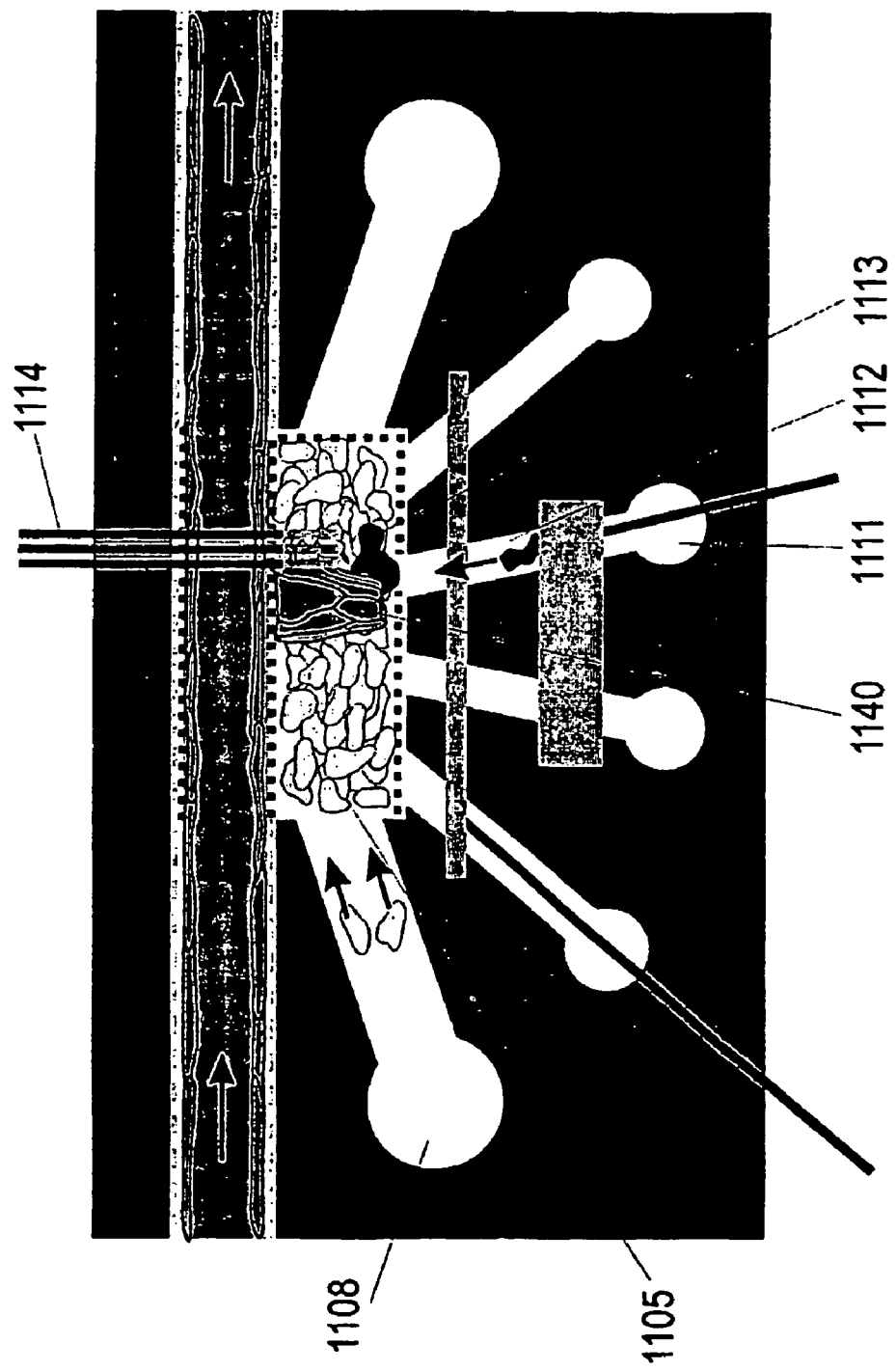
FIG. 11D schematically shows a top cross-sectional view of a bioreactor according to a further embodiment of the present invention.

FIG. 11D illustrates another application. Here bioreactor 1100 is used as a capillary perfused migration bioreactor for the study endothelial tube formation triggered by chemokine excreted by tumor cells, where the outer chamber 1105 of sufficient size contain a sufficiently larger volume of host cells 1108 that is required to ensure endothelial tube formation. An endothelial tube 1140 is formed in response to either chemokine being released by the tumor cells 1113, or by microfluidic delivery of vascular endothelial growth factor (VEGF) or other substances through the microfluidic port 1111. Note that another tumor cell 1112 is on the move. The electrodes 1114 may be able to detect changes in the extracellular environment associated with tube formation and the associated proteolysis.

Bioreactor with Multiple Traps

Referring now to FIGS. 10(A-I), the present invention can also be practiced in association with an inventive bioreactor 1000 and its variants as shown in FIGS. 10(A-I). In one embodiment, referring first to FIGS. 10A, 10B, 10G, 10H and 10I, the bioreactor 1000 includes a first substrate 1001 having a first surface 1001a and an opposite second surface 1011b, defining a chamber 1006 therebetween for receiving cells 1008 and a liquid medium. The first substrate 1001 can be fabricated from glass, Mylar, PDMS, silicon, a polymer, a semiconductor, or any combination of them.

An inlet port 1021 and a first connection channel 1021a are formed in the first substrate 1001, where the first connection channel 1021a is in fluid communication with the inlet port 1021 and the chamber 1006 for allowing a stream of substance to be delivered to the chamber 1006. Additionally, an outlet port 1005 and a second connection channel 1005a are formed in the first substrate 1001, where the second connection channel 1005a is in fluid communication with the outlet port 1005 and the chamber 1006 for allowing a stream of substance to be removed from the chamber 1006.

Moreover, as best shown in the insert of FIG. 10A, the bioreactor 1000 has confining means 1003 positioned in a region in the chamber 1006 proximate to the first connection channel 1021a to confine the cells 1008. In one embodiment, the confining means 1003 includes a plurality of traps 1007, where each of the plurality of traps 1007 is capable of receiving at least one cell or a collection of cells 1008. Each of the plurality of traps 1007 includes a structure defining a recess 1007a so as to receive and confine one or more cells 1008 therein. The structure may be partially formed with a filter 1007b to allow the recess 1007a to be in fluid communication with the chamber 1006. The filter 1007b can be formed with a plurality posts spacing from each other with a gap g. Traps can take various shapes and have different physics properties. For examples, in the embodiment as shown in FIG. 10G, a trap 1090 has distinct posts and sides. In the embodiment as shown in FIG. 10H, a trap 1092 has posts and sides that are extending to the posts. And in the embodiment as shown in FIG. 10I, a trap 1093 is formed with a single post and sides. The plurality of traps 1007 can be arranged to form an array.

Additionally, the first substrate 1001 defines a first alternate port 1022 and a third connection channel 1022a in fluid communication with the first alternate port 1022 and the first connection channel 1021a for allowing additional substance to be introduced into the chamber 1006. Moreover, the first substrate 1001 further defines a second alternate port 1011, a third connection channel 1011a, and a second chamber 1009, wherein the third connection channel 1011a is in fluid communication with second alternate port 1011 and the second chamber 1009, and the second chamber 1009 is in fluid communication with the first connection channel 1021a. Furthermore, the second chamber 1009 is formed with an oxygen permeable structure to provide oxygen to the cells.

Figure 10B:
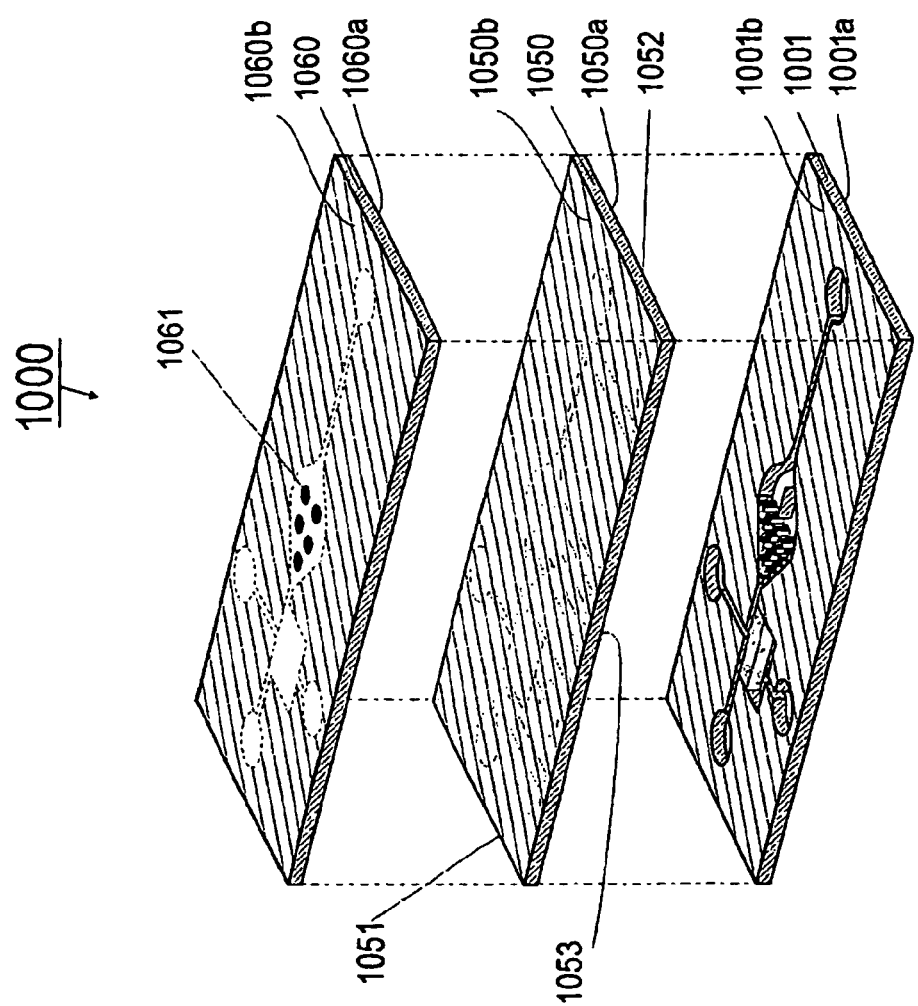
FIG. 10B schematically shows a perspective view of a bioreactor with multiple traps according to another embodiment of the present invention.
Figure 10C:
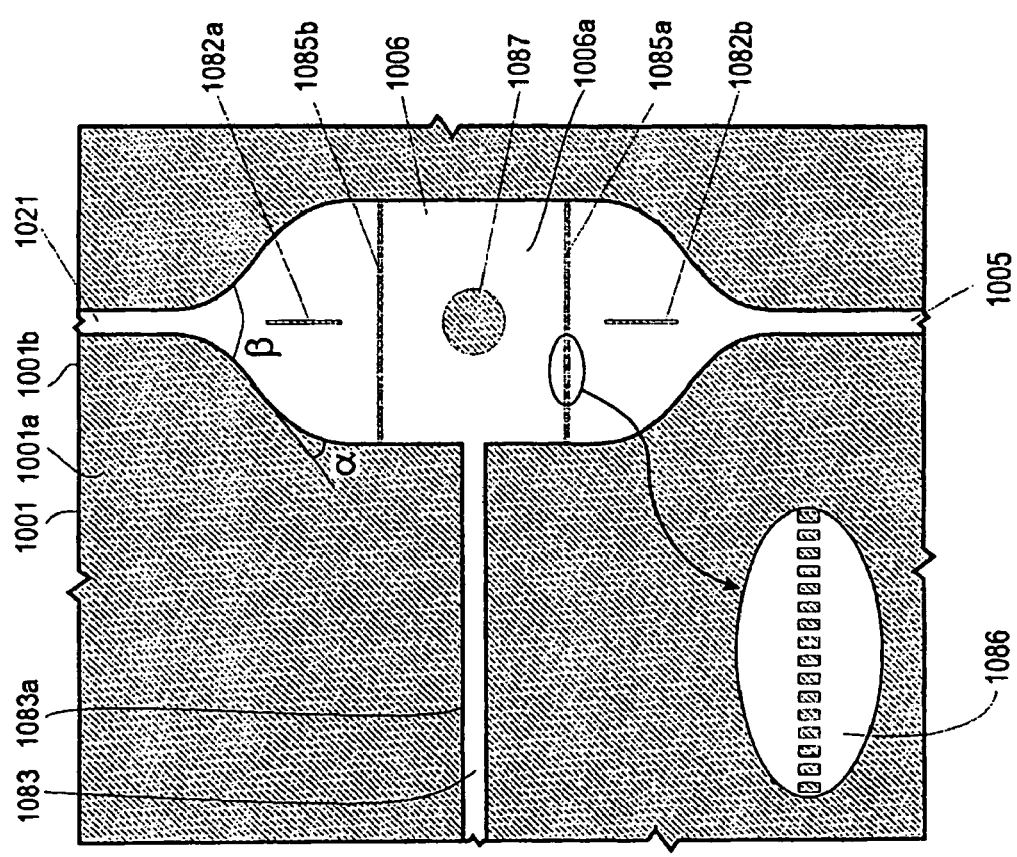
FIG. 10C schematically shows a top cross-sectional view of a bioreactor with a confined region according to one embodiment of the present invention.
Figure 10D:
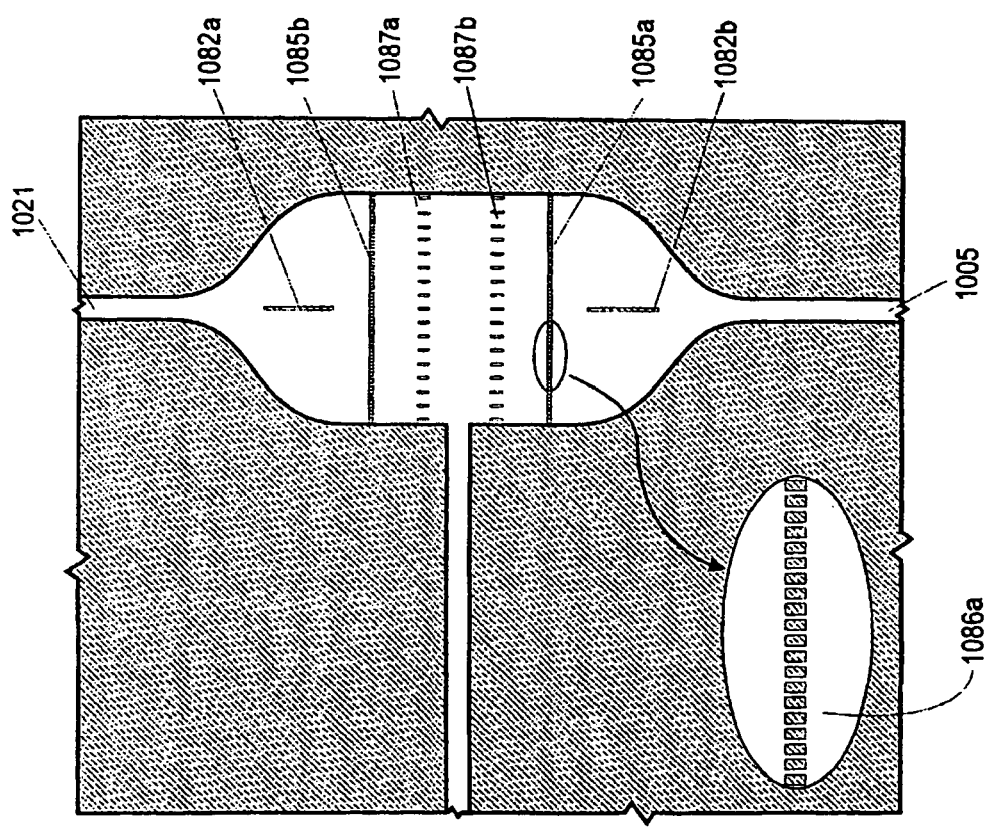
FIG. 10D schematically shows a top cross-sectional view of a bioreactor with a confined region according to another embodiment of the present invention.
Figure 10E:
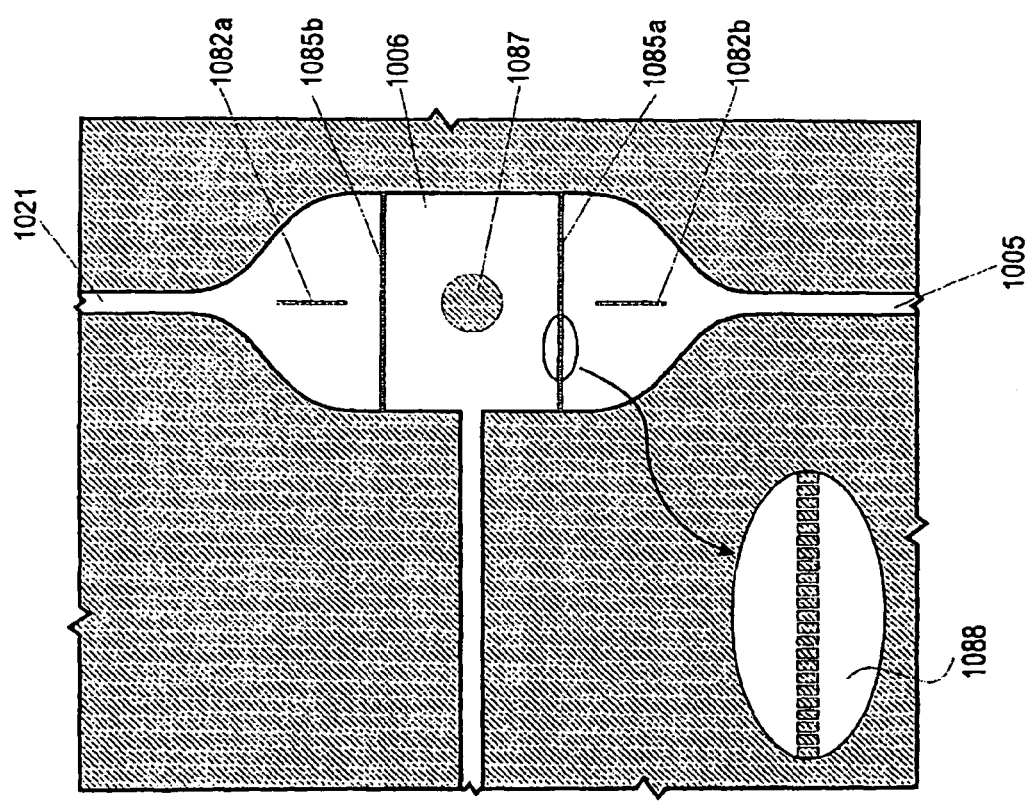
FIG. 10E schematically shows a top cross-sectional view of a bioreactor with a confined region according to yet another embodiment of the present invention.
Figure 10F:
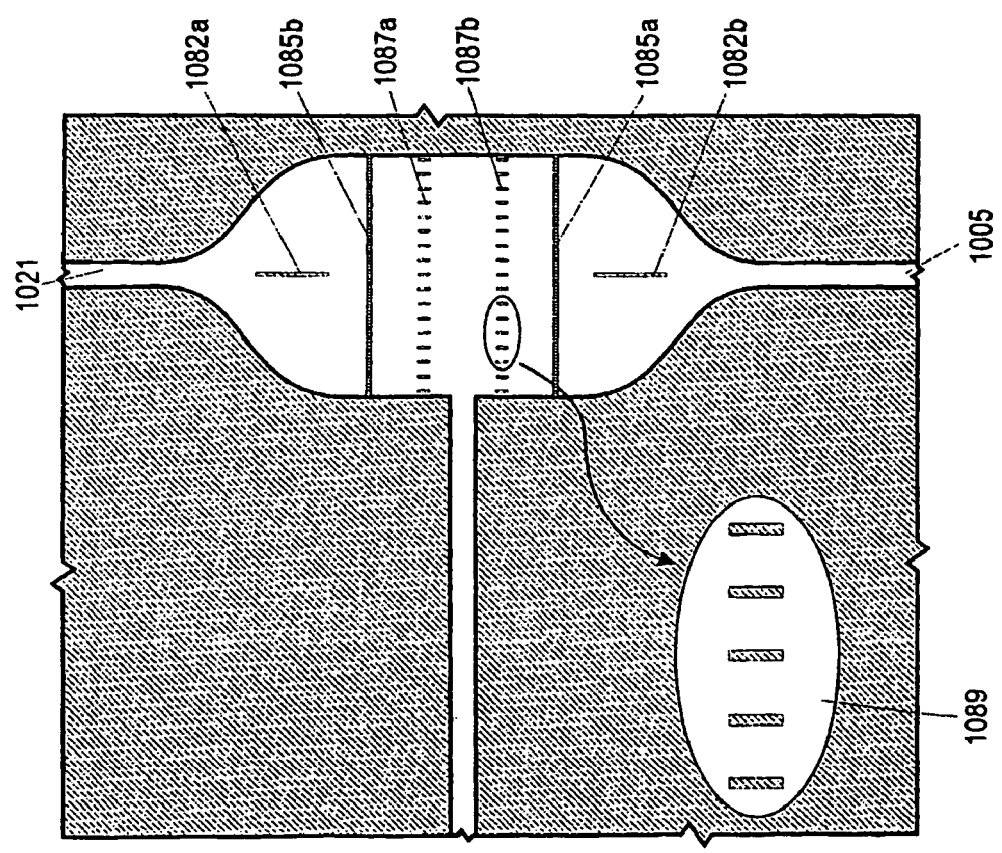
FIG. 10F schematically shows a top cross-sectional view of a bioreactor with a confined region according to a further embodiment of the present invention.
Figure 10G:
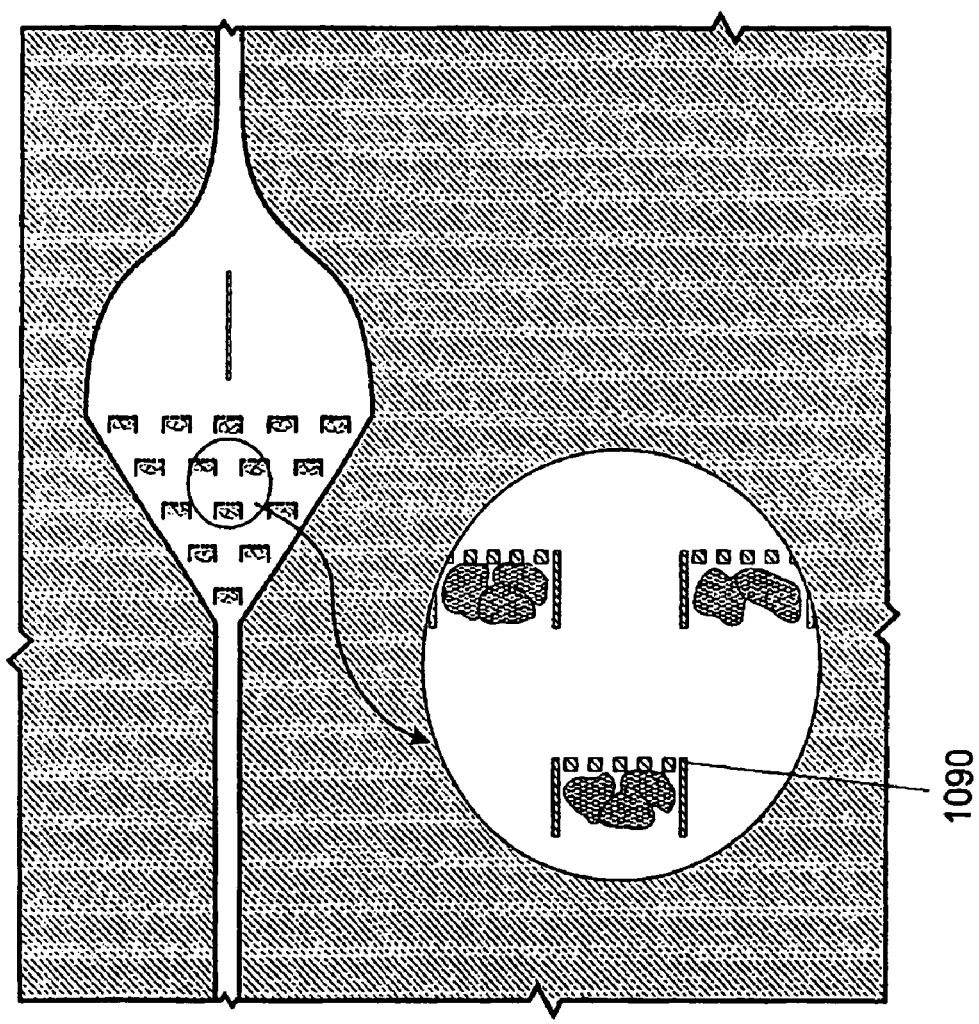
FIG. 10G schematically shows a top cross-sectional view of a bioreactor with multiple traps according to one embodiment of the present invention.
Figure 10H:
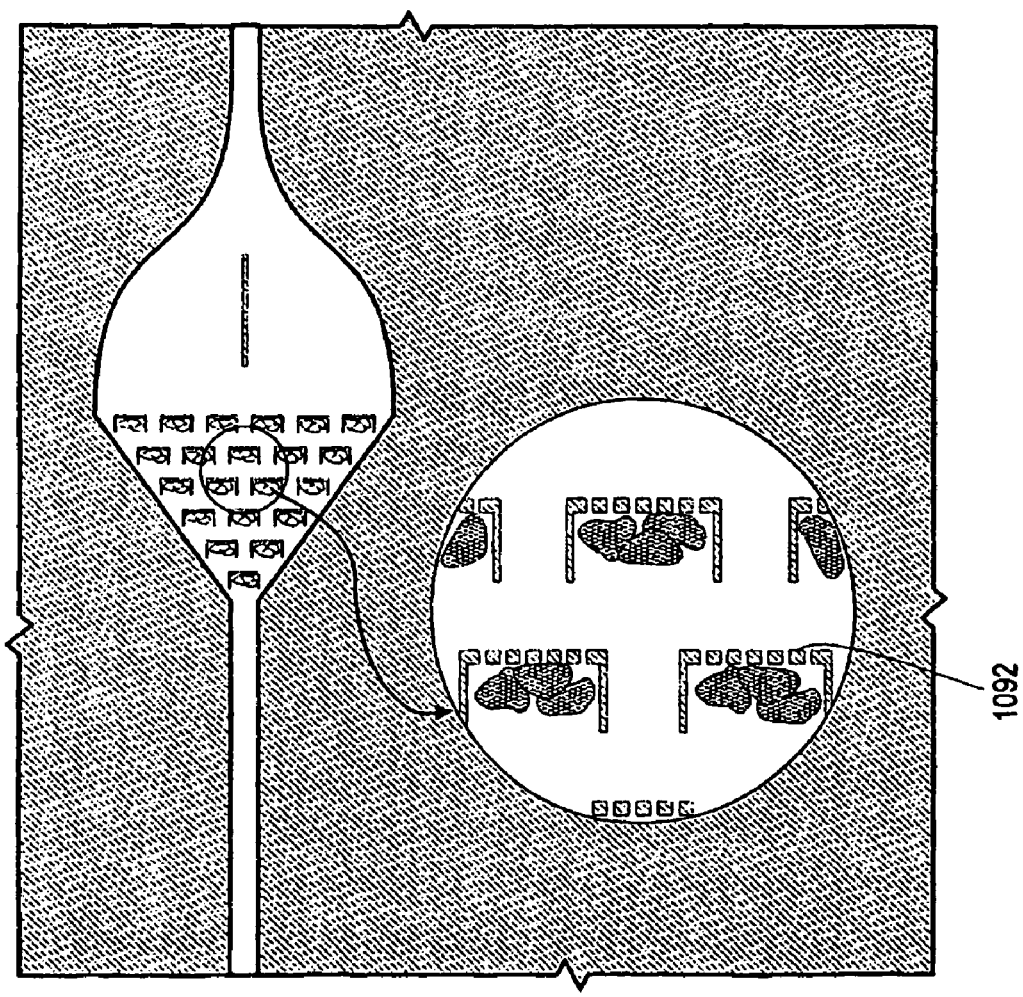
FIG. 10H schematically shows a top cross-sectional view of a bioreactor with multiple traps according to another embodiment of the present invention FIG. 10I schematically shows a top cross-sectional view of a bioreactor with multiple traps according to yet another embodiment of the present invention.
Figure 10I:
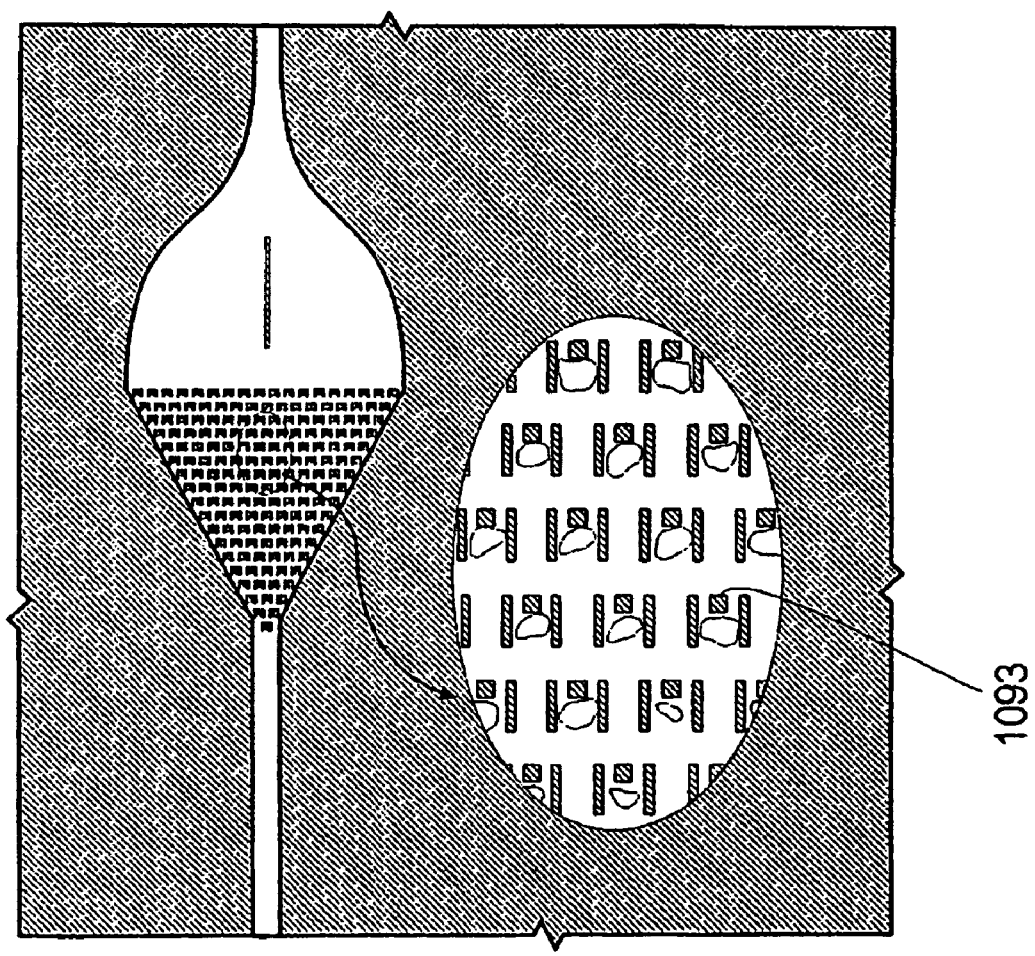

Referring now to FIG. 10B, the bioreactor 1100 further includes a second substrate 1050 having a first surface 1050a and an opposite, second surface 1050b, and means adapted for electrochemical measurements of the cells in the chamber 1006. The means for electrochemical measurements is positioned with the second substrate 1050 such that when the first surface 1050a of the second substrate 1050 is received by the second surface 1001b of the first substrate 1001, the means for electrochemical measurements is at a corresponding measurement position. The means for electrochemical measurements includes at least one electrode 1051 monitoring entry of the cells into the chamber 1006, at least one electrode 1052 monitoring leaving of the cells from the chamber 1006, and a plurality of electrodes 1053 detecting chemical species in the chamber 1006.

The bioreactor 1000 further includes a third substrate 1060 having a first surface 1060a and an opposite, second surface 1060b, and means adapted for optical measurements. The means for optical measurements is positioned with the third substrate 1060 such that when the first surface 1060a of the third substrate 1060 is received by the second surface 1001b of the first substrate 1001, the means for optical measurements is at a corresponding measurement position. The means for optical measurements includes a plurality of optical sensors 1061 strategically positioned for detecting chemical and biological species within the chamber 1006 and the physiological state of the cells within the chamber 1006. The third substrate 1060 is at least partially transparent.

Bioreactor with Confined Region

Referring now to FIGS. 10(C-F), the present invention can also be practiced in association with an inventive bioreactor 1000 and its variants as shown in FIGS. 10(C-F). In one embodiment, referring first to FIGS. 10C, 10D, 10E and 10F, the bioreactor 1000 includes a first substrate 1001 having a first surface 1001a and an opposite second surface 1001b, defining a chamber 1006 therebetween for receiving cells 1008 and a liquid medium. The first substrate 1001 can be fabricated from glass, Mylar, PDMS, silicon, a polymer, a semiconductor, or any combination of them. The bioreactor 1000 further includes a second substrate (not shown) sized such that when the second substrate 1050 received by the first substrate 1001, the chamber 1006 is covered.

An inlet port (not shown) and a first connection channel 1021 are formed in the first substrate 1001, where the first connection channel 1021 is in fluid communication with the inlet port (not shown) and the chamber 1006 for allowing a stream of substance to be delivered to the chamber 1006.

Additionally, an outlet port (not shown) and a second connection channel 1005 are formed in the first substrate 1001, where the second connection channel 1005 is in fluid communication with the outlet port (not shown) and the chamber 1006 for allowing a stream of substance to be removed from the chamber 1006.

The bioreactor 1000 further has confining means positioned in the chamber 1006 to form a confinement region 1006a to confine the cells 1008 therein. In one embodiment, the confining means includes a first filter 1085a and a second filter 1085b, where the first filter 1085a is positioned proximate to the first connection channel 1021 and the second filter 1085b is positioned proximate to the second connection channel 1005, and the first filter 1085a and the second filter 1085b are substantially parallel to each other. Each of the first filter 1085a and the second filter 1085b includes a plurality of posts 1086 spaced apart from each other not to allow cells to pass through it. The distances between two neighboring posts can vary. For examples, posts 1086, 1086a, 1088 and 1089, as shown in FIGS. 10C, 10D, 10E and 10F, show posts with different gaps, respectively.

The first substrate 1001, referring now to FIG. 1C, further defines a first alternate port 1083 and a third connection channel 1083a that is in fluid communication with the first alternate port 1083 and the confined region 1006a of the chamber 1006 for allowing seed cells to perfuse only outside the confined region 1006a in the chamber 1006.

The bioreactor 1100 further includes one or more supporting members 1082a, 1082b positioned outside the confined region 1006a of the chamber 1006 for supporting the second substrate 1050. Additionally, the bioreactor 1100 further includes at least one supporting member 1087 positioned inside the confined region 1006a of the chamber 1006 for supporting the second substrate 1050. Note that the chamber 1006 is formed with sidewalls of the chamber 1006 are tapered at the intersections of the connection channels with the chamber 1006 to form an angle of inclination α, which is preferred in the range of about between 10-45° from vertical, and an enclosed angle β, which is preferred in the range of about between 30-80°, respectively, to avoid shear forces generated by sharp corners.

Bioreactor with Multiple Chambers

Referring now to FIGS. 8(A-D), the present invention can also be practiced in association with an inventive bioreactor 800 and its variants as shown in FIGS. 8(A-D). In one embodiment, referring first to FIG. 8A, the bioreactor 800 includes a first substrate 801 having a first surface and an opposite second surface, defining a first chamber 812 therebetween for receiving a first type of cells and a liquid medium. One or more second chambers 811a, 811b, 811c, 811d are formed in the first substrate 801 for receiving a second type of cells and a liquid medium. Moreover, one or more connection channels 813a, 813b, 813c, 813d are formed in the first substrate 801, wherein each of connection channels 813a, 813b, 813c, 813d is in fluid communication with a corresponding second chamber 811a, 811b, 811c, 811d and the first chamber 812 for allowing the first type of cells and the second type of the cells to interact with each other. For example, connection channel 813a is in fluid communication with a corresponding second chamber 811a and the first chamber 812. The first type of cells includes protozoa, and the second type of cells includes bacteria.

The connection channels 813a, 813b, 813c, 813d are formed to allow protozoa to travel therein. However, a variety of structures can be utilized to limit the mobility of protozoa for different applications. For examples, in an embodiment 804 as shown in FIG. 8B, a sizing limiting or exclusion post 805 is utilized to limit the mobility of protozoa, which can be used to evaluate the mobility of protozoa. Alternatively, in an embodiment 807 as shown in FIG. 8C, one of the connection channels 813a, 813b, 813c, 813d is formed with a cross-sectional dimension 808 variable along the length of the connection channel is utilized to limit the mobility of protozoa, which can also be used to evaluate the mobility of protozoa. Moreover, in an embodiment 809 as shown in FIG. 8D, a barrier 810 positioned in a connection channel is utilized for separation of bacteria and protozoa, which can be used to evaluate protozoa chemotaxis.

Bioreactors with Single Chamber and Substance Injection Capacity

Referring now to FIGS. 12(A-D), the present invention can be practiced in association with an inventive bioreactor 1200 and its variants as shown in FIGS. 12(A-D). In one embodiment, referring first to FIGS. 12A1, 12A2 and 12A3, the bioreactor 1200 includes a first substrate 1202 having a first surface 1202a, an opposite second surface 1202b and edges. The bioreactor 1200 further includes a second substrate 1201 having a first surface 1201a and an opposite second surface 1201b, defining a cavity 1201c with a bottom surface 1201d, where the bottom surface 1201d is located therebetween the first surface 1201a and the second surface 1201b. The first surface 1202a of the first substrate 1202 is received by the second surface 1201b of the second substrate 1201 to cover the cavity 1201c so as to form a chamber 1203 for receiving cells and a liquid medium. The second substrate 1201 can be fabricated from glass, Mylar, PDMS, silicon, a polymer, a semiconductor, or any combination of them.

A port 1209 is formed in the second substrate 1201 between the bottom surface 1201d and the first surface 1201a of the second substrate 1201 with a first opening 1209a and an opposite, second opening 1209b. As formed, the port 1209 is in fluid communication with the chamber 1203 through the first opening 1209a to allow a stream of substance to be introduced into the chamber 1203 through the port 1209 substantially along a first direction 1210. The stream of substance is controlled so as to provide a gradient, or a concentration gradient of the substance, to the chamber 1203 at least around the first opening 1209a. Indeed, the design of this inventive bioreactor allows a concentration gradient of the substance to be provided to and substantially felt by the entire chamber 1203. The stream of substance includes a substance affecting the growth of cells such as chemokine.

The second substrate 1201 further defines a third opening 1209c and an opposite fourth opening 1209d adapted for allowing a flow of liquid to be introduced into the chamber 1203 through the third opening 1209c and away from the chamber 1203 through the fourth opening 1209d substantially along a second direction 1208. As shown in FIGS. 12A1, 12A2 and 12A3, the second direction 1208 is substantially perpendicular to the first direction 1210.

The bioreactor 1200 further includes a biocompatible coating layer 1205a applied to the bottom surface 1201d of the second substrate 1201. The biocompatible coating layer 1205a includes a material that may inhibit cell adhesion to the biocompatible coating layer, enhance cell adhesion to the biocompatible coating layer, or function as a fluorescent marker or indicator of the state of cells.

In forming the bioreactor 1200, the first surface 1202a of the first substrate 1202 and the second surface 1201b of the second substrate 1201 is spaced such that when a layer of cells 1206 grows on the biocompatible coating layer 1205a, a flow of liquid can flow in the chamber 1203 between the first surface 1202a of the first substrate 1202 and the layer of cells 1206 along the second direction 1208. The flow of liquid is controlled so as to provide a known shear force to the layer of cells 1206. The flow of liquid may be further controlled so as to provide perfusion and maintenance to the layer of cells 1206. In other words, this flow can perfuse all cells in the chamber 1203, and can be intermittent only as allowed by cell maintenance. Note that in motion this flow crosses the concentration gradient of the substance in the region proximate to the first opening 1209a of the port 1209. The cells can be any type of living cells, including, but not limited to, bacteria, protozoa, or both, normal cells, tumor cells, or any combination of them. Cells can be introduced into a chamber individually, in a collection of cells, or in the form of biofilm. In one embodiment, a layer of endothelial cells grows on the chamber 1203.

Moreover, the first surface 1202a of the first substrate 1202 and the second surface 1201b of the second substrate 1201 are spaced to further allow at least one cell 1207 to migrate above the layer of cells 1206. The at least one cell to migrate can be a cell having a type same or different from the type of the layer of cells 1206.

Figure 12B:
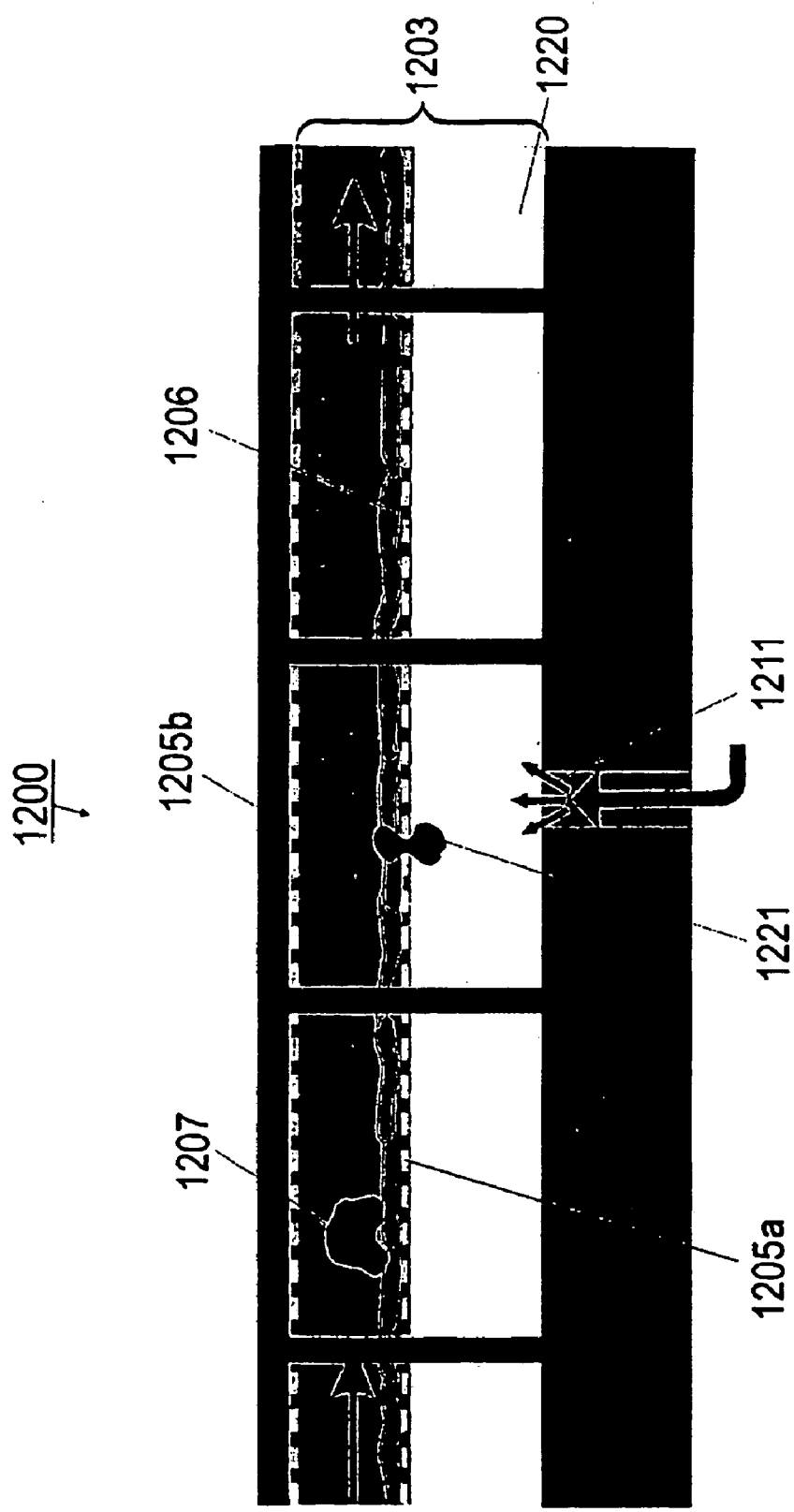
FIG. 12B shows a side cross-sectional view of a bioreactor with chemokine injection according to another embodiment of the present invention.

In an alternative embodiment of the present invention as shown in FIG. 12B, the bioreactor 1200 further includes a layer of porous material 1220 that is positioned on the bottom surface 1201d of the second substrate 1201. A biocompatible coating layer 1205a can be applied to the layer of porous material 1220 such that the layer of porous material 1220 is between the biocompatible coating layer 1205a and the bottom surface 1201d of the second substrate 1201. The biocompatible coating layer 1205a includes a material that may inhibit cell adhesion to the biocompatible coating layer, enhance cell adhesion to the biocompatible coating layer, or function as a fluorescent marker or indicator of the state of cells.

In this embodiment, as shown in FIG. 12B, the first surface 1202a of the first substrate 1202 and the second surface 1201b of the second substrate 1201 are spaced such that when a layer of cells 1206 grows on the biocompatible coating layer 1205a, a flow of liquid can flow in the chamber 1203 between the first surface 1202a of the first substrate 1202 and the layer of cells. The flow of liquid can also be controlled so as to provide a known shear force to the layer of cells. As such formed, the chamber 1203 is divided by the biocompatible coating layer 1205a into two regions: an upper region for flow, and a lower region for cell extravasation and/or other cell activities.

The layer of porous material 1220 can include collagen, an extracellular matrix, at least one cell culture scaffold supportive to the layer of cells 1206, or any combination of them. The layer of porous material 1220 may allow at least one cell 1221 to extravasate below the layer of cells 1206.

The first substrate 1202 is at least partially optically transparent. A biocompatible coating layer 1205b may be applied to the first surface 1202a of the first substrate 1202, where the biocompatible coating layer 1205b includes a material that may inhibit cell adhesion to the biocompatible coating layer, enhance cell adhesion to the biocompatible coating layer, or function as a fluorescent marker or indicator of the state of cells.

Referring now to FIGS. 12A1, 12A2, and 12A3, the first substrate 1202 and the second substrate 1201 are substantially parallel to each other and a plurality of posts 1204 are positioned between the first surface 1202a of the first substrate 1202 and the second surface 1201b of the second substrate 1201 to substantially maintain a predetermined separation between the first surface 1202a of the first substrate 1202 and the second surface 1201b of the second substrate 1201 to allow optical detecting of dynamic activities of cells in the chamber 1203. The dynamic activities of cells in the chamber 1203 are detectable through optical detecting means such as high-resolution optical microscope or a fluorescence-imaging device or both.

The predetermined separation between the first surface 1202a of the first substrate 1202 and the second surface 1201b of the second substrate 1201 should be maintained with sufficient accuracy for accurate optical measurements. To this end, the plurality of posts are positioned in at least two rows, and wherein each row of posts has at least two posts spaced from each other to form a stable support structure.

Figure 12C:
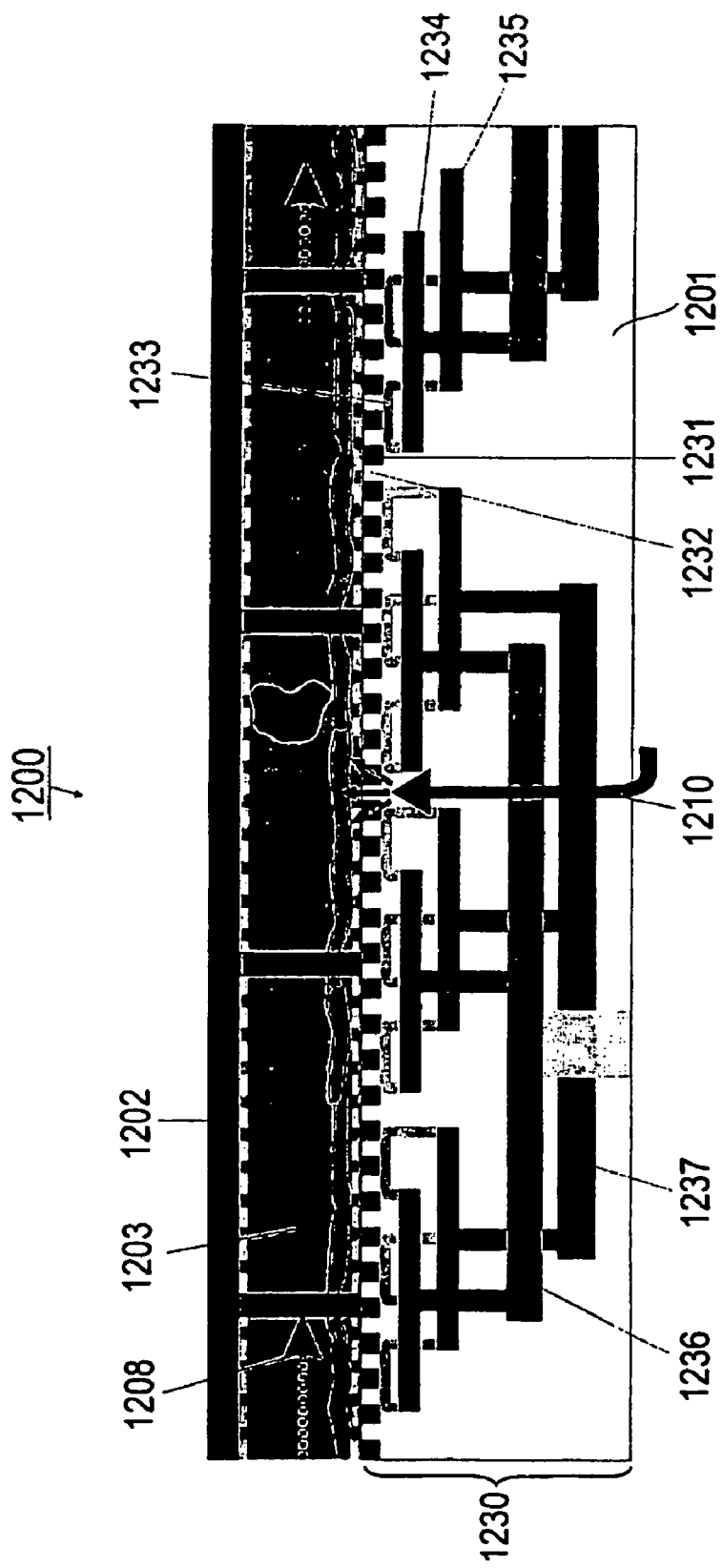
FIG. 12C shows a side cross-sectional view of a bioreactor with chemokine injection according to yet another embodiment of the present invention.
Figure 12D:
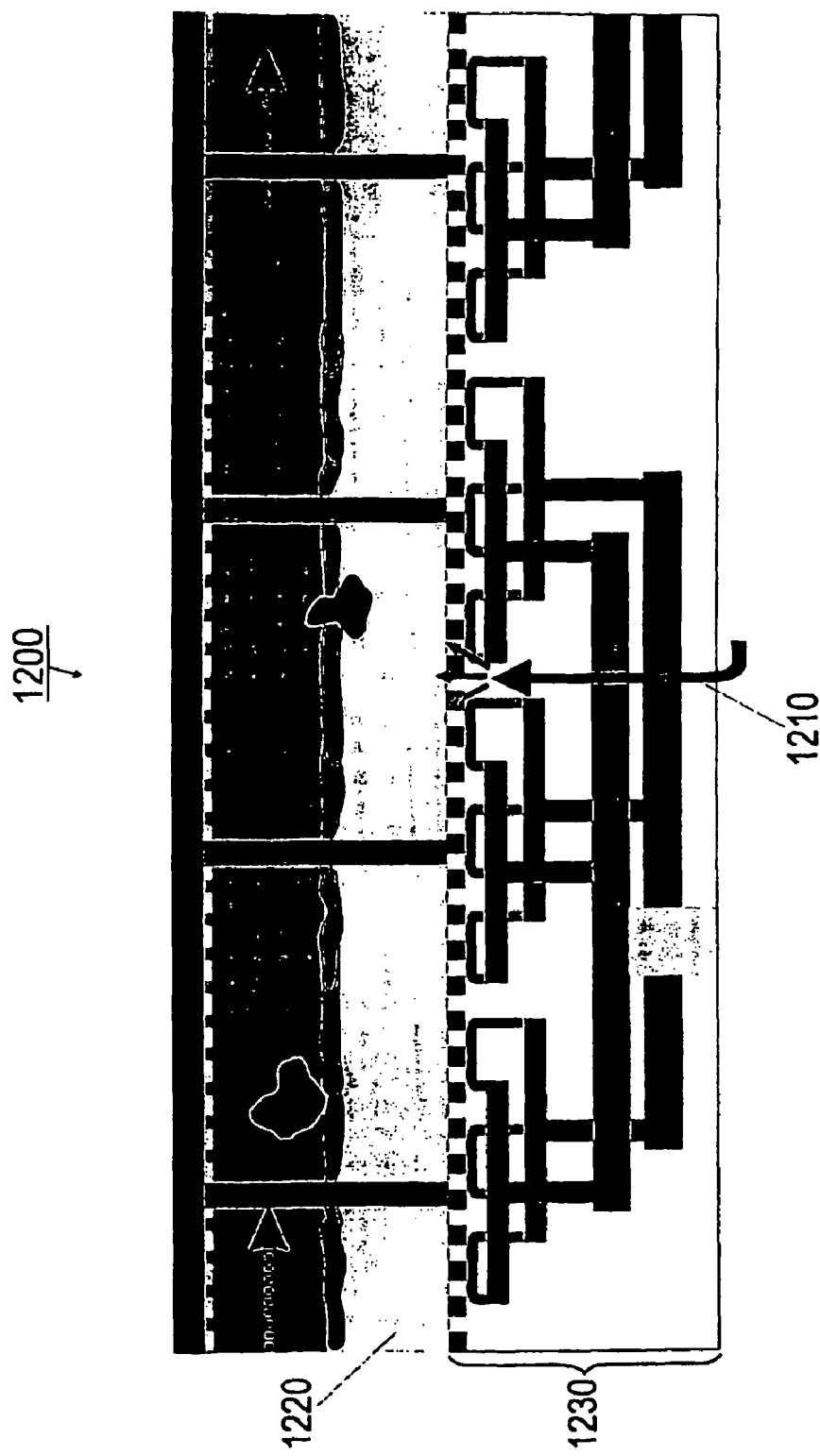
FIG. 12D shows a side cross-sectional view of a bioreactor with chemokine injection according to a further embodiment of the present invention.

In alternative embodiments as shown in FIG. 12C, in addition to the designs and structures set forth above related to FIGS. 12A1, 12A2, 12A3 and 12B, respectively, a bioreactor 1200 further includes perfusion means 1230 in fluid communication with the chamber 1203 to allow diffusional exchange of nutrients and metabolic byproducts with the chamber 1203.

The perfusion means 1230 includes a nanofilter 1231 with a plurality of pores 1232 in fluid communication with the chamber 1203, wherein the pores 1232 are sized to allow diffusional exchange of nutrients and metabolic byproducts with the chamber 1203 and not to allow cells to migrate across the nanofilter 1231. The pores 1232 may be further sized to allow cells to perfuse through only by bi-directional diffusion through the nanofilter 1231 in a manner such that substantially no shear is generated by the perfusion of cells. In one embodiment, the pores 1232 of the nanofilter 1231 are sized to have a dimension smaller than 400 nanometers cross-sectionally.

The perfusion means 1230 further includes a perfusion supply network in fluid communication with the nanofilter 1231 through the pores 1232. In one embodiment, the perfusion supply network includes a plurality of perfusion channels 1233, each being in fluid communication with the nanofilter 1231 to allow bi-directional, diffusional exchange of nutrients and metabolic byproducts with the nanofilter 1231 and being dimensioned to minimize pressure drops along each perfusion channel 1233 and to allow passive diffusional exchange of nutrients and metabolic byproducts along each perfusion channel 1233.

The perfusion supply network further includes a plurality of intermediate supply channels 1234, each being in fluid communication with a plurality of corresponding perfusion channel 1233 so as to provide perfusate to the plurality of corresponding perfusion channel 1233. Moreover, the perfusion supply network has a plurality of intermediate return channels 1235, each being in fluid communication with a plurality of corresponding perfusion channel 1233 so as to collect perfusate from the plurality of corresponding perfusion channel 1233.

Additionally, the perfusion supply network further includes a plurality of main supply channels 1236, each being in fluid communication with a plurality of corresponding intermediate supply channel 1234 so as to provide perfusate to the plurality of corresponding intermediate supply channel 1234, and a plurality of main return channels 1237, each being in fluid communication with a plurality of corresponding intermediate return channel 1237 so as to collect perfusate from the plurality of corresponding intermediate return channel 1237.

Bioreactors with Multiple Chambers and Substance Injection Capacity

Referring now to FIGS. 13(A-F), the present invention can also be practiced in association with an inventive bioreactor 1300 and its variants as shown in FIGS. 13(A-F). In one embodiment, referring first to FIGS. 13A and 13B, the bioreactor 1300 includes a first substrate 1302 having a first surface 1302a, an opposite second surface 1302b and edges. The bioreactor 1300 further includes a second substrate 1301 having a first surface 1301a and an opposite second surface 1301b, defining a cavity 1301c with a bottom surface 1301d, where the bottom surface 1301d is located therebetween the first surface 1301a and the second surface 1301b. The first surface 1302a of the first substrate 1302 is received by the second surface 1301b of the second substrate 1301 to cover the cavity 1301c so as to form a chamber 1303 for receiving cells and a liquid medium. The second substrate 1301 can be fabricated from glass, Mylar, PDMS, silicon, a polymer, a semiconductor, or any combination of them.

The bioreactor 1300 further includes a filter 1351 dividing the chamber 1303 into a first subchamber 1353 and a second subchamber 1354, wherein the filter 1351 has a porosity to allow the first subchamber 1353 and the second subchamber 1354 in fluid communication. Additionally, a port 1309 is formed in the second substrate 1301 between the bottom surface 1301d and the first surface 1301a of the second substrate 1301 with a first opening 1309a and an opposite, second opening 1309b. As formed, the port 1309 is in fluid communication with the second subchamber 1354 through the first opening 1309a to allow a stream of substance to be introduced into the chamber 1303 through the port 1309 substantially along a first direction 1310. Similar to the embodiments shown in FIGS. 12(A-D) and set forth above, the stream of substance is controlled so as to provide a gradient, or a concentration gradient of the substance, to the chamber 1303 at least around the first opening 1309a. Again, the design of this inventive bioreactor allows a concentration gradient of the substance to be provided to and substantially felt by the entire chamber 1303. The stream of substance includes a substance affecting the growth of cells such as chemokine.

Figure 13A:
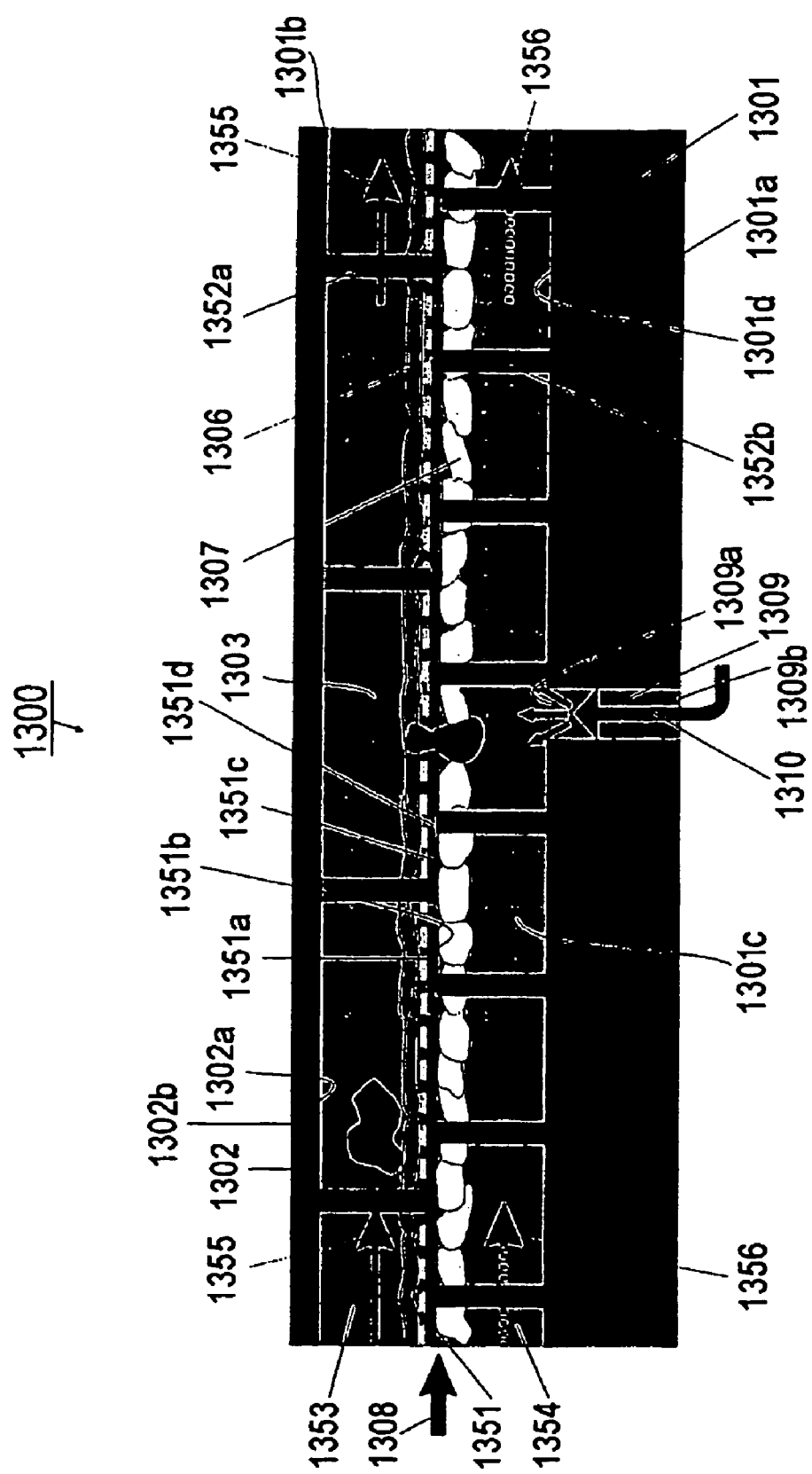
FIG. 13A shows a side cross-sectional view of a bioreactor with a two-chamber according to one embodiment of the present invention.

The second substrate 1301 further defines a third opening 1309c and an opposite fourth opening 1309d adapted for allowing a flow of liquid to be introduced into at least one of the first subchamber 1353 and the second subchamber 1354 through the third opening 1309c and away from at least one of the first subchamber 1353 and the second subchamber 1354 through the fourth opening 1309d substantially along a second direction 1308. As shown in FIG. 13A, the second direction 1308 is substantially perpendicular to the first direction 1310. As discussed in more detail below, same or different flows of liquid can be introduced to one or both of the first subchamber 1353 and the second subchamber 1354.

The filter 1351 has a first surface 1351a that partially defines the first subchamber 1353 with the first surface 1302a of the first substrate 1302, and an opposite second surface 1351b that partially defines the second subchamber 1354 with the second surface 1301b of the second substrate 1301. The filter 1351 includes a perfusion membrane 1351c with a plurality of pores 1351d to allow the filter 1351 to be in fluid communication with one or both of the first subchamber 1353 and the second subchamber 1354. The pores 1351d of the filter 1351 are sized to allow diffusional exchange of nutrients and metabolic byproducts with one or both of the first subchamber 1353 and the second subchamber 1354 but not to allow cells to migrate across the filter 1351. The pores 1351d are further sized to allow cells to perfuse through the filter 1351 only by bidirectional diffusion in a manner such that substantially no shear is generated by the perfusion of cells. In one embodiment, the pores 1351d of the filter 1351 are sized to have a dimension smaller than 400 nanometers cross-sectionally. In a more preferred embodiment, the pores 1351d of the filter 1351 are sized to have a dimension about 10 to 100 nanometers cross-sectionally.

The bioreactor 1300 further includes a plurality of posts 1352a that are strategically positioned between the first surface 1302a of the first substrate 1302 and the first surface 1351a of the filter 1351 to substantially maintain a predetermined separation between the first surface 1302a of the first substrate 1302 and the first surface 1351*a* of the filter 1351 to allow optical detecting of dynamic activities of cells in the first subchamber 1353. Additionally, the bioreactor 1300 includes a plurality of posts 1352*b* that are strategically positioned between the second surface 1301*b* of the second substrate 1301 and the second surface 1351*b* of the filter 1351 to substantially maintain a predetermined separation between the second surface 1301*b* of the second substrate 1301 and the second surface 1351*b* of the filter 1351 to allow optical detecting of dynamic activities of cells in the second subchamber 1354.

The predetermined separation between the first surface 1302*a* of the first substrate 1302 and the first surface 1351*a* of the filter 1351 and the predetermined separation between the second surface 1301*b* of the second substrate 1301 and the second surface 1351*b* of the filter 1351 should be maintained with sufficient accuracy for accurate optical measurements, respectively. To this end, the plurality of posts 1352*a* and 1352*b* are positioned in at least two rows, respectively, and where each row of posts has at least two posts spaced from each other to form a stable support structure. Posts 1352*a* and 1352*b*, as shown in FIG. 13A, may be positioned away from each other.

As such formed, the bioreactor 1300 allows activities such as cell seeding and flow in the first subchamber 1353 (or the upper chamber) and the second subchamber 1354 (or the lower chamber) to be controlled independently, thereby allowing coculture on opposite sides of the filter 1351 by inverting the device prior to adhesion of the cells in the lower chamber. Alternatively, the upper cell population can be grown on the filter 1351 simultaneously as the other cell population grows on the lower surface of the lower chamber. Thus, when a first flow of liquid 1355 is introduced into the first subchamber 1353, the first flow of liquid 1355 can be controlled so as to provide a known shear force to a first layer of cells 1306 growing in the first subchamber 1353 on the first surface 1351*a* side of the filter 1351 and an environment that simulates a vascular space in the first subchamber 1353. Jointly or independently, a second flow of liquid 1356 can also be introduced into the second subchamber 1354, and the second flow of liquid 1356 can be controlled so as to provide an environment that simulates a tissue space in the second subchamber 1354. The fact that first flow of liquid 1355 and the second flow of liquid 1356 can be controlled independently from each other means, among other things, they can have different contents, different flow velocities, and/or different timing of flow.

Moreover, as such formed, the bioreactor 1300 allows growing and culture of multiple layers (or populations) of cells therein. In addition to the first layer of cells 1306 growing in the first subchamber 1353, a second layer of cells 1307 is capable of growing in the second subchamber 1354 on the second surface 1351*b* side of the filter 1351. The first layer of cells 1306 growing in the first subchamber 1353 and the second layer of cells 1307 growing in the second subchamber 1354 can be same or different.

Figure 13B:
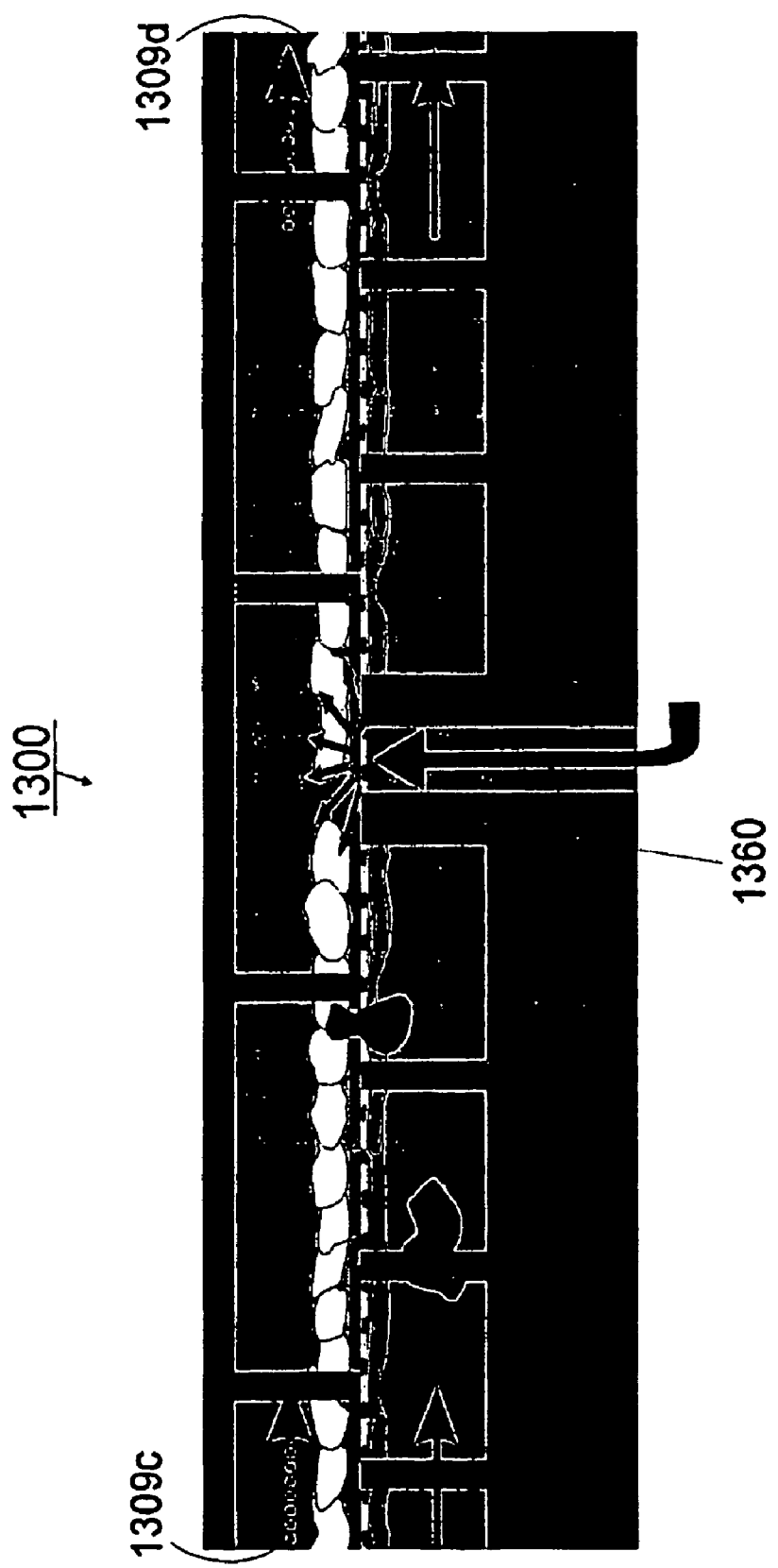
FIG. 13B shows a side cross-sectional view of the bioreactor as shown in FIG. 13A.

In an alternative embodiment as shown in FIG. 13B, an extension port member 1360 defining a channel therein is provided. As formed, the extension port member 1360 is positioned complimentarily to the port 1309 such that the channel of the extension port member 1360 is in fluid communication with the port 1309 and the first subchamber 1353 to allow the stream of substance to be directly introduced to the first subchamber 1353.

Figure 13C:
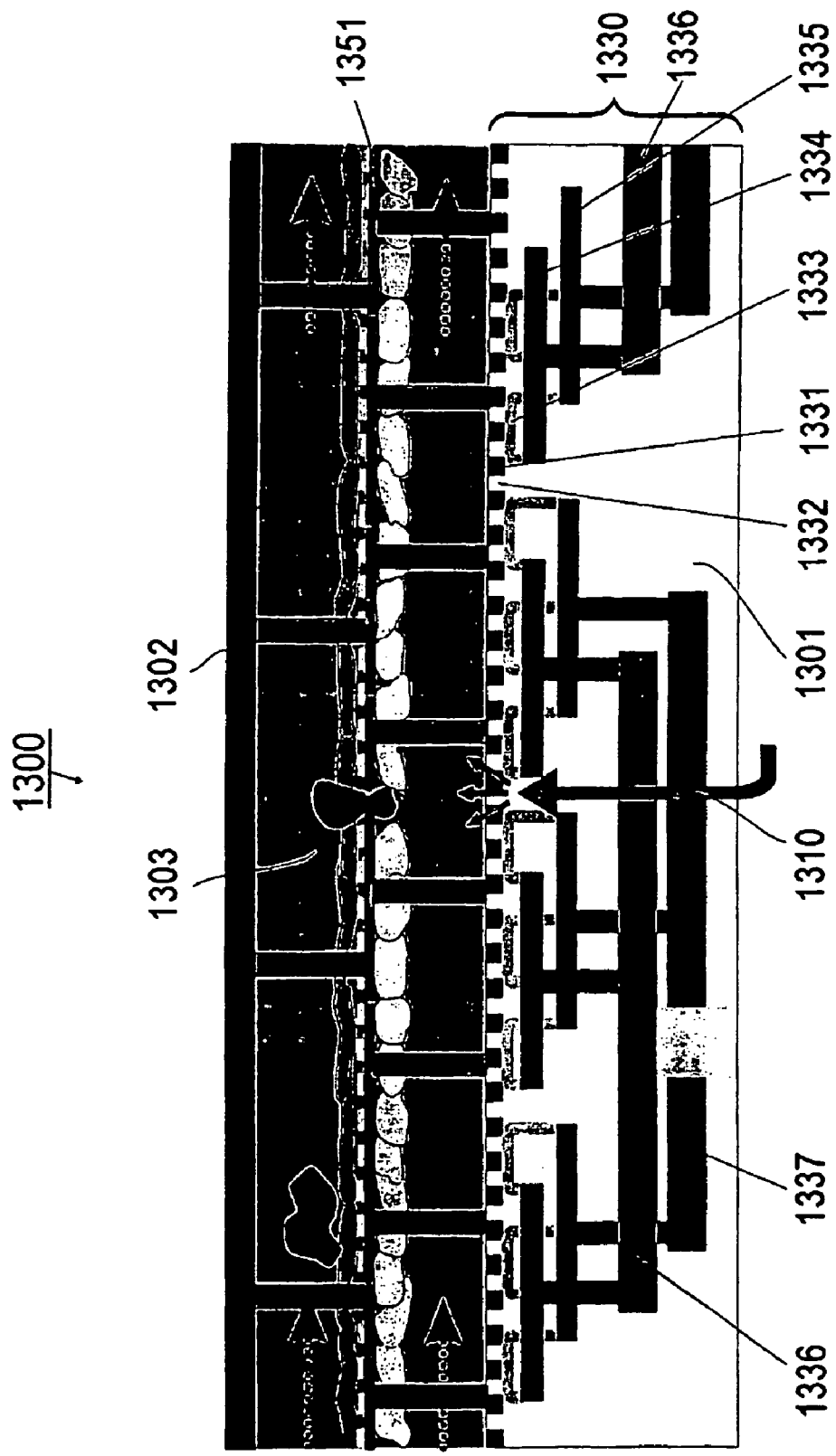
FIG. 13C shows a side cross-sectional view of a bioreactor with a two-chamber according to another embodiment of the present invention.
Figure 13D:
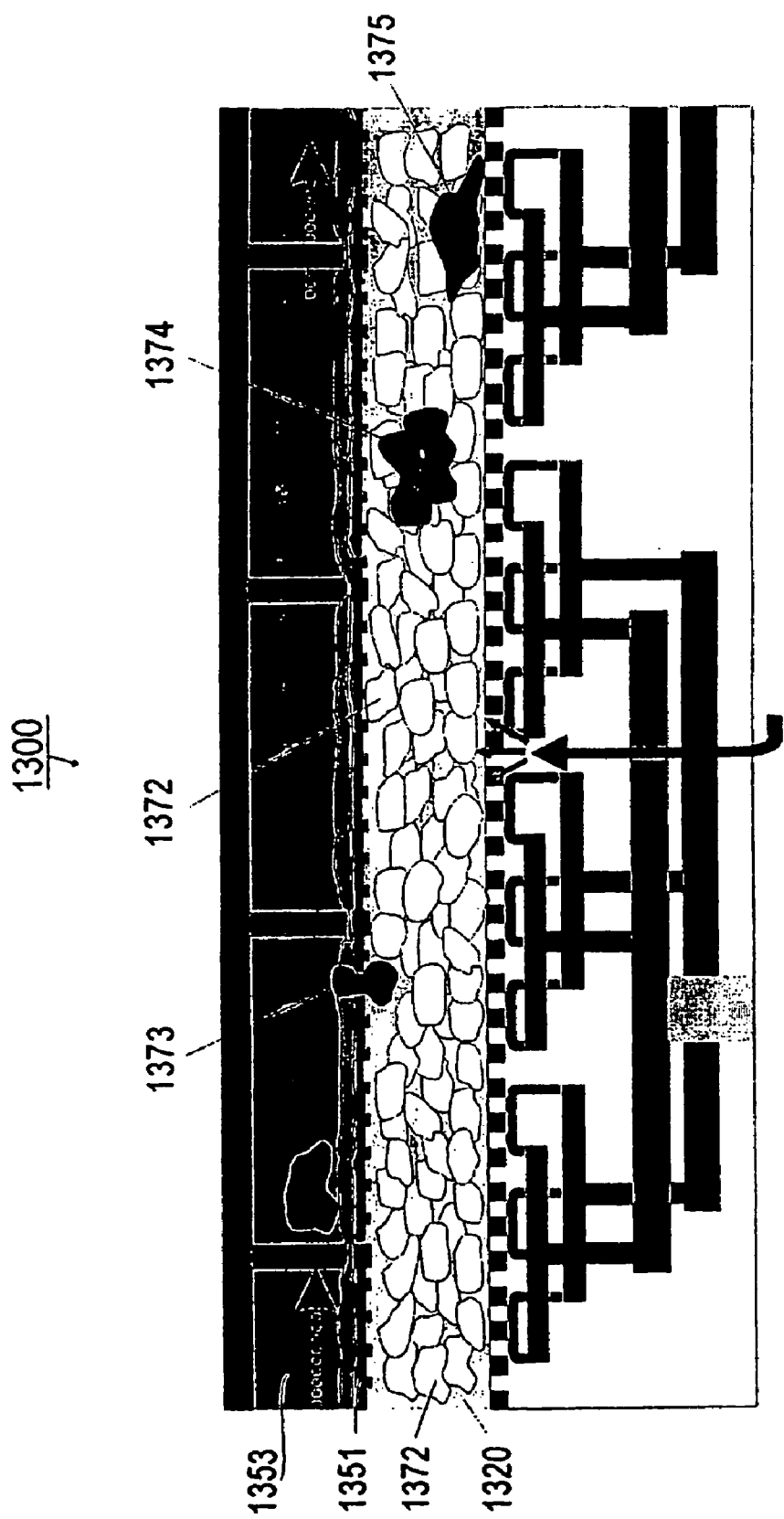
FIG. 13D shows a side cross-sectional view of a bioreactor with a single chamber according to one embodiment of the present invention.

In yet another embodiment, referring now to FIGS. 13C and 13D, in addition to the designs and structures set forth above particularly related to FIGS. 13A and 13B, a bioreactor 1300 further includes perfusion means 1330 in fluid communication with at least one of the first subchamber 1353 and the second subchamber 1354 to allow diffusional exchange of nutrients and metabolic byproducts with the chamber 1303.

Similar to the perfusion means 1230 discussed above related to embodiments as shown in FIGS. 12C and 12D, respectively, the perfusion means 1330 includes a second filter (or nanofilter) 1331 (the filter 1351 described above is considered as a first filter) with a plurality of pores 1332 in fluid communication with the second subchamber 1354, wherein the pores 1332 are sized to allow diffusional exchange of nutrients and metabolic byproducts with the second subchamber 1354 and not to allow cells to migrate across the second filter 1331. The pores 1332 of the second filter 1331, for example, can be sized to have a dimension smaller than 400 nanometers cross-sectionally. The first filter 1351 and the second filter 1331 can be same or different.

The perfusion means 1330 further includes a perfusion supply network in fluid communication with the second filter 1331 through the pores 1332. In one embodiment, the perfusion supply network includes a plurality of perfusion channels 1333, each being in fluid communication with the second filter 1331 to allow bi-directional, diffusional exchange of nutrients and metabolic byproducts with the second filter 1331 and being dimensioned to minimize pressure drops along each perfusion channel 1333 and to allow passive diffusional exchange of nutrients and metabolic byproducts along each perfusion channel 1333.

The perfusion supply network additionally includes a plurality of intermediate supply channels 1334, each being in fluid communication with a plurality of corresponding perfusion channel 1333 so as to provide perfusate to the plurality of corresponding perfusion channel 1333. Moreover, perfusion supply network includes a plurality of intermediate return channels 1335, each being in fluid communication with a plurality of corresponding perfusion channel 1333 so as to collect perfusate from the plurality of corresponding perfusion channel 1333.

Furthermore, the perfusion supply network includes a plurality of main supply channels 1336, each being in fluid communication with a plurality of corresponding intermediate supply channel 1334 so as to provide perfusate to the plurality of corresponding intermediate supply channel 1334, and a plurality of main return channels 1337, each being in fluid communication with a plurality of corresponding intermediate return channel 1337 so as to collect perfusate from the plurality of corresponding intermediate return channel 1337.

Figure 13E:
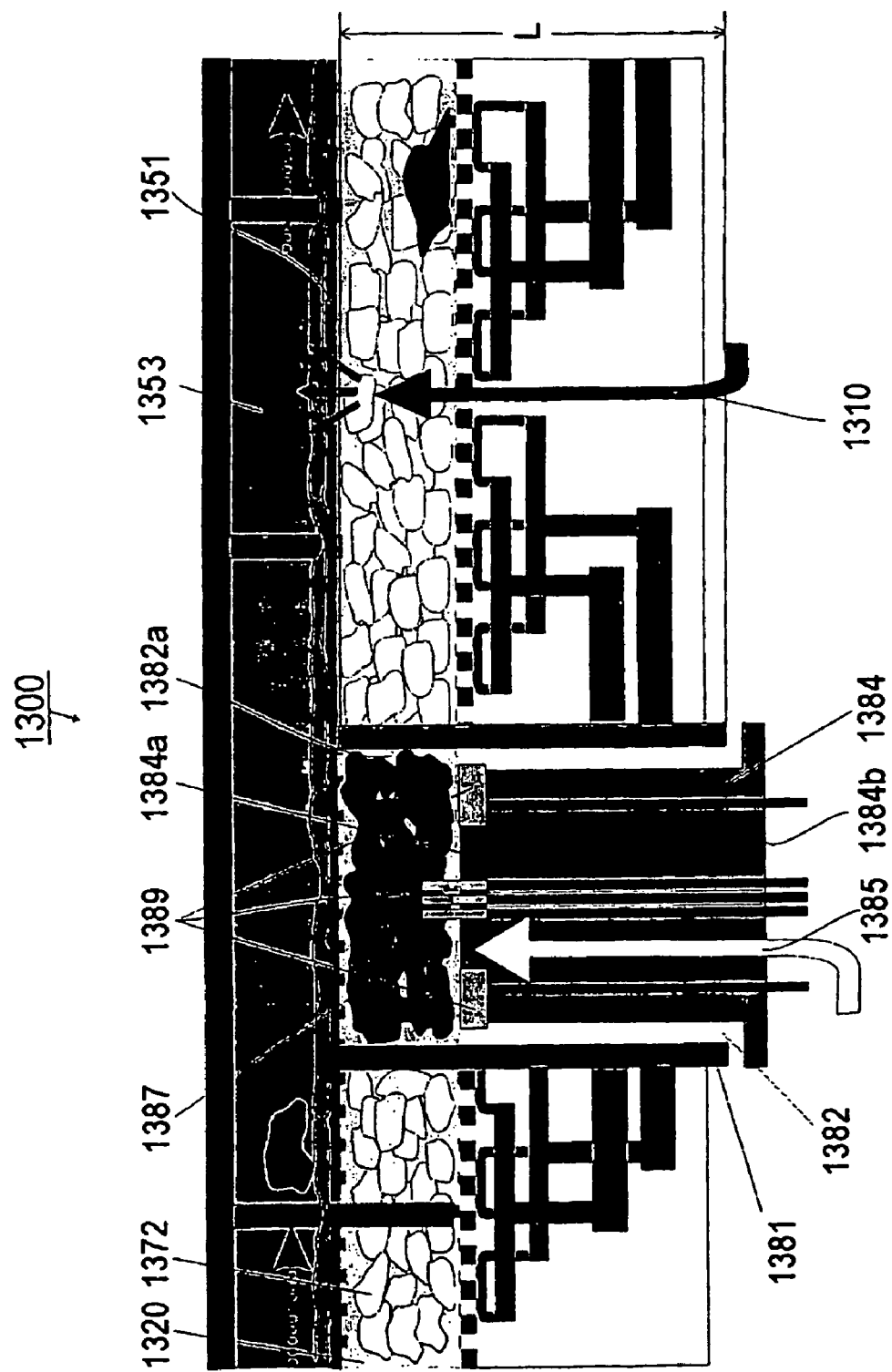
FIG. 13E shows a side cross-sectional view of a bioreactor with a single chamber according to another embodiment of the present invention.

This type of bioreactor with a microfabricated transwell chamber with chemokine injection capability as shown in FIGS. 13C and 13D, respectively, can be utilized to supported a coculture with filter perfusion to allow independent control of perfusion and shear in the chamber. The perfusion means 1330 maintains the viability of cells in the lower chamber 1354 independent of the flow in the upper chamber 1353. Stream of substances affecting growth of cells such as chemotactic agents can be injected through dedicated ports in the perfusion means 1330. Perfusion gradients can be created, for example, with appropriate parts of the perfusion supply network. This type of bioreactor allows, among other things, examination of intravasation, extravasation, and cell migration in solid tissue. For examples, as shown in FIG. 13D, a matrix 1372 of host cells may be cultured in collagen, matrigel, or other substrates in a tissue space 1320 (the lower chamber of the chamber 1303), a neutrophil or other cell 1373 may be extravasating from a vascular space (the upper chamber 1353 of the chamber 1303) into the tissue space 1320, one or more tumor cells 1374 grow in the tissue space 1320, and a macrophage or other cell 1375 in the tissue space 1320. Optionally, as shown in FIG. 13E, at least one insertion member 1381 defining a cavity 1382 therein is provided. The insertion member 1381 has a length L and is positioned through the second substrate 1301 and into the tissue space 1320 such that the cavity 1382 of the insertion member 1381 is in fluid communication with the first subchamber 1353 or the vascular space.

Correspondingly, a plug 1384 having a first surface 1384a and an opposite second surface 1384b is provided. The plug 1384 is complimentary to a corresponding insertion member 1381 such that when the plug 1384 is received into the cavity 1382 of the corresponding insertion member 1381, the plug 1384 engages with the body of the corresponding insertion member 1381 to seal the cavity 1382 and a volume 1382a is formed between the first surface 1384a and the first filter 1351 to allow a collection of cells to be received therein. For examples, a collection of tumor cells 1387 can be contained in the volume 1382a. Optionally, a cage adapted for separating the tumor cells 1387 from the first subchamber 1353 can be utilized.

Additionally, the plug 1384 further defines a port 1385 in fluid communication with the volume 1382a for injecting or withdrawing a stream of substance affecting the growth of the tumor cells 1387 such as chemokine. Moreover, a plurality of electrodes 1389 adapted for electrochemical measurements of the tumor cells 1387 can be utilized together with the plug 1384 to form a metabolic sensing head.

Figure 13F:
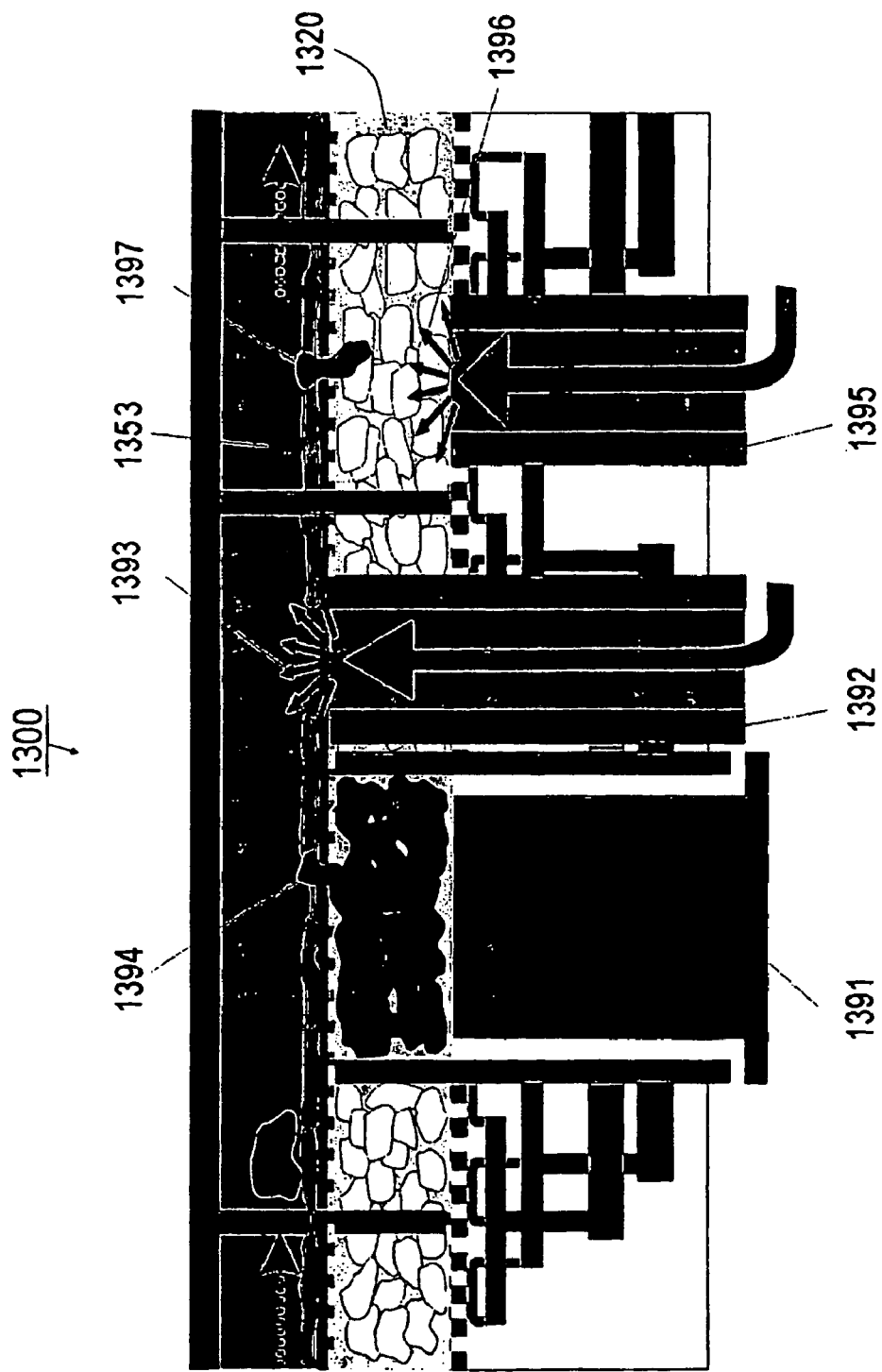
FIG. 13F shows a side cross-sectional view of a bioreactor with a single chamber according to yet another embodiment of the present invention.

In yet another alternative embodiment shown in FIG. 13F, a bioreactor 1300 is provided with an extension port member 1392 defining a channel therein. The extension port member 1392 is positioned such that the channel of the extension port member 1392 is in fluid communication with the first subchamber 1353 to allow a stream of substance is introduced to the first subchamber 1353 or the vascular space. For example, a gradient 1393 of chemokine can be introduced into the first subchamber 1353 or the vascular space. A similar structure 1395 can be utilized to provide a stream of substance such as a gradient 1396 of chemokine to the tissue space 1320.

This type of bioreactor allows, among other things, examination of intravasation, extravasation, and cell migration in solid tissue and is equipped for tumor cell or explant seeding and the delivery of chemokine in both the tissue and vascular space. The ability to add tumor cells or tumor blocks, removed from a target such as a mouse, to the host tissue matrix will provide metastasis assay that could be used in high throughput screening of anticancer drugs. Metabolic electrodes allow measurement of the local environment within the tumor. The tumor injection port 1391 provides control of the local tumor environment and the infusion of chemokine or drugs. Many other dynamics of cells can be observed. For examples, as shown in FIG. 13F, a tumor cell 1394 is seen to migrate out of the tissue space 1320 to the vascular space 1353, while another tumor cell 1397 may be extravasating from the vascular space 1353 into the tissue space 1320.

Nanofilter Fabrication and Perfusion Network

In the embodiment of various bioreactors of the present invention set forth above, at least some of them are shown with nanofilter, or nanopore filter, perfusion means or system and sensing elements for electrochemical detection. These components can be fabricated entirely using standard microfabrication techniques, including patterning, etching, thin film deposition, and soft-lithography techniques. Various fabrication methods in the art can be utilized. In one embodiment of the invention, soft lithography techniques are utilized to fabricate the devices using poly-dimethylsiloxane (PDMS) and replication molding[66,67]. The finished PDMS chip is fused to different PDMS modules for 3-dimensional bioreactors or rigid substrates (e.g., microscope cover slip, microelectrode bearing glass slide)[68]. PDMS is a biocompatible material with an oxygen permeability comparable to water[69].

One advantage of the perfusion through a nanopore filter is that the cells are perfused only by bidirectional diffusion through the membrane, not by mass-transport, so there is no shear. As shown in FIGS. 9(A-D), in one embodiment, the present invention provides a multi-layer fractal perfusion system 900 that ensures that chemokines released by cells in the matrix are not carried to other cells by the perfusion system— the perfusate which has been enriched by cell products is immediately carried away, where it cannot affect other cells and could also be analyzed without further dilution. Additionally, the perfusion network can be designed to provide a concentration gradient of a desired chemokine across the bioreactor.

Making of Perfusion Membrane. Polycarbonate filters with pore sizes below 400 nm can successfully block the passage of cells, as would be required for a cellular perfusion system wherein transfilter cellular migration was not desired. Typical filters with 10 to 400 nm diameter pores are six microns thick and have a pore density of approximately $6 \times 10^{12}$ to $1 \times 10^{12}$ pores/m$^2$; which corresponds to pore areas of 0.2% to 12% of the filter surface area, respectively. The low porosity of the filters with the smallest holes will limit their applicability for high efficiency diffusional transport that is driven only by a concentration gradient (in contrast to convective transport that can be driven by a high pressure differential across the filter). To create a perfusion system that relies only upon diffusion and hence eliminates shear forces, the present invention uses highly permeable nanopore filters with typical pore sizes of 10-100 nm that have not previously been used for cell culture. Patterns of this size cannot be generated by photolithography, but can be generated by self-assembly of block copolymer films[70]. The PS-b-PMMA copolymer has been shown suitable for self-generation of the pattern, and transfer of the pattern to silicon nitride, silicon oxide and silicon[61,71,72]. This polymer process produces polycrystalline, hexagonal close-packed arrays of pores with a mean pore diameter of 20 nm and center-to-center spacing of 42 nm. The standard deviation on each of these is about 10% in an optimized template. Typically, the uniformity does not degrade significantly through the pattern transfer and the reactive ion etching process required to convert a pattern in polymer to a filter in silicon nitride or alumina. Based upon the published data, the inventors make the conservative estimate of a final standard deviation of about 15%. The resulting porosity of these films is quite remarkable. The pore density can be estimated as follows: if e is the center-to-center distance between pores and we assume that for hexagonal close packing of three pores per unit cell, then the unit cell area is 3 $l^2 \sin(60°)$, and the pore density is $1/0.87 l^2$ or $1.15/l^2$. Using the 20 nm diameter and 42 nm separation, one has a pore density of $6.5 \times 10^{14}/m^2$ if the array has perfect, single-crystal hexagonal packing. Given the two-to-one relationship between pore separation and pore diameter, it follows that 67% of the membrane surface is covered by pores, a factor of 3,000 higher than can be achieved with standard polycarbonate filters with 20 nm pores. Defects may change these two numbers of course, but not by much. Hence 80 nm and 400 nm pore spacings can achieve pore densities of $1.8 \times 10^{14}$ and $7.2 \times 10^{12}$ pores/m$^2$, respectively, but will have the same fractional pore area.

Figure 9A:
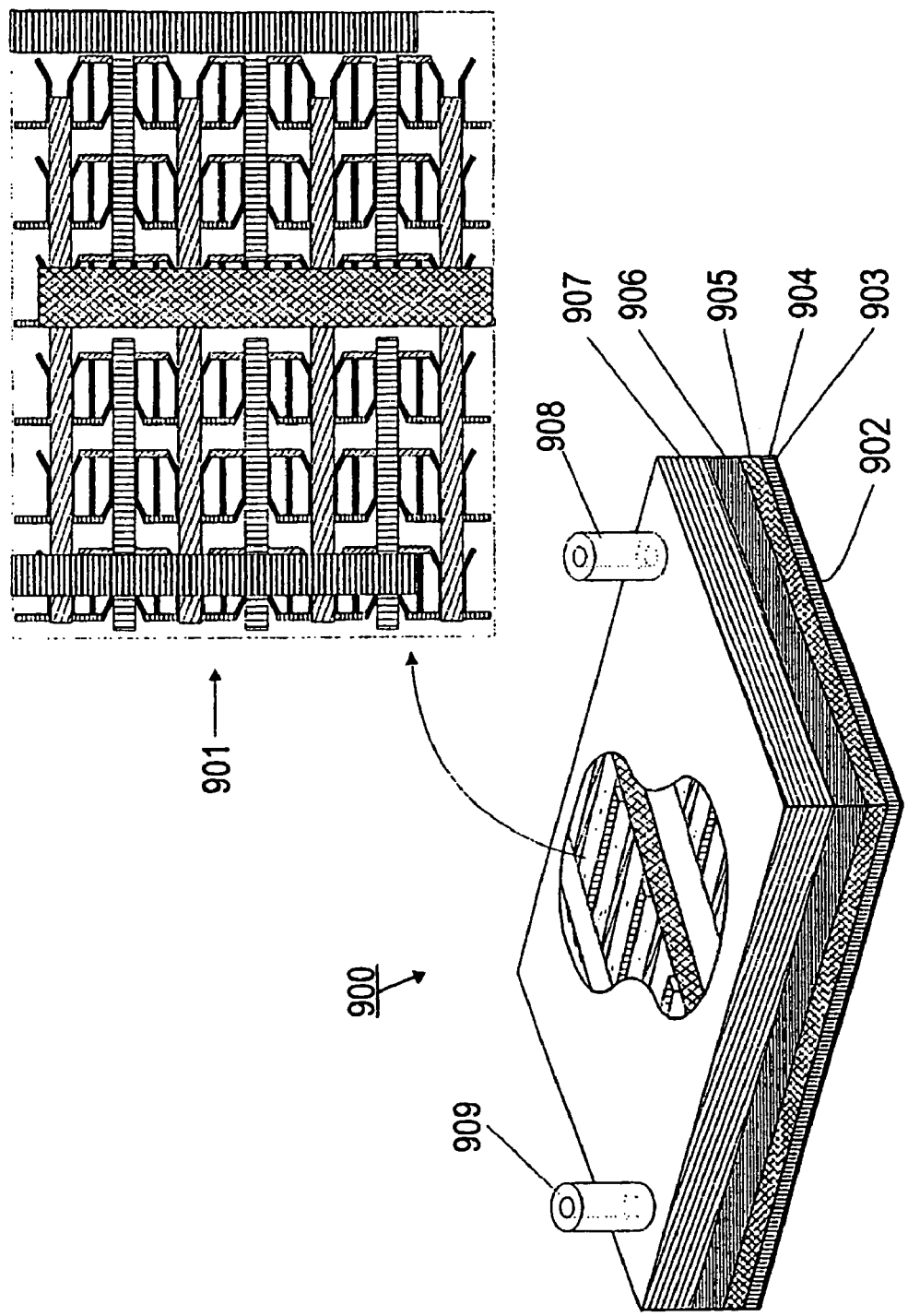
FIG. 9A shows a perspective view of a layered perfusion system according to one embodiment of the present invention: the insert, a cut-off top plan view.
Figure 9B:
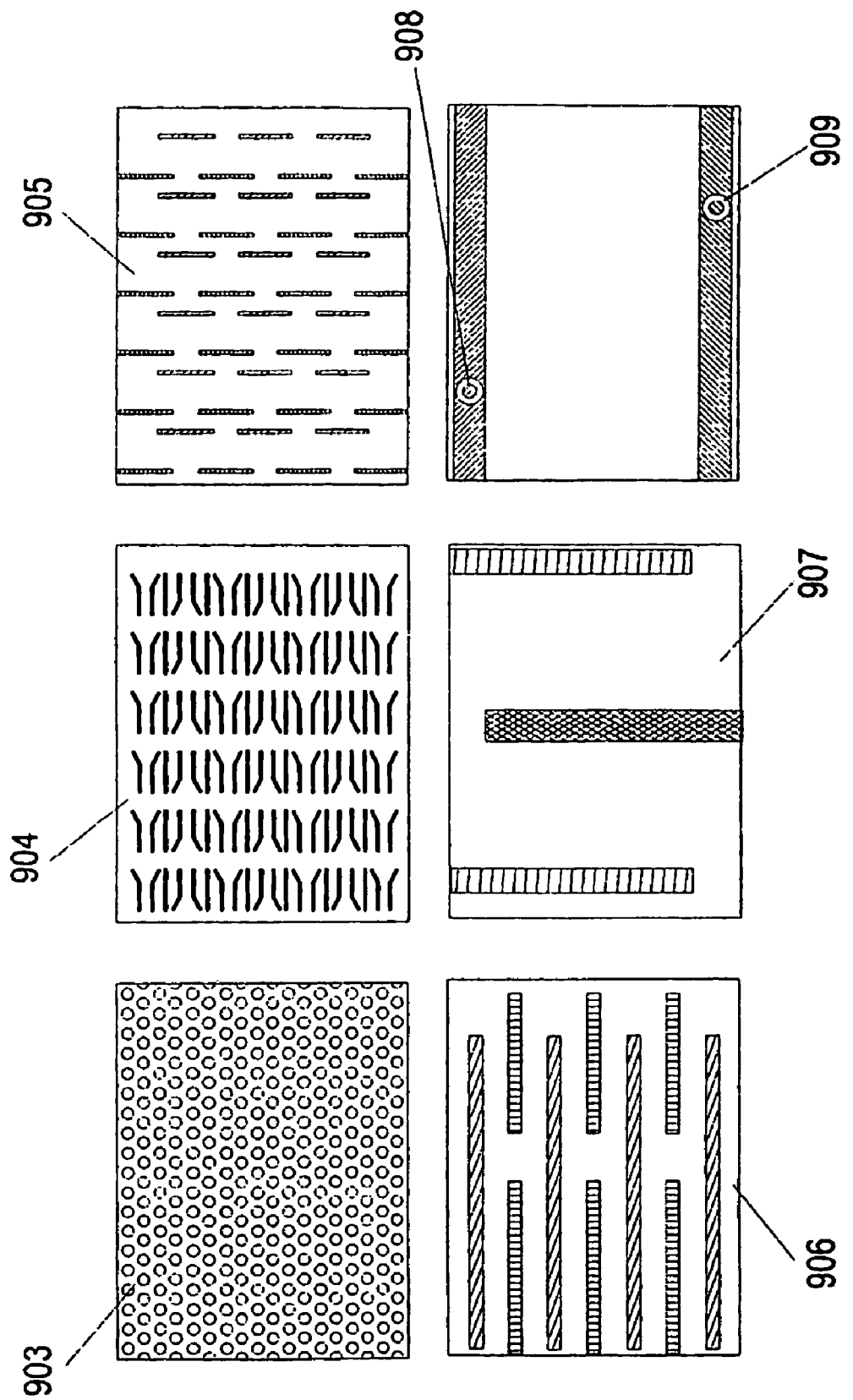
FIG. 9B shows a top view of different layers of a layered perfusion system as shown in FIG. 9A.
Figure 9C:
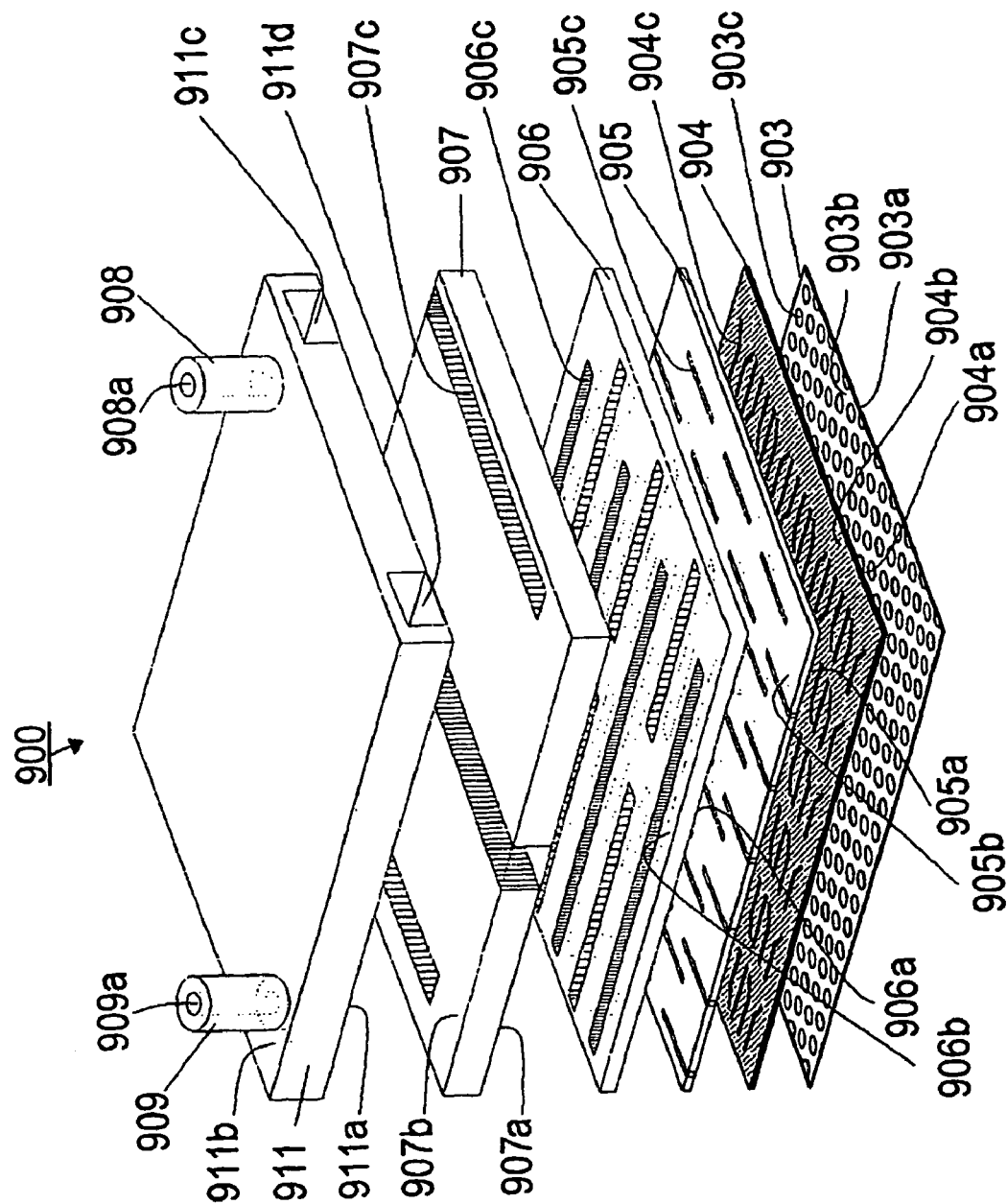
FIG. 9C shows an exploded view of a layered perfusion system as shown in FIG. 9A.
Figure 9F:
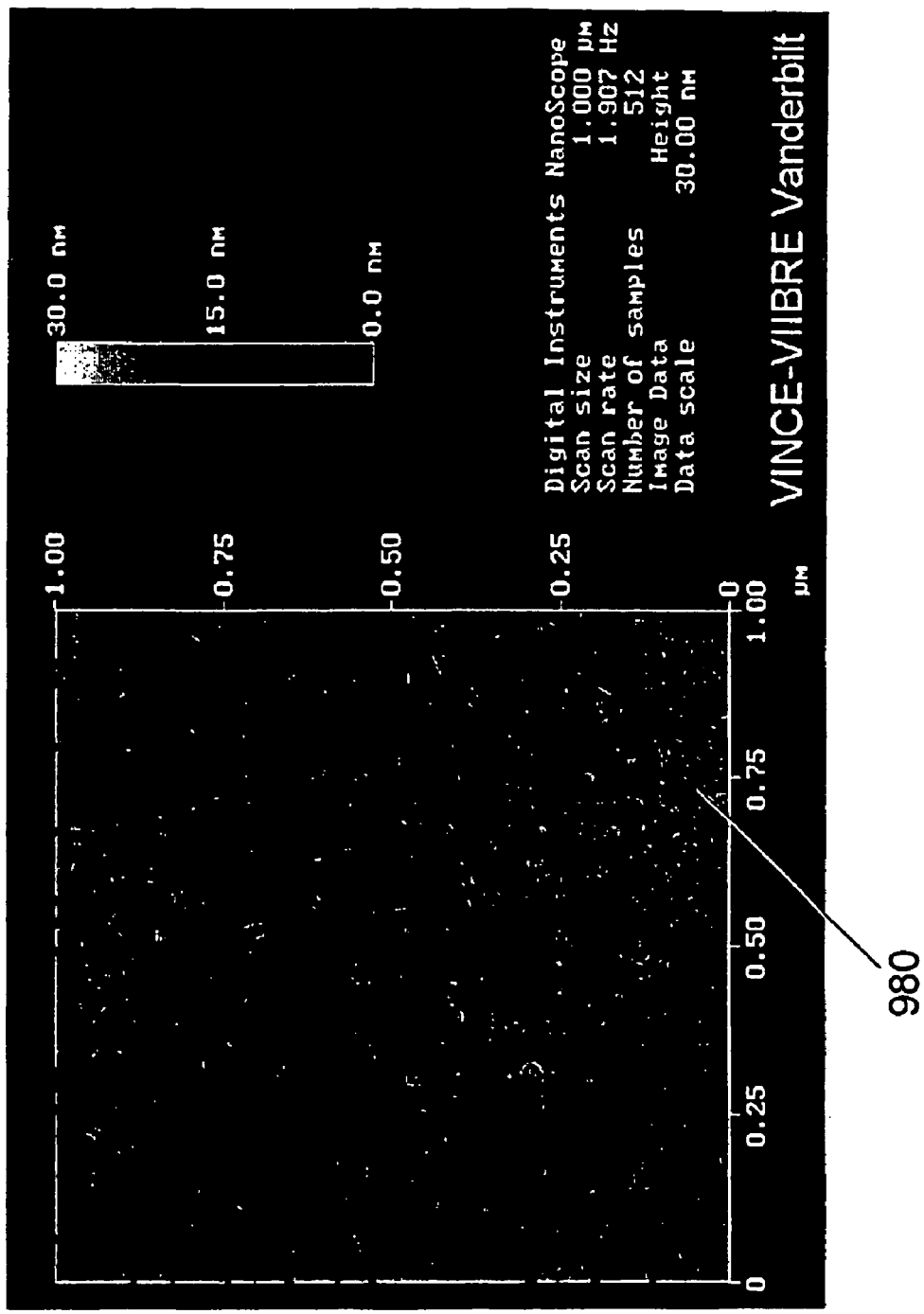
FIG. 9F shows an atomic force microscope image of a PS film template on a silicon wafer formed by spin casting a PS-b-PMMA film and removing the PMMA.

FIG. 9F shows an atomic force micrograph of a polystyrene-b-polymethylmethacrylate (PS-b-PMMA) pattern (with the PMMA removed) that the inventors have created on a silicon template. Patterns such as this are used to create the hole mask for the perfusion membrane to be fabricated on a silicon-nitride-coated, double-sided, polished silicon wafer by means of reactive ion etching. Photolithography is then be used to define a thin film Pt pattern for the capillary network on the opposite side of the silicon wafer. In a subsequent chemical etching step the silicon is removed where it is not protected by the metal film. Since the silicon nitride is inert it acts as an etch stop. This technique is generally used in MEMS fabrication and is well established. The net result is be a series of 10 µm wide by one millimeter long channels that are spanned by a sub-micron-thick silicon nitride film that has more that 60% of its area covered by uniform, 20 nm diameter pores. The 3,000-fold greater pore area and a membrane thickness that is $10^{-1}$-$10^{-2}$ that of the polycarbonate filter will provide a filter that is remarkably permeable to passive diffusional exchange as compared to conventional filters, yet has pore sizes that are sufficiently small to block cells from migrating across the filter. Two more scanning electron micrographs at two magnifications, image 970 for UV acet 3 06.TIF and image 972 for UV acet 3 11.TIF, of a PS-b-PMMA film deposited on silicon are shown in FIGS. 9E1 and 9E2, respectively.

Silicon nitride was chosen for the first membrane material because the fabrication of these structures has been demonstrated and the MEMS fabrication steps are well known. However, there may be advantages to using the polymer templates for membranes. For example, polymer membranes could be functionalized to enhance the growth of endothelial cells. A variety of structures are possible with self-assembly in numerous polymer systems: either by spinodal decomposition[73] or crystallization[74]. Other polymer systems will be surveyed and modeled for use as perfusion membranes and the most likely candidates selected for further study.

Making of Capillary Perfusion Network. The next step in building such a bioreactor is to connect one end of each of the short channels to perfusate supply and the other end to a drain. In one embodiment of the present invention, a novel, multilayer capillary perfusion network is utilized, where every layer of which contains an "arterial" branch for the delivery of culture media uniformly across the back of a filter membrane, and a "venous" branch to collect the solution that has undergone diffusional exchange with the cells on the other side. A 3-D network can be fabricated from stacked mylar layers. Fluid is injected at a single inlet, this inlet stream is split multiple times into an array of capillaries that cover the membrane, and the fluid is then gathered by the network back into a single outlet stream. Fluid entering the network has a multitude of path choices, and the key to providing uniform flow through the capillaries is to ensure that the flow resistance is identical through all of these possible paths. One design includes 4 layers of channels and one layer containing the inlet and outlet ports. This network takes fluid from the 0.5 mm square inlet and splits it into 51 capillaries, each of which is 50 microns square by 1100 microns long. The capillary array covers a membrane area that is 2.25 mm square, and the four channel layers, each formed by laser cutting of mylar sheets, have a total thickness of 750 microns. A larger area can be covered by tiling the membrane with this pattern and adding additional layers to join the pieces together. One feature of the network design is to split channels symmetrically and keep channels identical within a layer. The crossing of short channels simplifies alignment and mechanical support of the perfusion network, in that each layer maintains its structural rigidity. This approach works on all supporting channels but those on the outermost channels in the smallest-channel layers, which may have to be made narrower than the others on a layer in order to maintain (nearly) identical flow in each of the capillaries. To have the same flow in each capillary identical, the size of the capillaries must vary.

The elimination of shear forces can be accomplished by using only a high-permeability filter to separate the cells from a perfusion bath. The addition of the multilayer perfusion network of this invention offers a number of distinct advantages over this approach: It is possible to choose between uniform perfusion gradient perfusion by the choice of the perfusion network design or nutrient supply configuration, there is automatic separation of the supply from reaction products; the network provides distributed mechanical support of ultrathin membrane; chemokines can be introduced at edge or at an interior point in the array; it is possible to simulate regional annoxia by blocking channels at the arteriole level (either transiently or permanently), the separate perfusion and flow channels allow independent control of the cell delivery and cell perfusion systems; the capillary network could, in itself, be coated with endothelial cells; the network allows greater control of the perfusion environment as required for co-cultures; time-resolved exudate sampling is limited only by the time required for analytes to diffuse over short distances; there are no pressure gradients from bath convection or stirring; this approach provides a realistic model of tissue perfusion; it is possible to deliver drugs/toxins/nutrients capable of complex time modulation in a rapid and spatially-uniform manner; there is no mixing on input and output streams, and the perfusion network does not act as a macroscopic electrical short, but instead provides an anisotropic, short-scale coupling that can benefit either electroporation for delivery of genetic material, or the study of syncytial tissue such as the heart.

In one embodiment of the present invention, referring now to FIGS. 9(A-C), 9D1 and 9D2, respectively, a layered perfusion system 900 is provided for use in a bioreactor such as bioreactor 1300 as shown in FIG. 13C, where the bioreactor defines a chamber for receiving cells and liquid medium. The layered perfusion system 900 includes a filter 903, which is corresponding to the filter 1331 as shown in FIG. 13C, having a first surface 903a and an opposite, second surface 903b and a plurality of pores 903c defined therein. The layered perfusion system 900 further has a first perfusion system layer 904 having a first surface 904a and an opposite, second surface 904b and a plurality of perfusion channels 904c defined therein, where the first surface 904a of the first perfusion system layer 904 is received by the second surface 903b of the filter 903 such that each of the plurality of perfusion channels 904c is in fluid communication with the filter 903 to allow bi-directional, diffusional exchange of nutrients and metabolic byproducts with the filter 903 as shown in FIG. 9D1, where the flow 912 in a perfusion channel 904c is substantially in a direction A and the diffusion 913 cross the filter 903 through the pores 903c is bi-directional along a direction B, which is perpendicular to A. In other words, the diffusion can take place in a direction 913a out and in an opposite direction 913b in. Furthermore, each perfusion channel 904c is dimensioned to minimize pressure drops along each perfusion channel 904c and to allow passive diffusional exchange of nutrients and metabolic byproducts along each perfusion channel 904c.

The layered perfusion system 900 further has a second perfusion system layer 905 having a first surface 905a and an opposite, second surface 905b and a plurality of perfusion supply and return channels 905c defined therein, wherein the first surface 905a of the second perfusion system layer 904 is received by the second surface 904b of the first perfusion system layer 904 such that each of the plurality of perfusion supply and return channels 905c is in fluid communication with at least one of the plurality of perfusion channels 904c, and wherein the plurality of perfusion supply and return channels 904c are formed along a direction substantially perpendicular to that of the plurality of perfusion channels 904c.

The layered perfusion system 900 also has a third perfusion system layer 906 having a first surface 906a and an opposite, second surface 906b and a plurality of intermediate supply and return channels 906c defined therein, wherein the first surface 906a of the third perfusion system layer 906 is received by the second surface 905b of the second perfusion system layer 905 such that each of the plurality of intermediate supply and return channels 906c is in fluid communication with at least one of the plurality of perfusion supply and return channels 905c, and wherein the plurality of intermediate supply and return channels 906c are formed along a direction substantially perpendicular to that of the plurality of perfusion supply and return channels 905c.

The layered perfusion system 900 further has a fourth perfusion system layer 907 having a first surface 907a and an opposite, second surface 907b and a plurality of main supply and return channels 907c defined therein, wherein the first surface 907a of the fourth perfusion system layer 907 is received by the second surface 906b of the third perfusion system layer 906 such that each of the plurality of main supply and return channels 907c is in fluid communication with at least one of the plurality of intermediate supply and return channels 906c, and wherein the plurality of main supply and return channels 907c are formed along a direction substantially perpendicular to that of the plurality of intermediate supply and return channels 906c.

The layered perfusion system 900 additionally has a fifth perfusion system layer 911 having a first surface 911a and an opposite, second surface 911b and a supply channel 911c and a return channel 911d defined therein, wherein the first surface 911a of the fifth perfusion system layer 911 is received by the second surface 907b of the fourth perfusion system layer 907 such at both of supply and return channels 911c, 911d are in fluid communication with at least one of the plurality of main supply and return channels 907c, respectively and wherein the supply and return channels 911c, 911d are formed along a direction substantially perpendicular to that of the plurality of main supply and return channels 907c.

The layered perfusion system 900 further has a supply port 908 defining a channel 908a in fluid communication with the supply channel 911c, and a drain port 909 defining a channel 909a in fluid communication with the return channel 911d.

In use, the filter 903 is in fluid communication with the chamber of a bioreactor and each of the plurality of perfusion channels 904c is in fluid communication with the filter 903 to allow bi-directional, diffusional exchange of nutrients and metabolic byproducts with the chamber of the bioreactor through the pores 903c of the filter 903.

The pores 903c are sized to allow diffusional exchange of nutrients and metabolic byproducts with the chamber and not to allow cells to migrate across the filter 903, wherein the pores 903c of the second filter 903 are sized to have a dimension smaller than 400 nanometers cross-sectionally.

As such formed, the layered perfusion system 900 can be used as perfusion network 1330 in association with bioreactor 1300 as shown in FIG. 13C.

Referring now to FIG. 9D3 and FIGS. 9G(1-5), the present invention provides a method for preparing a layered perfusion system for use in a bioreactor. In one embodiment, the method includes arranging a silicon wafer 953, a silicon-nitride layer 952, and a coblock polymer layer 951 such that the silicon-nitride layer 952 is positioned between the silicon wafer 953 and the coblock polymer layer 951 to form a material 950, as shown in FIG. 9G1. Then a plurality of channels 904c are etched in the silicon wafer 953, as shown in FIG. 9G2. Then, the coblock polymer layer 951 is patterned to form a plurality of opening corresponding to positions where the plurality of pores 903c are to be formed, as shown in FIG. 9G2. Last, a plurality of pores 903c are etched through the silicon-nitride layer 952 to form a filter 903 such that the plurality of pores are in fluid communication with the plurality of channels 904c. The structure formed by this process is shown in FIG. 9G5.

While there has been shown various embodiments of the present invention, it is to be understood that certain changes can be made in the form and arrangement of the elements of the apparatus and steps of the methods to practice the present invention as would be known to one skilled in the art without departing from the underlying scope of the invention as is particularly set forth in the Claims. Furthermore, the embodiments described above are only intended to illustrate the principles of the present invention and are not intended to limit the claims to the disclosed elements. Indeed, since many embodiments of the invention can be made without departing from the spirit and scope of the invention, the invention resides in the claims hereinafter appended.

LIST OF REFERENCES

1. Godbey, W. T. and Atala, A., In Vitro Systems for Tissue Engineering, Ann. N.Y., Acad. Sci., 961, 10-26, 2002.

2. Murdin, A. D., Thorpe, J. S., Kirkby, N., Groves, D. J., Spier, R. E., Immobilisation and Growth of Hybridomas in Packed Beds, In: Bioreactors and biotransformations, Moody, G. W. and Baker, P. B., eds. Elsevier Applied Science Publishers, London, New York, 99-110, 1987.

3. De Bartolo, L., Jarosch-Von Schweder, G., Haverich, A., Bader, A., A Novel Full-Scale Flat Membrane Bioreactor Utilizing Porcine Hepatocytes: Cell Viability and Tissue-Specific Functions, Biotechnol. Prog., 16, 102-108, 2000.

4. McDuffie, N. G., Cell Culture Bioreactors. In: Bioreactor Design Fundamentals, Butterworth-Heinemann, Boston, 93-119, 1991.

5. Drioli, E, et al., Biocatalytic Membrane Reactors, Applications in Biotechnology and the Pharmaceutical Industry, Taylor & Francis, London, Philadelphia, 1999.

6. Labecki, M., Bowen, B. D., Piret, J. M., Protein Transport in Ultrafiltration Hollow-Fiber Bioreactors for Mammalian Cell Culture, In: Membrane Separations in Biotechnology, Wang, W. K., ed., M. Dekker, New York, 1-62, 2001.

7. Nollert, M. U., Diamond, S. L., McIntire, L. V., Hydrodynamic Shear-Stress and Mass-Transport Modulation of Endothelial-Cell Metabolism, Biotechnol. Bioeng., 38, 588-602, 1991.

8. Augenstein, D. C., Sinskey, A. J., Wang, D. I. C., Effect of Shear on Death of Two Strains of Mammalian Tissue Cells, Biotechnol. Bioeng., 13, 409-418, 1971.

9. Millward, H. R., Bellhouse, B. J., Sobey, I. J., The Vortex Wave Membrane Bioreactor: Hydrodynamics and Mass Transfer, Chemical Engineering Journal and the Biochemical Engineering Journal, 62, 175-181, 1996.

10. Beeton, S., Belihouse, B. J., Knowles, C. J., Millward, H. R., Nicholson, A. M., Wyatt, J. R., A Novel Membrane Bioreactor for Microbial-Growth, Appl. Microbiol. Biotechnol., 40, 812-817, 1994.

11. Hu, W. S. and Aunins, J. G., Large-Scale Mammalian Cell Culture, Curr. Opin. Biotechnol., 8, 148-153, 1997.

12. Tobert, W. R., Lewis, C. Jr., White, P. J., Feder, J., Perfusion Culture Systems for Production of Mammalian Cell Biomolecules, In: Large-Scale Mammalian cell culture, Feder, J. and Tolbert, W. R., eds., Academic Press, Orlando, 97-123, 1985.

13. Voisard, D., Meuwly, F., Ruffieux, P. A., Baer, G., Kadouri, A., Potential of Cell Retention Techniques for Large-Scale High-Density Perfusion Culture of Suspended Mammalian Cells, Biotechnol. Bioeng., 82, 751-765, 2003.

14. MacNeill, B. D., Pomerantseva, I., Lowe, H. C., Oesterle, S. N., Vacanti, J. P., Toward a New Blood Vessel, Vasc. Med., 7, 241-246, 2002.

15. Wu, H. K., Odom, T. W., Chiu, D. T., Whitesides, G. M., Fabrication of Complex Three-Dimensional Microchannel Systems in PDMS, J. Am. Chem. Soc., 125, 554-559, 2003.

16. Griffith, L. G., Emerging Design Principles in Biomaterials and Scaffolds for Tissue Engineering, Reparative Medicine: Growing Tissues and Organs, 961, 83-95, 2002.

17. Snyder, J. D. and Desai, T. A., Fabrication of Multiple Microscale Features on Polymer Surfaces for Applications in Tissue Engineering, Biomedical Microdevices, 3, 293-300, 2001.

18. Solan, A., Prabhakar, V., Niklason, L., Engineered Vessels: Importance of the Extracellular Matrix, Transplant. Proc., 33, 66-68, 2001.

19. Griffith, L. G. and Naughton, G., Tissue Engineering—Current Challenges and Expanding Opportunities, Science, 295, 1009-+, 2002.

20. Powers, M. J., Domansky, K., Kaazempur-Mofrad, M. R., Kalezi, A., Capitano, A., Upadhyaya, A., Kurzawski, P., Wack, K. E., Stolz, D. B., Kamm, R., Griffith, L. G., A Microfabricated Array Bioreactor for Perfused 3D Liver Culture, Biotechnol. Bioeng., 78, 257-269, 2002.

21. Park, T. H. and Shuler, M. L, Integration of Cell Culture and Microfabrication Technology, Biotechnol. Prog., 19, 243-253, 2003.

22. Borenstein, J. T., Terai, H., King, K. R., Weinberg, E. J., Kaazempur-Mofrad, M. R., Vacanti, J. P., Microfabrication Technology for Vascularized Tissue Engineering, Biomedical Microdevices, 4, 167-175, 2002.

23. Kaihara, S., Borenstein, J., Koka, R., Lalan, S., Ochoa, E. R., Ravens, M., Pien, H., Cunningham, B., Vacanti, J. P., Silicon Micromachining to Tissue Engineer Branched Vascular Channels for Liver Fabrication, Tissue Eng., 6, 105-117, 2000.

24. Allen, J. W. and Bhatia, S. N., Improving the Next Generation of Bioartificial Liver Devices, Seminars in Cell & Developmental Biology, 13, 447-454, 2002.

25. Passeraub, P. A, Almeida, A. C., Thakor, N. V., Design, Microfabrication and Analysis of a Microfluidic Chamber for the Perfusion of Brain Tissue Slices, Biomedical Microdevices, 5, 147-155, 2003.

26. Fink, C., Ergun, S., Kralisch, D., Remmers, U., Weil, J., Eschenhagen, T., Chronic Stretch of Engineered Heart Tissue Induces Hypertrophy and Functional Improvement, FASEB J., 14, 669-679, 2000.

27. Mooney, D. T., Mazzoni, C. L., Breuer, C., McNamara, K., Hem, D., Vacanti, J. P., Langer, R., Stabilized Polyglycolic Acid Fibre Based Tubes for Tissue Engineering, Biomaterials, 17, 115-124, 1996.

28. Boyden, S., The Chemotactic Effect of Mixtures of Antibody and Antigen on Polymorphonuclear Leucocytes, J. Exp. Med., 115, 453-466, 1962.

29. Harvath, L., Falk, W., Leonard, E. J., Rapid Quantitation of Neutrophil Chemotaxis—Use of A Polyvinylpyrrolidone-Free Polycarbonate Membrane in A Multiwell Assembly, J. Immunol. Methods, 37, 39-45, 1980.

30. Falk, W., Goodwin, R. H., Leonard, E. J., A 48-Well Micro Chemotaxis Assembly for Rapid and Accurate Measurement of Leukocyte Migration, J. Immunol. Methods, 33, 239-247, 1980.

31. Yao, J., Harvath, L., Gilbert, D. L., Colton, C. A., Chemotaxis by A Cns Macrophage, the Microglia, J. Neurosci. Res., 27, 36-42, 1990.

32. Roth, S. J., Carr, M. W., Rose, S. S., Springer, T. A., Characterization of Transendothelial Chemotaxis of T Lymphocytes, J. Immunol. Methods, 188, 97-116, 1995.

33. Klemke, R. L., Leng, J., Molander, R., Brooks, P. C., Vuori, K., Cheresh, D. A., CAS/Crk Coupling Serves As a "Molecular Switch" for Induction of Cell Migration, Journal of Cell Biology, 140, 961-972, 1998.

34. Ding, Z., Xiong, K., Issekutz, T. B., Chemokines Stimulate Human T Lymphocyte Transendothelial Migration to Utilize VLA-4 in Addition to LFA-1, J. Leukoc. Biol., 69, 458-466, 2001.

35. Jones, D. A., Abbassi, O., McIntire, L. V., McEver, R. P., Smith, C. W., P-Selectin Mediates Neutrophil Rolling on Histamine-Stimulated Endothelial Cells, Biophys. J., 65, 1560-1569, 1993.

36. Brown, D. and Larson, R., Improvements to Parallel Plate Flow Chambers to Reduce Reagent and Cellular Requirements, BMC Immunology, 2, 9-16, 2001.

37. Cinamon, G. and Alon, R., A Real Time in Vitro Assay for Studying Leukocyte Transendothelial Migration Under Physiological Flow Conditions, J. Immunol. Methods, 273, 53-62, 2003.

38. Renard, M., Heutte, F., Boutherin-Falson, O., Finet, M., Boisseau, M. R., Induced Changes of Leukocyte Slow Rolling in an in Flow Pharmacological Model of Adhesion to Endothelial Cells, Biorheology, 40, 173-178, 2003.

39. Munn, L. L., Melder, R. J., Jain, R. K., Analysis of Cell Flux in the Parallel-Plate Flow Chamber—Implications for Cell Capture Studies, Biophys. J., 67, 889-895, 1994.

40. Ley, K., The Selectins As Rolling Receptors. In: The selectins: initiators of leukocyte endothelial adhesion, Vestweber, D, ed. Harwood Academic Publishers, Australia, 63-104, 1997.

41. Papadaki, M. and McIntire, L. V., Quantitative Measurement of Shear-Stress Effects on Endothelial Cells. In: Tissue engineering methods and protocols, Morgan, J. R. and Yarmush, M. L., eds. Humana Press, Totowa, N.J., 577-593, 1999.

42. Ramos, C. L. and Lawrence, M. B., Quantitative Measurement of Cell-Cell Adhesion Under Flow Conditions, In: Tissue engineering methods and protocols, Morgan, J. R. and Yarmush, M. L., eds. Humana Press, Totowa, N.J., 507-519, 1999.

43. Hammer, D. A. and Brunk, D. K., Measuring Receptor-Mediated Cell Adhesion Under Flow: Cell-Free Systems. In: Tissue engineering methods and protocols, Morgan, J. R. and Yarmush, M. L., eds. Humana Press, Totowa, N.J., 543-552, 1999.

44. Jain, R. K., Munn, L. L., Fukumura, D., Melder, R. J., In Vitro and In Vivo Quantification of Adhesion Between Leukocytes and Vascular Endothelium. In: Tissue engineering methods and protocols, Morgan, J. R. and Yarmush, M. L., eds. Humana Press, Totowa, N.J., 553-575, 1999.

45. Li, C. Y., Shan, S., Huang, Q., Braun, R. D., Lanzen, J., Hu, K., Lin, P., Dewhirst, M. W., Initial Stages of Tumor Cell-Induced Angiogenesis: Evaluation Via Skin Window Chambers in Rodent Models, J Natl Cancer Inst, 92, 143-7, 2000.

46. Jain, R. K., Munn, L. L., Fukumura, D., Dissecting Tumour Pathophysiology Using Intravital Microscopy. Nat Rev Cancer, 2, 266-76, 2002.

47. Jain, R. K., Munn, L. L, Fukumura, D., Dissecting Tumour Pathophysiology Using Intravital Microscopy. Nature Reviews Cancer, 2, 266-276, 2002.

48. Jain, R. K., Angiogenesis and Lymphangiogenesis in Tumors: Insights From Intravital Microscopy, Cold Spring Harb. Symp. Quant. Biol., 67, 239-248, 2002.

49. Folkman, J., Bach, M., Rowe, J. W., Davidoff, F., Lambert, P., Hirsch, C., Goldberg, A., Hiatt, H. H., Glass, J., Henshaw, E., Tumor Angiogenesis—Therapeutic Implications, N. Engl. J. Med., 285, 1182-1186, 1971.

50. Weidner, N., Semple, J. P., Welch, W. R., Folkman, J., Tumor Angiogenesis and Metastasis—Correlation in Invasive Breast-Carcinoma, N. Engl. J. Med., 324, 1-8, 1991.

51. Lin, P., Buxton, J. A, Acheson, A, Radziejewski, C, Maisonpierre, P. C., Yancopoulos, G. D., Channon, K. M., Hale, L. P., Dewhirst, M. W., George, S. E., Peters, K. G., Antiangiogenic Gene Therapy Targeting the Endothelium-Specific Receptor Tyrosine Kinase Tie2, Proc. Natl Acad Sci USA, 95, 8829-34, 1998.

52. Lin, P., Polverini, P., Dewhirst, M., Shan, S., Rao, P. S., Peters, K., Inhibition of Tumor Angiogenesis Using a Soluble Receptor Establishes a Role for Tie2, in Pathologic Vascular Growth, J Clin Invest, 100, 2072-8, 1997.

53. Lin, P., Sankar, S., Shan, S., Dewhirst, M. W., Polverini, P. J., Quinn, T. Q., Peters, K. G., Inhibition of Tumor Growth by Targeting Tumor Endothelium Using a Soluble Vascular Endothelial Growth Factor Receptor, Cell Growth Differ, 9, 49-58, 1998.

54. Heidemann, J., Ogawa, H., Dwinell, M. B., Rafiee, P., Maaser, C., Gockel, H. R., Otterson, M. F., Ota, D. M., Lugering, N., Domschke, W., Binion, D. G., Angiogenic Effects of Interleukin 8 (CXCL8) in Human Intestinal Microvascular Endothelial Cells Are Mediated by CXCR2, J. Biol. Chem., 278, 8508-8515, 2003.

55. Li, Y., Tondravi, M., Liu, J., Smith, E., Haudenschild, C. C., Kaczmarek, M., Zhan, X., Cortactin Potentiates Bone Metastasis of Breast Cancer Cells, Cancer Res, 61, 6906-11, 2001.

56. Higgs, H. N. and Pollard, T. D., Regulation of Actin Filament Network Formation Through Alp2/3 Complex: Activation by a Diverse Array of Proteins, Annu. Rev. Biochem., 70, 649-676, 2001.

57. Li, F. Y., Zhang, L., Metzger, R. M., On the Growth of Highly Ordered Pores in Anodized Aluminum Oxide, Chem. Mater., 10, 2470-2480, 1998.

58. Li, A. P., Muller, F., Birner, A., Nielsch, K., Gosele, U., Hexagonal Pore Arrays With a 50-420 Nm Interpore Distance Formed by Self-Organization in Anodic Alumina, J. Appl. Phys., 84, 6023-6026, 1998.

59. Black, C. T., Guarini, K. W., Milkove, K. R., Baker, S. M., Russell, T. P., Tuominen, M. T., Integration of Self-Assembled Diblock Copolymers for Semiconductor Capacitor Fabrication, Appl. Phys. Lett., 79, 409-411, 2001.

60. Black, C. T. and Guarini, K. W., Diblock Copolymers: Self-Assembly for Applications in Microelectronics, In: Encyclopedia of Materials: Science and Technology, Buschow, K H J, ed. Elsevier, N.Y., 1-6, 2002.

61. Guarini, K. W., Black, C. T., Zhang, Y., Kim, H., Sikorski, E. M., Babich, I. V., Process Integration of Self-Assembled Polymer Templates into Silicon Nanofabrication, Journal of Vacuum Science & Technology B, 20, 2788-2792, 2002.

62. MartinezZaguilan, R., Seftor, E. A., Seftor, R. E. B., Chu, Y. W., Gillies, R. J., Hendrix, M. J. C., Acidic PH Enhances the Invasive Behavior of Human Melanoma Cells, Clinical & Experimental Metastasis, 14, 176-186, 1996.

63. Gillies, R. J., Raghunand, N., Karczmar, G. S., Bhujwalla, Z. M., MRI of the Tumor Microenvironment, J. Magn. Reson. Imaging, 16, 430-450, 2002.

64. Bhujwalla, Z. M., Artemov, D., Ballesteros, P., Cerdan, S., Gillies, R. J., Solaiyappan, M, Combined Vascular and Extracellular PH Imaging of Solid Tumors, NMR Biomed., 15, 114-119, 2002.

65. Helmlinger, G., Schell, A., Dellian, M., Forbes, N. S., Jain, R. K., Acid Production in Glycolysis-Impaired Tumors Provides New Insights into Tumor Metabolism, Clin. Cancer Res., 8, 1284-1291, 2002.

66. Whitesides, G. M., Ostuni, E, Takayama, S, Jiang, X. Y., Ingber, D. E., Soft Lithography in Biology and Biochemistry, Annual Review of Biomedical Engineering, 3, 335-373, 2001.

67. Xia, Y. N. and Whitesides, G. M., Soft Lithography, Annual Review of Materials Science, 28, 153-184, 1998.

68. Jackman, R. J. and Whitesides, G. M., Electrochemistry and Soft Lithography: A Route to 3-D, Chemtech, 29, 18-30, 1999.

69. McDonald, J. C. and Whitesides, G. M., Poly(Dimethylsiloxane) As a Material for Fabricating Microfluidic Devices, Accounts of Chemical Research, 35, 491-499, 2002.

70. Mansky, P., Liu, Y., Huang, E., Russell, T. P., Hawker, C., Controlling Polymer-Surface Interactions With Random Copolymer Brushes, Science, 275, 1458-1460, 1997.

71. Guarini, K. W., Black, C. T., Milkove, K. R., Sandstrom, R, L., Nanoscale Patterning Using Self-Assembled Polymers for Semiconductor Applications, J. Vac. Sci. & Tech. B, 19, 2784-2788, 2001.

72. Guarini, K. W., Black, C. T., Yeuing, S. H. I., Optimization of Diblock Copolymer Thin Film Self Assembly, Advanced Materials, 14, 1290-1294, 2002.

73. Walheim, S., Boltau, M., Mlynek, J., Krausch, G., Steiner, V., Structure Formation Via Polymer Demixing in Spin-Cast Films, Macromolecules, 30, 4995-5003, 1997.

74. Schultz, J. M., Roles of Solute and Heat-Flow in the Development of Polymer Microstructure, Polymer, 32, 3268-3283, 1991.

What is claimed is:

1. A bioreactor comprising:
 (a) a first substrate having a first surface, an opposite second surface and edges;
 (b) a second substrate having a first surface and an opposite second surface, defining a cavity with a bottom surface, wherein the bottom surface is located therebetween the first surface and the second surface, and wherein the first surface of the first substrate is received by the second surface of the second substrate to cover the cavity so as to form a chamber for receiving cells and a liquid medium; and
 (c) a port formed between the bottom surface and the first surface of the second substrate with a first opening and an opposite, second opening, wherein the port is in fluid communication with the chamber through the first opening to allow a, stream of substance to be introduced into the chamber through the port substantially along a first direction, wherein the second substrate further defines a third opening and an opposite fourth opening adapted for allowing a flow of liquid to be introduced into the chamber through the third opening and away from the chamber through the fourth opening substantially along a second direction, and wherein the second direction is substantially perpendicular to the first direction.

2. The bioreactor of claim 1, further comprising a biocompatible coating layer applied to the bottom surface of the second substrate.

3. The bioreactor of claim 2, wherein the biocompatible coating layer comprises a material that may inhibit cell adhesion to the biocompatible coating layer, enhance cell adhesion to the biocompatible coating layer, or function as a fluorescent marker or indicator of the state of cells.

4. The bioreactor of claim 2, wherein the first surface of the first substrate and the second surface of the second substrate is spaced such that when a layer of cells grows on the biocompatible coating layer, the flow of liquid can flow in the chamber between the first surface of the first substrate and the layer of cells.

5. The bioreactor of claim 4, wherein the flow of liquid is controlled so as to provide a known shear force to the layer of cells.

6. The bioreactor of claim 4, wherein the flow of liquid is controlled so as to provide perfusion and maintenance to the layer of cells.

7. The bioreactor of claim 4, wherein the cells comprise bacteria.

8. The bioreactor of claim 4, wherein the cells comprise protozoa.

9. The bioreactor of claim 4, wherein the cells comprise endothelial cells.

10. The bioreactor of claim 4, wherein the first surface of the first substrate and the second surface of the second substrate is spaced to further allow at least one cell to migrate above the layer of cells.

11. The bioreactor of claim 10, wherein the at least one cell to migrate is a cell different from the layer of cells.

12. The bioreactor of claim 11, wherein the at least one cell to migrate is a cell same as the layer of cells.

13. The bioreactor of claim 1, further comprising a layer of porous material positioned on the bottom surface of the second substrate.

14. The bioreactor of claim 13, further comprising a biocompatible coating layer applied to the layer of porous material such that the layer of porous material is between the biocompatible coating layer and the bottom surface of the second substrate.

15. The bioreactor of claim 2, wherein the biocompatible coating layer comprises a material that may inhibit cell adhesion to the biocompatible coating layer, enhance cell adhesion to the biocompatible coating layer, or function as a fluorescent marker or indicator of the state of cells.

16. The bioreactor of claim 2, wherein the first surface of the first substrate and the second surface of the second substrate are spaced such that when a layer of cells grows on the biocompatible coating layer, the flow of liquid can flow in the chamber between the first surface of the first substrate and the layer of cells.

17. The bioreactor of claim 16, wherein the flow of liquid is controlled so as to provide a known shear force to the layer of cells.

18. The bioreactor of claim 17, wherein the flow of liquid is controlled so as to provide perfusion and maintenance to the layer of cells.

19. The bioreactor of claim 17, wherein the cells comprise bacteria.

20. The bioreactor of claim 17, wherein the cells comprise protozoa.

21. The bioreactor of claim 16, wherein the cells comprise endothelial cells.

22. The bioreactor of claim 16, wherein the first surface of the first substrate and the second surface of the second substrate are spaced to further allow at least one cell to migrate above the layer of cells.

23. The bioreactor of claim 22, wherein the at least one cell to migrate is a cell different from the layer of cells.

24. The bioreactor of claim 23, wherein the at least one cell to migrate is a cell same as the layer of cells.

25. The bioreactor of claim 13, wherein the layer of porous material comprises collagen.

26. The bioreactor of claim 13, wherein the layer of porous material comprises an extracellular matrix.

27. The bioreactor of claim 13, wherein the layer of porous material comprises at least one cell culture scaffold supportive to the layer of cells.

28. The bioreactor of claim 13, wherein the layer of porous material allows at least one cell to extravasate below the layer of cells.

29. The bioreactor of claim 1, wherein the second substrate is fabricated from glass, Mylar, PDMS, silicon, a polymer, a semiconductor, or any combination of them.

30. The bioreactor of claim 1, wherein the first substrate is at least partially optically transparent.

31. The bioreactor of claim 30, further comprising a plurality of posts positioned between the first surface of the first substrate and the second surface of the second substrate to substantially maintain a predetermined separation between the first surface of the first substrate and the second surface of the second substrate to allow optical detecting of dynamic activities of cells in the chamber.

32. The bioreactor of claim 31, wherein the dynamic activities of cells in the chamber are detectable through optical detecting means.

33. The bioreactor of claim 32, wherein the optical detecting means comprises at least one of high-resolution optical microscope and a fluorescence-imaging device.

34. The bioreactor of claim 31, wherein the plurality of posts are positioned in at least two rows, and wherein each row of posts has at least two posts spaced from each other.

35. The bioreactor of claim 31, wherein the first substrate and the second substrate are substantially parallel to each other.

36. The bioreactor of claim 30, further comprising a biocompatible coating layer applied to the first surface of the first substrate.

37. The bioreactor of claim 36, wherein the biocompatible coating layer comprises a material that may inhibit cell adhesion to the biocompatible coating layer, enhance cell adhesion to the biocompatible coating layer, or function as a fluorescent marker or indicator of the state of cells.

38. The bioreactor of claim 1, wherein the stream of substance is controlled so as to provide a gradient to the chamber at least around the first opening.

39. The bioreactor of claim 38, wherein the stream of substance comprises chemokine.

40. The bioreactor of claim 39, wherein the stream of substance comprises a substance affecting the growth of cells.

41. A bioreactor comprising:
(a) a first substrate having a first surface, an opposite second surface and edges;
(b) a second substrate having a first surface and an opposite second surface, defining a cavity with a bottom surface, wherein the bottom surface is located therebetween the first surface and the second surface, and wherein the first surface of the first substrate is received by the second surface of the second substrate to cover the cavity so as to form a chamber for receiving cells and a liquid medium; and
(c) perfusion means in fluid communication with the chamber to allow diffusional exchange of nutrients and metabolic byproducts with the chamber.

42. The bioreactor of claim 41, further comprising a port formed between the bottom surface and the first surface of the second substrate with a first opening and an opposite, second opening, wherein the port is in fluid communication with the chamber through the first opening to allow a stream of substance to be introduced into the chamber through the port substantially along a first direction.

43. The bioreactor of claim 42, wherein the second substrate further defines a third opening and an opposite fourth opening adapted for allowing a flow of liquid to be introduced into the chamber through the third opening and away from the chamber through the fourth opening substantially along a second direction, and wherein the second direction is substantially perpendicular to the first direction.

44. The bioreactor of claim 43, further comprising a biocompatible coating layer applied to the bottom surface of the second substrate.

45. The bioreactor of claim 44, wherein the biocompatible coating layer comprises a material that may inhibit cell adhesion to the biocompatible coating layer, enhance cell adhesion to the biocompatible coating layer, or function as a fluorescent marker or indicator of the state of cells.

46. The bioreactor of claim 44, wherein the first surface of the first substrate and the second surface of the second substrate is spaced such that when a layer of cells grows on the biocompatible coating layer, the flow of liquid can flow in the chamber between the first surface of the first substrate and the layer of cells.

47. The bioreactor of claim 46, wherein the flow of liquid is controlled so as to provide a known shear force to the layer of cells.

48. The bioreactor of claim 46, wherein the flow of liquid is controlled so as to provide perfusion and maintenance to the layer of cells.

49. The bioreactor of claim 46, wherein the cells comprise bacteria.

50. The bioreactor of claim 46, wherein the cells comprise protozoa.

51. The bioreactor of claim 46, wherein the cells comprise endothelial cells.

52. The bioreactor of claim 46, wherein the first surface of the first substrate and the second surface of the second substrate is spaced to further allow at least one cell to migrate above the layer of cells.

53. The bioreactor of claim 52, wherein the at least one cell to migrate is a cell different from the layer of cells.

54. The bioreactor of claim 53, wherein the at least one cell to migrate is a cell same as the layer of cells.

55. The bioreactor of claim 43, further comprising a layer of porous material positioned on the bottom surface of the second substrate.

56. The bioreactor of claim 55, further comprising a biocompatible coating layer applied to the layer of porous material such that the layer of porous material is between the biocompatible coating layer and the bottom surface of the second substrate.

57. The bioreactor of claim 56, wherein the biocompatible coating layer comprises a material that may inhibit cell adhesion to the biocompatible coating layer, enhance cell adhesion to the biocompatible coating layer, or function as a fluorescent marker or indicator of the state of cells.

58. The bioreactor of claim 56, wherein the first surface of the first substrate and the second surface of the second substrate is spaced such that when a layer of cells grows on the biocompatible coating layer, the flow of liquid can flow in the chamber between the first surface of the first substrate and the layer of cells.

59. The bioreactor of claim 58, wherein the flow of liquid is controlled so as to provide a known shear force to the layer of cells.

60. The bioreactor of claim 59, wherein the flow of liquid is controlled so as to provide perfusion and maintenance to the layer of cells.

61. The bioreactor of claim 60, wherein the cells comprise bacteria.

62. The bioreactor of claim 60, wherein the cells comprise protozoa.

63. The bioreactor of claim 60, wherein the cells comprise endothelial cells.

64. The bioreactor of claim 60, wherein the first surface of the first substrate and the second surface of the second substrate is spaced to further allow at least one cell to migrate above the layer of cells.

65. The bioreactor of claim 64, wherein the at least one cell to migrate is a cell different from the layer of cells.

66. The bioreactor of claim 65, wherein the at least one cell to migrate is a cell same as the layer of cells.

67. The bioreactor of claim 55, wherein the layer of porous material comprises collagen.

68. The bioreactor of claim 55, wherein the layer of porous material comprises an extracellular matrix.

69. The bioreactor of claim 55, wherein the layer of porous material comprises at least one cell culture scaffold supportive to the layer of cells.

70. The bioreactor of claim 55, wherein the layer of porous material allows at least one cell to extravasate below the layer of cells.

71. The bioreactor of claim 42, wherein the stream of substance is controlled so as to provide a gradient to the chamber at least around the first opening.

72. The bioreactor of claim 71, wherein the stream of substance comprises chemokine.

73. The bioreactor of claim 71, wherein the stream of substance comprises a substance affecting the growth of cells.

74. The bioreactor of claim 41, wherein the second substrate is fabricated from glass, Mylar, PDMS, silicon, a polymer, a semiconductor, or any combination of them.

75. The bioreactor of claim 41, wherein the first substrate is at least partially optically transparent.

76. The bioreactor of claim 75, further comprising a plurality of posts positioned between the first surface of the first substrate and the second surface of the second substrate to substantially maintain a predetermined separation between the first surface of the first substrate and the second surface of the second substrate to allow optical detecting of dynamic activities of cells in the chamber.

77. The bioreactor of claim 76, wherein the dynamic activities of cells in the chamber are detectable through optical detecting means.

78. The bioreactor of claim 77, wherein the optical detecting means comprises at least one of high-resolution optical microscope and a fluorescence-imaging device.

79. The bioreactor of claim 76, wherein the plurality of posts are positioned in at least two rows, and wherein each row of posts has at least two posts spaced from each other.

80. The bioreactor of claim 76, wherein the first substrate and the second substrate are substantially parallel to each other.

81. The bioreactor of claim 75, further comprising a biocompatible coating layer applied to the first surface of the first substrate.

82. The bioreactor of claim 81, wherein the biocompatible coating layer comprises a material that may inhibit cell adhesion to the biocompatible coating layer, enhance cell adhesion to the biocompatible coating layer, or function as a fluorescent marker or indicator of the state of cells.

83. The bioreactor of claim 41, wherein the perfusion means comprises:
(a) a nanofilter with a plurality of pores in fluid communication with the chamber, wherein the pores are sized to allow diffusional exchange of nutrients and metabolic byproducts with the chamber and not to allow cells to migrate across the nanofilter; and
(b) a perfusion supply network in fluid communication with the nanofilter through the pores.

84. The bioreactor of claim 83, wherein the pores are further sized to allow cells to perfuse through only by bi-directional diffusion through the nanofilter in a manner such that substantially no shear is generated by the perfusion of cells.

85. The bioreactor of claim 84, wherein the perfusion supply network comprises:
(a) a plurality of perfusion channels, each being in fluid communication with the nanofilter to allow bi-directional, diffusional exchange of nutrients and metabolic byproducts with the nanofilter and being dimensioned to minimize pressure drops along each perfusion channel and to allow passive diffusional exchange of nutrients and metabolic byproducts along each perfusion channel;
(b) a plurality of intermediate supply channels, each being in fluid communication with a plurality of corresponding perfusion channels so as to provide perfusate to the plurality of corresponding perfusion channels; and
(c) a plurality of intermediate return channels, each being in fluid communication with a plurality of corresponding perfusion channels so as to collect perfusate from the plurality of corresponding perfusion channels.

86. The bioreactor of claim 85, wherein the perfusion supply network further comprises:
(a) a plurality of main supply channels, each being in fluid communication with a plurality of corresponding intermediate supply channels so as to provide perfusate to the plurality of corresponding intermediate supply channels; and
(b) a plurality of main return channels, each being in fluid communication with a plurality of corresponding intermediate return channels so as to collect perfusate from the plurality of corresponding intermediate return channels.

87. The bioreactor of claim 83, wherein the pores of the nanofilter are sized to have a dimension smaller than 400 nanometers cross-sectionally.

88. A bioreactor comprising:
(a) a first substrate having a first surface, an opposite second surface and edges;
(b) a second substrate having a first surface and an opposite second surface, defining a cavity with a bottom surface, wherein the bottom surface is located therebetween the first surface and the second surface, and wherein the first surface of the first substrate is received by the second surface of the second substrate to cover the cavity so as to form a chamber for receiving cells and a liquid medium;
(c) a filter dividing the chamber into a first subchamber and a second subchamber, wherein the filter has a porosity to allow the first subchamber and the second subchamber in fluid communication; and
(d) a port formed between the bottom surface and the first surface of the second substrate with a first opening and an opposite, second opening, wherein the port is in fluid communication with the second subchamber through the first opening to allow a stream of substance to be introduced into the chamber through the port substantially along a first direction.

89. The bioreactor of claim 88, wherein the second substrate further defines a third opening and an opposite fourth opening adapted for allowing a flow of liquid to be introduced into at least one of the first subchamber and the second subchamber through the third opening and away from at least one of the first subchamber and the second subchamber through the fourth opening substantially along a second direction, and wherein the second direction is substantially perpendicular to the first direction.

90. The bioreactor of claim 89, wherein the filter has a first surface that defines the first subchamber with the first surface of the first substrate, and an opposite second surface that defines the second subchamber with the second surface of the second substrate.

91. The bioreactor of claim 90, wherein the filter comprises a perfusion membrane with a plurality of pores in fluid communication with at least one of the first subchamber and the second subchamber, wherein the pores are sized to allow diffusional exchange of nutrients and metabolic byproducts with at least one of the first subchamber and the second subchamber and not to allow cells to migrate across the filter.

92. The bioreactor of claim 91, wherein the pores are further sized to allow cells to perfuse through only by bi-directional diffusion through the filter in a manner such that substantially no shear is generated by the perfusion of cells.

93. The bioreactor of claim 92, wherein the pores of the filter are sized to have a dimension smaller than 400 nanometers cross-sectionally.

94. The bioreactor of claim 90, further comprising a plurality of posts positioned between the first surface of the first substrate and the first surface of the filter to substantially maintain a predetermined separation between the first surface of the first substrate and the first surface of the filter to allow optical detecting of dynamic activities of cells in the first subchamber.

95. The bioreactor of claim 94, further comprising a plurality of posts positioned between the second surface of the second substrate and the second surface of the filter to substantially maintain a predetermined separation between the second surface of the second substrate and the second surface of the filter to allow optical detecting of dynamic activities of cells in the second subchamber.

96. The bioreactor of claim 95, wherein the plurality of posts are positioned in at least two rows, and wherein each row of posts has at least two posts spaced from each other.

97. The bioreactor of claim 95, wherein when a first flow of liquid is introduced into the first subchamber, the first flow of liquid is controlled so as to provide a known shear force to a first layer of cells growing in the first subchamber on the first surface side of the filter and an environment that simulates a vascular space in the first subchamber.

98. The bioreactor of claim 97, wherein when a second flow of liquid is introduced into the second subchamber, the second flow of liquid is controlled so as to provide an environment that simulates a tissue space in the second subchamber.

99. The bioreactor of claim 98, wherein the first flow of liquid and the second flow of liquid are different.

100. The bioreactor of claim 97, wherein a second layer of cells is capable of growing in the second subchamber on the second surface side of the filter.

101. The bioreactor of claim 100, wherein the first layer of cells growing in the first subchamber and the second layer of cells growing in the second subchamber are different.

102. The bioreactor of claim 89, further comprising an extension port member defining a channel therein, wherein the extension port member is positioned complimentary to the port such that the channel of the extension port member is in fluid communication with the port and the first subchamber to allow the stream of substance is introduced to the first subchamber.

103. The bioreactor of claim 88, wherein the second substrate is fabricated from glass, Mylar, PDMS, silicon, a polymer, a semiconductor, or any combination of them.

104. The bioreactor of claim 88, wherein the first substrate is at least partially optically transparent.

105. The bioreactor of claim 88, wherein the stream of substance is controlled so as to provide a gradient to the chamber at least around the first opening.

106. The bioreactor of claim 105, wherein the stream of substance comprises chemokine.

107. The bioreactor of claim 105, wherein the stream of substance comprises a substance affecting the growth of cells.

108. A bioreactor comprising:
(a) a first substrate having a first surface, an opposite second surface and edges;
(b) a second substrate having a first surface and an opposite second surface, defining a cavity with a bottom surface, wherein the bottom surface is located therebetween the first surface and the second surface, and wherein the first surface of the first substrate is received by the second surface of the second substrate to cover the cavity so as to form a chamber for receiving cells and a liquid medium;
(c) a first filter dividing the chamber into a first subchamber and a second subchamber, wherein the first filter has a porosity to allow the first subchamber and the second subchamber in fluid communication;
(d) perfusion means in fluid communication with at least one of the first subchamber and the second subchamber to allow diffusional exchange of nutrients and metabolic byproducts with the chamber; and
(e) a port formed between the bottom surface and the first surface of the second substrate with a first opening and an opposite, second opening, wherein the port is in fluid communication with the second subchamber through the first opening to allow a stream of substance to be introduced into the chamber through the port substantially along a first direction.

109. The bioreactor of claim 108, further comprising a port formed between the bottom surface and the first surface of the second substrate with a first opening and an opposite, second opening, wherein the port is in fluid communication with the second subchamber through the first opening to allow a stream of substance to be introduced into the chamber through the port substantially along a first direction.

110. The bioreactor of claim 109, wherein the second substrate further defines a third opening and an opposite fourth opening adapted for allowing a flow of liquid to be introduced into at least one of the first subchamber and the second subchamber through the third opening and away from at least one of the first subchamber and the second subchamber through the fourth opening substantially along a second direction, and wherein the second direction is substantially perpendicular to the first direction.

111. The bioreactor of claim 108, wherein the first filter has a first surface that defines the first subchamber with the first surface of the first substrate, and an opposite second surface that defines the second subchamber with the second surface of the second substrate.

112. The bioreactor of claim 111, wherein the first filter comprises a perfusion membrane with a plurality of pores in fluid communication with at least one of the first subchamber and the second subchamber, wherein the pores are sized to allow diffusional exchange of nutrients and metabolic byproducts with at least one of the first subchamber and the second subchamber and not to allow cells to migrate across the first filter.

113. The bioreactor of claim 112, wherein the pores are further sized to allow cells to perfuse through only by bi-directional diffusion through the first filter in a manner such that substantially no shear is generated by the perfusion of cells.

114. The bioreactor of claim 113, wherein the pores of the first filter are sized to have a dimension smaller than 400 nanometers cross-sectionally.

115. The bioreactor of claim 111, further comprising a plurality of posts positioned between the first surface of the first substrate and the first surface of the first filter to substantially maintain a predetermined separation between the first surface of the first substrate and the first surface of the first filter to allow optical detecting of dynamic activities of cells in the first subchamber.

116. The bioreactor of claim 115, further comprising a plurality of posts positioned between the second surface of the second substrate and the second surface of the first filter to substantially maintain a predetermined separation between the second surface of the second substrate and the second surface of the first filter to allow optical detecting of dynamic activities of cells in the second subchamber.

117. The bioreactor of claim 116, wherein the plurality of posts are positioned in at least two rows, and wherein each row of posts has at least two posts spaced from each other.

118. The bioreactor of claim 116, wherein when a first flow of liquid is introduced into the first subchamber, the first flow of liquid is controlled so as to provide a known shear force to a first layer of cells growing in the first subchamber on the first surface side of the first filter and an environment that simulates a vascular space in the first subchamber.

119. The bioreactor of claim 118, wherein when a second flow of liquid is introduced into the second subchamber, the second flow of liquid is controlled so as to provide an environment that simulates a tissue space in the second subchamber.

120. The bioreactor of claim 119, wherein the first flow of liquid and the second flow of liquid are different.

121. The bioreactor of claim 118, wherein a second layer of cells is capable of growing in the second subchamber on the second surface side of the first filter.

122. The bioreactor of claim 121, wherein the first layer of cells growing in the first subchamber and the second layer of cells growing in the second subchamber are different.

123. The bioreactor of claim 108, wherein the perfusion means comprises:
(a) a second filter with a plurality of pores in fluid communication with the second subchamber, wherein the pores are sized to allow diffusional exchange of nutrients and metabolic byproducts with the second subchamber and not to allow cells to migrate across the second filter; and
(b) a perfusion supply network in fluid communication with the second filter through the pores.

124. The bioreactor of claim 123, wherein the perfusion supply network comprises:
(a) a plurality of perfusion channels, each being in fluid communication with the second filter to allow bi-directional, diffusional exchange of nutrients and metabolic byproducts with the second filter and being dimensioned to minimize pressure drops along each perfusion channel and to allow passive diffusional exchange of nutrients and metabolic byproducts along each perfusion channel;
(b) a plurality of intermediate supply channels, each being in fluid communication with a plurality of corresponding perfusion channels so as to provide perfusate to the plurality of corresponding perfusion channels; and
(c) a plurality of intermediate return channels, each being in fluid communication with a plurality of corresponding perfusion channels so as to collect perfusate from the plurality of corresponding perfusion channels.

125. The bioreactor of claim 124, wherein the perfusion supply network further comprises:
(a) a plurality of main supply channels, each being in fluid communication with a plurality of corresponding intermediate supply channels so as to provide perfusate to the plurality of corresponding intermediate supply channels; and
(b) a plurality of main return channels, each being in fluid communication with a plurality of corresponding intermediate return channels so as to collect perfusate from the plurality of corresponding intermediate return channels.

126. The bioreactor of claim 123, wherein the pores of the second filter are sized to have a dimension smaller than 400 nanometers cross-sectionally.

127. The bioreactor of claim 123, wherein the first filter and the second filter are different.

128. The bioreactor of claim 109, further comprising at least one insertion member defining a cavity therein, wherein the insertion member has a length L and is positioned through the second substrate such that the cavity of the insertion member is in fluid communication with the first subchamber.

129. The bioreactor of claim 128, further comprising a plug having a first surface and an opposite second surface and complimentary to a corresponding insertion member such that when the plug is received into the cavity of the corresponding insertion member, the plug engages with the body of the corresponding insertion member to seal the cavity and a volume is formed between the first surface and the first filter to allow a collection of cells to be received therein.

130. The bioreactor of claim 129, wherein the collection of cells comprises tumor cells.

131. The bioreactor of claim 130, wherein the plug further defines a port in fluid communication with the volume for injecting or withdrawing a stream of substance affecting the growth of the tumor cells.

132. The bioreactor of claim 128, further comprising a cage adapted for separating the tumor cells from the first subchamber.

133. The bioreactor of claim 128, further comprising a plurality of electrodes adapted for electrochemical measurements of the tumor cells.

134. The bioreactor of claim 108, further comprising an extension port member defining a channel therein, wherein the extension port member is positioned such that the channel of the extension port member is in fluid communication with the first subchamber to allow a stream of substance is introduced to the first subchamber.

135. The bioreactor of claim 134, wherein the stream of substance is controlled so as to provide a gradient to the first subchamber.

136. The bioreactor of claim 135, wherein the stream of substance comprises chemokine.

137. The bioreactor of claim 135, wherein the stream of substance comprises a substance affecting the growth of cells.

138. The bioreactor of claim 108, wherein the second substrate is fabricated from glass, Mylar, PDMS, silicon, a polymer, a semiconductor, or any combination of them.

139. The bioreactor of claim 108, wherein the first substrate is at least partially optically transparent.

140. The bioreactor of claim 108, wherein the stream of substance is controlled so as to provide a gradient to the second subchamber.

141. The bioreactor of claim 140, wherein the stream of substance comprises chemokine.

142. The bioreactor of claim 140, wherein the stream of substance comprises a substance affecting the growth of cells.

143. A layered perfusion system for use in a bioreactor, wherein the bioreactor defines a chamber for receiving cells and liquid medium, comprising:
(a) a filter having a first surface and an opposite, second surface and a plurality of pores defined therein; and
(b) a perfusion supply network in fluid communication with the filter through the pores.

144. The bioreactor of claim 143, wherein the perfusion supply network comprises a first perfusion system layer having a first surface and an opposite, second surface and a plurality of perfusion channels defined therein, wherein the first surface of the first perfusion system layer is received by the second surface of the filter such that at each of the plurality of perfusion channels is in fluid communication with the filter to allow bi-directional, diffusional exchange of nutrients and metabolic byproducts with the filter and is dimensioned to minimize pressure drops along each perfusion channel and to allow passive diffusional exchange of nutrients and metabolic byproducts along each perfusion channel.

145. The bioreactor of claim 144, wherein the perfusion supply network further comprises a second perfusion system layer having a first surface and an opposite, second surface and a plurality of perfusion supply and return channels defined therein, wherein the first surface of the second perfusion system layer is received by the second surface of the first perfusion system layer such that each of the plurality of perfusion supply and return channels is in fluid communication with at least one of the plurality of perfusion channels, and wherein the plurality of perfusion supply and return channels are formed along a direction substantially perpendicular to that of the plurality of perfusion channels.

146. The bioreactor of claim 145, wherein the perfusion supply network further comprises a third perfusion system layer having a first surface and an opposite, second surface and a plurality of intermediate supply and return channels defined therein, wherein the first surface of the third perfusion system layer is received by the second surface of the second perfusion system layer such that each of the plurality of intermediate supply and return channels is in fluid communication with at least one of the plurality of perfusion supply and return channels, and wherein the plurality of intermediate supply and return channels are formed along a direction substantially perpendicular to that of the plurality of perfusion supply and return channels.

147. The bioreactor of claim 146, wherein the perfusion supply network further comprises a fourth perfusion system layer having a first surface and an opposite, second surface and a plurality of main supply and return channels defined therein, wherein the first surface of the fourth perfusion system layer is received by the second surface of the third perfusion system layer such that each of the plurality of main supply and return channels is in fluid communication with at least one of the plurality of intermediate supply and return channels, and wherein the plurality of main supply and return channels are formed along a direction substantially perpendicular to that of the plurality of intermediate supply and return channels.

148. The bioreactor of claim 147, wherein the perfusion supply network further comprises a fifth perfusion system layer having a first surface and an opposite, second surface, and a supply channel and a return channel defined therein, wherein the first surface of the fifth perfusion system layer is received by the second surface of the fourth perfusion system layer such at both of supply and return channels are in fluid communication with at least one of the plurality of main supply and return channels, and wherein the supply and return channels are formed along a direction substantially perpendicular to that of the plurality of main supply and return channels.

149. The bioreactor of claim 148, further comprising a supply port defining a channel in fluid communication with the supply channel, and a drain port defining a channel in fluid communication with the return channel.

150. The bioreactor of claim 143, wherein the filter is in fluid communication with the chamber of the bioreactor and each of the plurality of perfusion channels is in fluid communication with the filter to allow bi-directional, diffusional exchange of nutrients and metabolic byproducts with the chamber of the bioreactor through the pores of the filter.

151. The bioreactor of claim 143, wherein the pores are sized to allow diffusional exchange of nutrients and metabolic byproducts with the chamber and not to allow cells to migrate across the filter.

152. The bioreactor of claim 143, wherein the pores of the second filter are sized to have a dimension smaller than 400 nanometers cross-sectionally.

153. A method for preparing a layered perfusion system for use in a bioreactor, wherein the bioreactor defines a chamber for receiving cells and liquid medium comprising the steps of:
 (a) arranging a silicon wafer, a silicon-nitride layer, and a coblock polymer layer such that the silicon-nitride layer is positioned between the silicon wafer and the coblock polymer layer;
 (b) etching a plurality of channels in the silicon wafer; and
 (c) etching a plurality of pores through the silicon-nitride layer to form a filter such that the plurality of pores are in fluid communication with the plurality of channels.

154. The bioreactor of claim 153, prior to the step of etching a plurality of pores, further comprising a step of patterning the coblock polymer layer to form a plurality of opening corresponding to positions where the plurality of pores are to be formed.

* * * * *

UNITED STATES PATENT AND TRADEMARK OFFICE
CERTIFICATE OF CORRECTION

PATENT NO. : 7,790,443 B2
APPLICATION NO. : 10/525648
DATED : September 7, 2010
INVENTOR(S) : John P. Wikswo et al.

It is certified that error appears in the above-identified patent and that said Letters Patent is hereby corrected as shown below:

In the Specification:

In Column 1, Lines 4 to 8, delete:

"The present invention was made with Government support under Grant No. N66001-01-C-8064 awarded by the Defense Advanced Research Projects Administration and the Office of Naval Research. The United States Government may have certain rights to this invention pursuant to these grants."

Please replace Column 1, Lines 4 to 8, as follows:

"The present invention was made with Government support under Grant No. N66001-01-C-8064 awarded by the Defense Advanced Research Projects Administration and the Office of Naval Research. The present invention was also made with Government support under Grant 5R43 RR016124-02 awarded by the National Institute of Health. The United States Government has certain rights to this invention."

Signed and Sealed this
Twenty-eighth Day of December, 2010

David J. Kappos
*Director of the United States Patent and Trademark Office*